United States Patent
Berlinger et al.

(10) Patent No.: US 11,751,947 B2
(45) Date of Patent: Sep. 12, 2023

(54) SOFT TISSUE TRACKING USING PHYSIOLOGIC VOLUME RENDERING

(71) Applicant: Brainlab AG, Munich (DE)

(72) Inventors: Kajetan Berlinger, Munich (DE); Birte Domnik, Munich (DE)

(73) Assignee: BRAINLAB AG, Munich (DE)

( * ) Notice: Subject to any disclaimer, the term of this patent is extended or adjusted under 35 U.S.C. 154(b) by 286 days.

(21) Appl. No.: 16/326,813

(22) PCT Filed: May 9, 2018

(86) PCT No.: PCT/EP2018/061944
§ 371 (c)(1),
(2) Date: Feb. 20, 2019

(87) PCT Pub. No.: WO2018/219609
PCT Pub. Date: Dec. 6, 2018

(65) Prior Publication Data
US 2019/0201109 A1    Jul. 4, 2019

Related U.S. Application Data

(63) Continuation-in-part of application No. PCT/EP2017/062990, filed on May 30, 2017.

(51) Int. Cl.
*A61B 34/00* (2016.01)
*A61B 34/20* (2016.01)
(Continued)

(52) U.S. Cl.
CPC .......... *A61B 34/20* (2016.02); *A61B 5/1127* (2013.01); *A61B 90/37* (2016.02); *A61B 90/39* (2016.02);
(Continued)

(58) Field of Classification Search
CPC ....... A61B 34/20; A61B 5/1127; A61B 90/37; A61B 90/39; A61B 5/113;
(Continued)

(56) References Cited

U.S. PATENT DOCUMENTS 6,289,135 B1 * 9/2001 Declerck ................. G06T 7/215
324/309
7,327,865 B2   2/2008 Fu et al.
(Continued)

FOREIGN PATENT DOCUMENTS

EP    2543018 A1    1/2013
EP    3110331 A1    1/2017
(Continued)

OTHER PUBLICATIONS

Gendrin, Christelle et al., Monitoring Tumor Motion by Real Time 2D/3D Registration During Radiotherapy, Radiotherapy and Oncology 102 (2012), pp. 274-280, Aug. 30, 2011, Retrieved from: www.thegreenjournal.com.
(Continued)

*Primary Examiner* — Christopher Koharski
*Assistant Examiner* — Taylor Deutsch
(74) *Attorney, Agent, or Firm* — Gray Ice Higdon

(57) ABSTRACT

The present invention relates to a computer-implemented medical method for improving the suitability of a tracking structure for tracking by tessellating the tracking structure into a plurality of sub-tracking structures. The invention also relates to a computer configured to execute a program corresponding to the method and a medical system for improving the suitability of a tracking structure for tracking, the system including the aforementioned computer.

15 Claims, 19 Drawing Sheets

```
┌─────────────────────────────┐
│ S1.1: acquire identified    │
│       tracking structure    │
│       of a patient          │
└─────────────┬───────────────┘
              │
              ▼
┌─────────────────────────────┐
│ S1.2: tessellate identified │
│       tracking structure    │
│       into a plurality of   │
│       sub-tracking          │
│       structures            │
└─────────────────────────────┘
```

(51) Int. Cl.
*G06T 7/246* (2017.01)
*A61N 5/10* (2006.01)
*A61B 5/11* (2006.01)
*A61B 90/00* (2016.01)
*A61B 5/113* (2006.01)

(52) U.S. Cl.
CPC ............ *A61N 5/1049* (2013.01); *G06T 7/248* (2017.01); *A61B 5/113* (2013.01); *A61B 2034/2065* (2016.02); *A61B 2090/364* (2016.02); *A61B 2090/374* (2016.02); *A61B 2090/376* (2016.02); *A61B 2090/378* (2016.02); *A61B 2090/3762* (2016.02); *A61B 2090/3908* (2016.02); *A61N 5/1048* (2013.01); *A61N 2005/1062* (2013.01); *G06T 2207/10072* (2013.01); *G06T 2207/20021* (2013.01); *G06T 2207/30096* (2013.01)

(58) Field of Classification Search
CPC ...... A61B 2090/376; A61B 2090/3908; A61B 2090/364; A61B 2090/374; A61B 2090/3762; A61B 2034/2065; A61B 2090/378; A61N 5/1049; A61N 2005/1062; A61N 5/1048; G06T 7/248; G06T 2207/10072; G06T 2207/20021; G06T 2207/30096
See application file for complete search history.

(56) References Cited

U.S. PATENT DOCUMENTS

| | | | |
|---|---|---|---|
| 8,597,211 | B2 | 12/2013 | Berlinger |
| 9,014,424 | B2 | 4/2015 | Berlinger et al. |
| 10,166,404 | B2* | 1/2019 | Gemmel ............. A61N 5/1037 |
| 2005/0065421 | A1 | 3/2005 | Burckhardt |
| 2005/0080328 | A1 | 4/2005 | Vass et al. |
| 2008/0037843 | A1 | 2/2008 | Fu et al. |
| 2011/0116703 | A1 | 5/2011 | Fu et al. |
| 2016/0203609 | A1* | 7/2016 | Wang .................. A61B 6/5235 |
| | | | 382/131 |
| 2017/0065832 | A1 | 3/2017 | Berlinger et al. |

FOREIGN PATENT DOCUMENTS

| WO | WO2011019456 A1 | 2/2011 |
|---|---|---|
| WO | WO2017001441 A1 | 1/2017 |

OTHER PUBLICATIONS

Tsai, Yin-Chiao et al., Thin-Plate Spline Technique for Medical Image Deformation, Journal of Medical and Biological Engineering, 20(4): 2000, pp. 203-210, Oct. 16, 2000.

International Search Report and Written Opinion issued in PCT Application No. PCT/EP2018/061944 dated Aug. 13, 2018.

* cited by examiner

| Correlation of trajectory 204a ↔ 204b = 1 (low) | Correlation of trajectory 204a ↔ 204c = 9 (high) | Correlation of trajectory 204a ↔ 204d = 5 (medium) |
|---|---|---|
| Correlation of temperature change 204a ↔ 204b = 97 (high) | Correlation of temperature change 204a ↔ 204c = 52 (medium) | Correlation of temperature change 204a ↔ 204d = 8 (low) |
| … | … | … |

SOFT TISSUE TRACKING USING PHYSIOLOGIC VOLUME RENDERING

The present invention relates to a computer-implemented medical method for improving the suitability of a tracking structure for tracking by tessellating the tracking structure into a plurality of sub-tracking structures. The invention also relates to a computer configured to execute a program corresponding to the method and a medical system for improving the suitability of a tracking structure for tracking, the system including the aforementioned computer.

TECHNICAL BACKGROUND

Aspects of the present invention, examples and exemplary steps and their embodiments are disclosed in the following. Different exemplary features of the invention can be combined in accordance with the invention wherever technically expedient and feasible.

The idea in one aspect focuses on tracking and/or gating of tumors that move due to respiration using X-ray imaging. Most approaches so far require so called 'Fiducials'-artificial markers (e.g. gold)—to be implanted inside or in the closer neighborhood of the tumor to be able to get information about the current location of the target. But the implantation is difficult and may result in a pneumothorax for the patient.

This approach is a fiducial-less one, and bases on published document WO 2015/127970 and filed patent application PCT/EP2016/053291 (as described in Annex A).

One goal described in WO 2015/127970 is the facilitation of the process of identifying the target structure in acquired X-ray images. In most cases the target is hardly visible in the X-ray images, due to interference with other anatomical structures like e.g. ribs, liver, heart, diaphragm which may also lie in the line of sight of the X-ray-imager.

To partly get rid of this interference, the basic idea of WO 2015/127970 is to render DRRs (Digitally Reconstructed Radiographs) from a volume containing the target structure only (e.g. GTV, gross tumor volume) and using this rendered DRR showing nothing but the target (e.g. for radiotherapy treatment) to identify the corresponding structure in the just acquired X-ray image (for tracking of the target). The user therefore defines a Volume of Interest (VOI) in the planning CT (computed tomography) image containing the target. In many cases it helps to include structures surrounding the target for identification, but this—as working on static images—is very risky: Information on whether the structures surrounding the target are moving the same way as the target is missing. Thus, the user may identify the target based on structures surrounding the target that are totally unrelated to the target (regarding movements, for example breathing movements)—but clearly identifiable in the images.

The approach disclosed in PCT/EP2016/053291 (as described in Annex A) faces the challenge that there is a need for dynamic information in the planning image data (e.g. CT image data) allowing to get the maximum information rendered in a 'Target-Identification-DRR'. The exemplary idea described in this document is for example to not exclusively manually identify a VOI and thereby loosing maybe necessary information for target identification. Instead, (all) voxels whose trajectories perfectly correlate with the target trajectory—and only these—are used for rendering the Target-Identification DRR. Thus, an optimal and per selection trustworthy information for target identification is available. Via a slider a threshold can be set how similar a voxel's trajectory (time-dependent spatial movement, for example obtained using 4D-CT image data) has to be to the target trajectory in order to be taken into account for rendering the Target-Identification DRR.

EXEMPLARY SHORT DESCRIPTION OF THE PRESENT INVENTION

In this section, a short and exemplary description of the specific features of the present invention is given which shall not be understood to limit the invention only to the features or a combination of the features described in this section.

The new idea aims to improve the method disclosed in PCT/EP2016/053291 (as described in Annex A) which describes identifying the target area via e.g. a partly manual fusion process. This application focuses mainly on the challenge how the identified target structure shall be tracked, for example using X-ray sequences acquired during treatment.

Several challenges can arise in case a significantly larger tracking pattern (corresponding to an identified target structure and/or an identified tracking structure) than assumed in PCT/EP2016/053291 (as described in Annex A) is used. On the one hand, potential deformation of the tracking pattern can occur and is preferably taken into account since a tracking pattern of that size can't be considered as rigid (during patient movement such as a breathing movement) anymore. On the other hand, having a tracking pattern of that size may cause the problem that with a breathing motion parts of the tracking pattern temporarily leave the field of view of the used imaging system.

The solution bases on the idea to tessellate the tracking structure into a plurality of sub-tracking structures. In case one focuses on stereoscopic tracking, this is for example performed in the volume (for example CT showing the selected dynamic content only), in order to get the same sub-tracking structure identified in both of the stereoscopic imagers. Using epipolar geometry, each of the sub-tracking structure pairs can be tracked stereoscopically ("swarm-tracking").

GENERAL DESCRIPTION OF THE PRESENT INVENTION

The method, the program and the system according to the invention are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The method for example comprises a step of acquiring an identified tracking structure of a patient. The tracking structure is for example identified using a dynamic DRR, a dynamic CT and/or a similarity image (see Annex A) or a dynamic atlas (see Annex B) as will be described later. The tracking structure is for example identified by a user. For example, the tracking structure is identified in image data. For example, the image data is medical image data which describes at least one anatomical structure of a patient. Different types of image data can be used for this purpose which can for example be obtained using imaging methods as laid out in the chapter "Definitions" below. For example, CT image data of a patient can be used as the image data used for identifying the tracking structure. In this case, the tracking structure is for example identified as a 3D object. The image data can for example be segmented using a segmentation algorithm to enable the identification of the tracking structure. The segmentation algorithm can use an anatomic(al) atlas.

The tracking structure is for example an anatomical body part of the patient. For example, the tracking structure includes a target such as a target for treatment (for example treatment by radiotherapy and/or radiosurgery), for example a tumor. The tracking structure is a structure which shall be tracked, for example to determine the position of the target, for example using a known relative position of the target to the tracking structure. The tracking structure for example includes additional structures surrounding the target which move similar like the target. For the assessment of this degree of similarity of movement a user may study a 4DCT and/or a dynamic DRR, a dynamic CT and/or a similarity image (see Annex A) or a dynamic atlas (see Annex B) may be used as described below (see also Annex A and Annex B). For example, the additional structures surrounding the target and included in the tracking structure are structures which are easily identifiable in image data, for example visible for a user and/or detectable, for example detectable by a user and/or by an algorithm. The tracking structure is for example identified as being a part of the image data, i.e. is not identical to the whole content of the image data. For example, the tracking structure is an anatomical body part of the patient included in the image data, while the image data includes additional structures not being part of the tracking structure.

The method may further comprise the step of tessellating the identified tracking structure into a plurality of sub-tracking structures. The meaning of "tessellating" comprises the meaning of "dividing", "partitioning", "sub-dividing", "apportioning" and/or "splitting up" into the plurality of sub-tracking structures. Before the tessellation, the data is constituted so that it defines one block as a tracking structure. Only this one block can be used for tracking, resulting in a single tracking position. The plurality of voxels which form the one block which represents the tracking structure cannot change relative position during tracking. This allows only tracking of the tracking structure as a whole.

After tessellation, the relative positions of sub-tracking structures may change relative to each other, i.e. voxels within individual sub-tracking structures cannot change their relative positions, but voxels in different sub-tracking structures can change their relative positions. This enables an individual tracking of sub-tracking structures which are part of the tracking structure, which is not possible before the tessellation. It should be noted that the sub-tracking structures may each comprise one or more voxels, e.g. a group of voxels, e.g. more than 2, 4, 8, 10, 27, 64, 100, 500, 625 voxels and/or less than 100, 1000 or 10.000 voxels.

The step of tessellating the identified tracking structure into a plurality of sub-tracking structures may for example take into account movement information provided to a user by a 4DCT and/or information of a dynamic DRR, a dynamic CT and/or a similarity image (see Annex A) or a dynamic atlas (see Annex B) describing the similarity of movement of parts of the tracking structure, for example in relation to other parts of the tracking structure or in relation to the target. For example, sub-tracking structures are formed having the same range of similarity of movement. A measure of the similarity can for example be the sum of the magnitudes or the squares of the magnitudes of the difference between two movement indicating values, wherein a first movement indication value is for example the difference between a first position of a first part of the identified tracking structure at a first point in time and a second position of the first part at a second point in time and wherein a second movement indication value is for example the difference between a first position of a second part of the identified tracking structure (or a first position of the target) at a first point in time and a second position of the second part (or a second position of the target) at a second point in time. The maximum similarity may be determined in case the magnitudes or squares of magnitudes are at a minimum and/or below a predetermined threshold.

The identified tracking structure may be tessellated into several groups of sub-tracking structures, wherein each group has the same range of similarity of movement. For example, parts of the identified tracking structure which exhibit closely similar movements (i.e. parts for which the correlations between the respective trajectories lie below a predetermined first threshold and/or above a predetermined second threshold) are grouped together as sub-tracking structures. Alternatively or additionally, a user may select the parts of the identified tracking structure which are to be grouped as individual sub-tracking structures. For this user selection, a representation of the patient image which indicates the movements of the individual anatomical body parts may be used, which may be a 4DCT or generated on the basis of a 4DCT of the patient. For example, parts of the identified tracking structure which exhibit closely similar movement in relation to the target (i.e. parts for which the correlations between the trajectories of the parts and the trajectory of the target lie below a first predetermined threshold and/or above a second predetermined threshold) are grouped together as sub-tracking structures. For example, where correlations are determined, the maximum similarity is determined if the correlations are at a maximum. For example, parts of the identified tracking structure which are spatially continuous, i.e. which represent connected and/or joined together anatomical body parts are grouped together into the sub-tracking structures.

For example, the tessellation is based on one or more predetermined criteria such as a minimum size in one or more dimensions, a maximum size in one or more dimensions, an average size in one or more dimensions and a predetermined geometric shape of the sub-tracking structures such as a cube, a tetrahedron, a pyramid or else. For example, the predetermined criteria set the sub-tracking structures to be cubes with a minimum size of a certain amount of pixels in each dimension. For example, the tessellation is based on geometric boundary conditions such as a distance to a target. For example, the identified tracking structure is tessellated into sub-tracking regions of the same size (i.e. same amount of voxels and/or same dimensions such as length, width and height). For example, the tracking structure is uniformly tessellated, i.e. in a regular geometrical pattern. The tessellation may be performed automatically (by a computer) or alternatively or additionally be based on user input. For example, a user designates the sub-tracking structures and/or the predetermined criteria to be applied to the tessellation. The sub-tracking structures for example are structures which shall be tracked, for example to determine the position of the target, for example using a known relative position of the target to at least some of the sub-tracking structures.

The method for example further comprises a step of acquiring a patient image describing anatomical patient structures. The singular used in the claims is not to be understood as limiting the patient image to a singular image but means "at least one patient image". For example, one or more patient images are acquired and/or the patient image comprises several images of the patient. The patient image may be included in patient image data. For example, the anatomical patient structures are structures easily identifiable in the patient image, for example visible for a user and/or detectable, for example detectable by a user and/or by an algorithm. For example, the patient image is represented by image data, for example image data of the same type as described above with respect to the image data used for identifying the tracking structure. For example, the patient image is medical image data including one or more medical images of a patient. For example, the patient image comprises at least X-ray image obtained by at least one imaging device, for example a first X-ray image obtained by a first imaging device and a second X-ray image obtained by a second imaging device. For example, the first and second imaging devices are positioned in a known relative position to one another, for example as part of a radiotherapy and/or radiosurgery device. The at least one imaging device is for example used to obtain additional images which can for example be used for tracking of structures, for example the identified tracking structure or the sub-tracking structures.

The method may further comprise a step of matching at least one, for example more than one of the plurality of sub-tracking structures with the anatomical patient structures. The matching for example includes a first matching and a second matching. The first matching is for example performed to match the identified tracking structure with the corresponding anatomical patient structures. For example, the anatomical structures included in the tracking structure (for example several ribs and a tumor included in the identified tracking structure) are matched with the corresponding anatomical patient structures included in the patient image (for example the several ribs and the tumor). The first matching may be performed by a user and/or based on an image fusion, for example by a rigid and/or an elastic image fusion algorithm. Additionally or alternatively, the first matching may be based on predetermined registration information describing a transformation from the coordinate system of the tracking structure to the coordinate system of the patient image.

For example, the second matching includes individually matching each of the sub-tracking structures to each of the corresponding (parts of the corresponding) anatomical patient structures. For example, an image fusion algorithm is used for each of these individual matchings, for example a rigid image fusion algorithm or an elastic image fusion algorithm. Alternatively or additionally, at least some of the plurality of sub-tracking structures are matched at the same time, i.e. as a unit, with the anatomical patient structures using an image fusion algorithm, for example a rigid or an elastic fusion algorithm.

For example, the tracking structure and the sub-tracking structures are 3D objects whereas the patient image comprises at least one 2D X-ray image. In this case, the matching for example includes a first step of transforming the tracking structure and/or the sub-tracking structures into 2D tracking regions and/or 2D sub-tracking regions using information on the position of the at least one imaging device. For example, these structures are transformed so as to represent regions corresponding to the structures as viewed from the viewing direction of the at least one imaging device. For example, this transformation is performed by obtaining a digitally reconstructed radiograph (DRR) image of the aforementioned structures, for example using the image data which was used to identify the tracking structure. For example, CT data used to identify the tracking structure is used to create two 2D images which represent the tracking structure as viewed from the first and the second imaging devices used for obtaining the patient image comprising two X-ray images of the patient. In this case, the matching is performed by matching 2D images.

It may well be understood that also a 3D-2D matching may be performed in other cases, for example in case the sub-tracking structures are 3D objects and the patient image is a 2D image and no transformation is performed for the sub-tracking structures. Also, the matching may be a 3D-3D matching, for example if the patient image is included in 3D image data.

The method may further comprise a step of individually tracking the matched sub-tracking structures. For example, each of the sub-tracking structures is tracked individually. For example, one or more tracking images comprising anatomical patient structures are used for this purpose, for example obtained by the at least one imaging system, for example as X-ray images. For example, the at least one anatomical structure corresponding to at least one, for example more than one of the sub-tracking structures is identified individually in the tracking images, for example by matching as noted above and/or by using an image fusion algorithm. In case the information on imaging geometry (e.g. the relative position) of the first imaging system and the second imaging system is known, the position of the at least one identified anatomical structures in the tracking images can be used to determine the position of the corresponding sub-tracking structure in 3D (real world) coordinates which is referred to as reconstruction. In case 3D tracking images are used, such a reconstruction is not necessary to determine the position of the corresponding sub-tracking structure in 3D (real world) coordinates. Other known methods to track an identified structure in real world coordinates can be applied to track each of the sub-tracking structures individually.

The method may further comprise a step of selecting the matched sub-tracking structures for tracking based on predetermined tracking conditions. The predetermined tracking conditions for example include maximal, minimal and/or average (e.g. mode, arithmetic mean, median, weighted average etc.) values of movement, for example movement in one direction (e.g. anterior or posterior direction, caudal or cranial direction, lateral or medial direction, distal or proximal direction right or left direction), maximal, minimal and/or average values of acceleration, for example acceleration in one direction and/or correlation thresholds which describe different thresholds of correlation between a movement of the sub-tracking structure and the target, i.e. using movement trajectories of the sub-tracking structure and the target (for example correlations in one or more of the aforementioned directions). Additionally and/or alternatively, a maximum value of a reconstruction error is included in the predetermined tracking conditions, for example in case 2D images are used for tracking.

In case the matching for tracking in the image of the first imaging system deviates strongly (i.e. deviates more than a prescribed threshold value in at least one spatial direction) from the matching in the image of the second imaging system, a reconstruction error may occur, which can be a sign that at least one of the images used for tracking should not be used for tracking. For example a maximum value of a distance to a point of interest can be included in the predetermined tracking conditions. The point of interest can be equal to an expected position of a sub-tracking structure obtained by reconstruction. For example, a point of interest is defined after matching at least one, for example more than one of the plurality of sub-tracking structures with the anatomical patient structures. The matching for example includes a first matching and a second matching. The first matching is for example performed to match the identified tracking structure with the corresponding anatomical patient structures. For example, the anatomical structures included in the tracking structure (for example several ribs and a tumor included in the identified tracking structure) are matched with the corresponding anatomical patient structures included in the patient image (for example the several ribs and the tumor). The first matching may be performed by a user and/or based on an image fusion, for example by a rigid and/or an elastic image fusion algorithm. Additionally or alternatively, the first matching may be based on predetermined registration information describing a transformation from the coordinate system of the tracking structure to the coordinate system of the patient image. For example, the point of interest is defined after the first matching. For example, the point of interest is a point defined by the matching results, for example a point of the matched identified tracking structure.

It can be assumed that the point of interest moves only in a specific range (for example a maximum of 20-25 mm in a certain spatial direction), for example caused by the breathing motion of the patient, depending on the defined point of interest. This boundary condition can be used to selecting the matched sub-tracking structures for tracking based on predetermined tracking conditions. For example, the distance of a matched sub-tracking structure to the identified point of interest is determined as a first distance and the distance of a tracked sub-tracking structure to the identified point of interest is determined as a second distance. In case the two distances differ from each other less than a predefined threshold, the respective sub-tracking structure is selected for tracking. In this case, the predetermined tracking conditions may include information on the threshold and/or the point of interest. Also, differences in a certain spatial directions may be compared instead of absolute distances.

The method may also comprise a step of individually tracking the selected sub-tracking structures. This tracking is for example performed as laid out above for the sub-tracking structures (for example using 2D tracking images such as X-ray images of the first and the second imaging device). The tracking of this step may be described as "swarm-tracking", since each selected sub-tracking structure is tracked individually. This can for example be used to determine a plurality of individual movement trajectories. Information on the movement on each individual sub-tracking structure may be determined by the tracking.

The method for example further comprises a step of determining an overall tracking position (and/or geometry) of the tracking structure based on the tracking of the selected sub-tracking structures. The overall tracking position is a single position which represents the position of the tracking structure. For example, the position of at least one of the sub-tracking structures obtained by the tracking is used in combination with information on the position of the at least one sub-tracking structure within the tessellated tracking structure for the determination of the overall tracking position of the tracking structure. For example, information on the position of several sub-tracking structures within the tessellated tracking structure (i.e. information on the relative position of the several sub-tracking structures to a predefined position within the tessellated tracking structure, wherein the predefined position is for example the position of a target within the tessellated tracking structure) is used in combination with the position of the several sub-tracking structures obtained by the tracking of the sub-tracking structures to determine the overall position (and/or geometry) of the tracking structure. For example, the position of one of the sub-tracking structures is determined to be the overall tracking position of the tracking structure.

For example, an average position of the sub-tracking structures obtained by the tracking or a weighted average (e.g. mean, mode, median, weighted average etc.) thereof is used for determining the overall tracking position (and/or geometry) of the tracking structure. That is, the average position is determined to be the overall position of the tracking structure. For example, in case a weighted average of the positions of the sub-tracking structures obtained by the tracking is used for determining the overall tracking position, the positions of the sub-tracking structures may be weighted depending on their relative positions in the tessellated tracking structure to a predefined position within the tessellated tracking structure, wherein the predefined position is for example the position of a target such as a tumor within the (identified and/or tessellated) tracking structure.

In case 2D images are used for the tracking as described above, the position of the tracking structure may be determined in 3D coordinates by way of reconstruction of at least one of the sub-tracking structures into 3D coordinates using the corresponding 2D regions in the 2D tracking images representing the at least one sub-tracking structure. In case 3D images are used for tracking, such a reconstruction does not necessarily need to be performed.

The method may further comprise a step of determining a position and/or geometry (e.g. shape, size, outline, volume etc.) of a target structure for treatment and/or a change thereof based on the tracking of the selected sub-tracking structures. For example, the target structure for treatment is an anatomical body part of the patient which is to be treated by radiotherapy and/or radiosurgery, for example a tumor. This target might have been identified in a previous method step, for example during identifying the tracking structure. For example, a 4D CT scan, a dynamic DRR or a dynamic anatomic atlas may be used to identify the target and the tracking structure, whereas X-ray data may be used for the tracking.

Between the time point of acquiring the two different image data may lie several minutes, hours or even days. Also, the position of the patient may be different during the two time points. Therefore, some properties of the target may be different during tracking than during acquisition of the image used to identify the target and the tracking structure. For example, the geometry (shape and/or size) and/or position of the target may change during the tracking, for example in case of movement of anatomic structures of the patient, for example due to a breathing movement and/or due to the effect of the treatment.

The position and/or geometry of the target structure and/or a change thereof is therefore for example not only identified beforehand, but also based on the tracking of the selected sub-tracking regions. For example, the information on the movement of the sub-tracking regions surrounding the target (e.g. the sub-tracking regions with the lowest distance to the target) is used to determine a change of geometry and/or position (e.g. a deformation and/or movement) of the target. For example, based on the tracked positions of a plurality of sub-tracking structures and their position in the tessellated tracking structure, a deformation of the tracking structure is determined. For this determination, for example an estimation of the deformation of the tracking structure is performed which is based on a finite element simulation which minimizes the bending energy in the tracking structure whilst using the tracked positions of the sub-tracking structures as boundary conditions. Interpolation of the positions of the tracked sub-tracking structures may be performed to estimate the deformation of the tracking structure. Alternatively or additionally, a thin-spline technique for medical image deformation can be used to determine the deformation of the tracking structure. For example, the technique disclosed in "Thin-Plate Spline Technique for Medical Image Deformation", Tsai et al., Journal of Medical and Biological Engineering, 20(4): 203-210 2000 may be used for determining the deformation of the tracking structure based on the positions of the sub-tracking structures in the tessellated tracking structure and based on the tracked positions of the stub-tracking structures. Based on the determined deformation of the tracking structure, the position (e.g. change of position) and/or geometry (e.g. change of geometry) of a target structure can be determined using the known relative position of the target structure to the tessellated tracking structure.

For example, first positions of the tracked sub-tracking structures at a first point in time are determined. For example, second positions of the tracked sub-tracking structures at a second point in time are determined. A deformation field between the first positions and the second positions can then be calculated describing a transformation of each of the first positions to the corresponding one of the second positions. The deformation field can for example be calculated so as to describe a positional transformation of the position of several or all voxels or the position of a plurality of groups of voxels from the first point in time to the second point in time. The deformation field can then be applied to the identified tracking structure and/or to the target structure to determine the deformation of the tracking structure and/or of the target structure.

For example, the relative position between the target structure and several predefined parts of the tracking structure is known by performing identification of the target structure before the tracking of the sub-tracking structures. In this case, the determined deformation of the tracking structure may result in different positions of the predefined parts of the tracking structure. Based on these different positions and based on the known relative positions between the identified target structure and the predefined parts of the tracking structure, the position of the tracking structure and/or a deformation thereof may be determined. For example, the aforementioned predefined parts of the tracking structure are sub-tracking structures.

Based on the tracked positions of a plurality of sub-tracking structures and their position in the tessellated tracking structure, a target structure for treatment can be determined which may be different from the target structure identified during identification of the tracking structure. For example, based on the tracked positions of a plurality of sub-tracking structures and their position to the target structure in the tessellated tracking structure, the position and/or geometry of the target structure is determined. For example, an average position of the sub-tracking structures obtained by the tracking or a weighted average (e.g. mean, mode, median, weighted average etc.) thereof is used for determining the position (and/or geometry) of the target structure by using the relative position of the tracking structure to the target structure as determined beforehand (e.g. from the planning CT). For example, it is assumed that this relative position has not changed or has changed only to a certain degree which can be defined by a predetermined threshold. For example, in case a weighted average of the positions of the sub-tracking structures obtained by the tracking is used for determining the position and/or geometry of the target structure, the positions of the sub-tracking structures may be weighted depending on their relative positions in the tessellated tracking structure to a predefined position of a target such as a tumor within the (identified and/or tessellated) tracking structure.

The information describing the position and/or geometry of the target structure determined based on the tracking of the selected sub-tracking structures may be used to control at least one treatment beam of a radiosurgery and/or radiotherapy device, i.e. to control the intensity, position, treatment time and/or collimation (e.g. geometry of a cross section) of at least one treatment beam.

The method may further comprise a step of determining and/or outputting a control signal constituted to control a treatment device based on the tracking of the selected sub-tracking structures. For example, the control signal is based on information on the target structure (tissue type and/or geometry (size and/or shape) and/or position of the target and/or of the change thereof). For example, the control signal indicates at which positions and/or at which angles (e.g. at which gantry angles) the treatment device shall emit a treatment beam and/or which shape the treatment beam shall have. For example, the control signal indicates that the treatment device shall stop emitting a treatment beam, for example in case it is determined based on the tracking of the selected sub-tracking structures that an unintended movement of the patient has occurred (i.e. in case at least one sub-tracking structure has changed position above a predetermined maximal change in position) or that the target has anatomically changed (e.g. detached from an (moving) anatomical body part, for example in case at least one sub-tracking structure which exhibits similar movement relative to the target structure changed position and/or trajectory above a predetermined maximal change).

The invention also relates to a computer implemented method, in which a tracking structure is for example identified using a dynamic DRR (as described in chapter "Definitions" and in Appendix A) of the patient and/or a dynamic CT and/or a similarity image (as also described in Annex A) of the patient and/or a dynamic atlas (as described in chapter "Definitions" and in Appendix B). The tracking structure can be identified beforehand, i.e. before being acquired.

The tracking structure for example exclusively includes parts (e.g. voxels or pixels) which exhibit a high similarity of movement in relation to each other (i.e. parts for which the correlations between the respective trajectories lie above a predetermined threshold).

As a measure of the similarity, a correlation between trajectories may be used, wherein the trajectories describe movement (time-dependent spatial positions) of the parts. For example, where correlations are determined, the maximum similarity is determined if the correlations are at a maximum.

A measure of the similarity can for example be the sum of the magnitudes or the squares of the magnitudes of the difference between two movement indicating values, wherein a first movement indication value is for example the difference between a first position of a first part of the identified tracking structure at a first point in time and a second position of the first part at a second point in time and wherein a second movement indication value is for example the difference between a first position of a second part of the identified tracking structure (or a first position of the target) at a first point in time and a second position of the second part (or a second position of the target) at a second point in time. The maximum similarity may be determined in case the magnitudes or squares of magnitudes are at a minimum and/or below a predetermined threshold.

The tracking structure for example includes parts which exhibit a high similarity of movement in relation to a target (i.e. parts for which the correlations between the trajectories of the parts and the trajectory of the target lie above a predetermined threshold).

For example, parts which are spatially continuous, i.e. which represent connected and/or joined together anatomical body parts are grouped together in the tracking structure.

For example, the tracking structure exclusively includes parts which exhibit both a high similarity of movement in relation to each other and a high similarity of movement in relation to a target. For example, a predetermined threshold value is used to determine whether a high degree of similarity is met, i.e. in case a correlation exceeds the predetermined threshold and/or in case the magnitudes or squares of magnitudes are below the predetermined threshold. For example, the tracking structure exclusively includes parts which exhibit both a high similarity of movement in relation to each other and a high similarity of movement in relation to a target and which are spatially continuous.

For example, the tracking structure is determined based on information on similarity between trajectories, wherein the information may be extracted from a dynamic DRR, a similarity image and/or a dynamic atlas or can be calculated from patient images describing the patient at different points in time, as exemplified in Annex A and Annex B. This information is for example represented by trajectory similarity values as described in Annex A.

The aforementioned trajectories and/or correlations may be obtained from a series of patient images, for example, a plurality of images describing the patient at different points in time. In this case, the position of a part in each of the images describing the patient at different points in time can be determined, for example using image fusion. The positions of the part in each of the images describing the patient at different points in time are for example connected subsequently, i.e. in timely ascending order (starting with the position of the part in a first image describing the patient at a first point in time, then connecting this position to a second position of the part in a second image describing the patient at a second point in time which is later than the first point in time and so on). The connection of the different positions may furthermore be interpolated. As a result, a trajectory is obtained for each individual part in the images describing the patient at different points in time. For example, each of these individual parts is a single voxel or a group of voxels and/or represents an anatomical body part of the patient. For the generation of trajectories and the calculation of the correlations between the trajectories, it is also referred to Annex A.

The aforementioned correlations may be obtained from a similarity image and/or a dynamic DRR (see Annex A). In this case, the correlations of each of the aforementioned individual parts are included in the similarity image (and/or the dynamic DRR) which means that they can be acquired directly without having to be determined based on a sequence of patient images. With respect to the dynamic DRR and the similarity image, it is also referred to the chapter "Definitions" and to Annex A.

The aforementioned trajectories and/or correlations may be obtained from a dynamic atlas. In this case, the trajectories and/or correlations of each of the aforementioned individual parts are included in dynamic atlas data of the dynamic atlas which means that they can be acquired directly without having to be determined based on a sequence of patient images. With respect to the dynamic atlas, it is referred to the chapter "Definitions" and to Annex B.

Alternatively or additionally, a user may select the parts which are to be included in the tracking structure. For this user selection, a representation of the patient image which indicates the movements of the individual anatomical body parts may be used, which may be a 4DCT or generated on the basis of a 4DCT of the patient. For example, a dynamic DRR, a dynamic CT and/or a similarity image (see Annex A) is used as a representation of the patient image which indicates the movements of the individual anatomical body parts. For example, a dynamic atlas image is used as a representation of the patient image which indicates the movements of the individual anatomical body parts.

The so identified tracking structure can for example be used as the identified tracking structure described above and below. For example, the so identified tracking structure can be tessellated into the plurality of sub-tracking structures. A patient image describing anatomical patient structures may be acquired and at least some of the plurality of sub-tracking structures may be matched with the anatomical patient structures. The matched sub-tracking structures may be individually tracked. The matched sub-tracking structures for tracking are for example selected based on predetermined tracking conditions. The selected sub-tracking structures are for example individually tracked. For example, an overall tracking position of the tracking structure is determined based on the tracking of the selected sub-tracking structures. For example, a (position of a) target structure for treatment is determined based on the tracking of the selected sub-tracking structures. For example, a control signal to control a treatment device is determined and/or output based on the tracking of the selected sub-tracking structures. For example, it is determined whether the selected sub-tracking structures fulfill predetermined criteria. If it is determined that the selected sub-tracking structures fulfill the predetermined criteria, the method is for example continued with the step of selecting the matched sub-tracking structures for tracking based on predetermined tracking conditions. If it is determined that the selected sub-tracking structures do not fulfill the predetermined criteria, a new tracking structure may be identified. The identified new tracking structure may be acquired, and the new tracking structure may be tessellated into a plurality of sub-tracking structures. The method may then continue with the step of acquiring a patient image.

The method may further comprise a step of determining whether the selected sub-tracking structures fulfill predetermined criteria. The predetermined criteria for example include visibility of the anatomical body part corresponding to the selected sub-tracking structures during tracking, for example in the images used for tracking. Visibility may be defined by a threshold describing a percentage of tracking images in which the anatomical structures are visible or by a threshold describing a degree of how much of the anatomical body part is visible in at least one or all of the tracking images. For example, the predetermined criteria include anatomical boundary conditions which may define at least one criterion for positional change of the sub-tracking structures, for example a minimum, a maximum and/or an average amount of movement and/or acceleration of the sub-tracking structures in at least one direction. The predetermined criteria may also include a threshold describing a minimum number of sub-tracking structures which have to be used for tracking, i.e. which fulfill at least one of the aforementioned other criteria. For example, it may be the case that even though the sub-tracking structures are selected as noted earlier, some or too many of the selected sub-tracking structures do not fulfill other criteria such as the predetermined criteria noted above. In this case, it may not be advisable to continue with the selected sub-tracking structures since this may result in an inaccurate tracking. The predetermined criteria may also include one or more of the predetermined tracking conditions used for selecting the matched sub-tracking structures for tracking, for example with other and/or stricter (threshold) values.

If it is determined that the selected sub-tracking structures fulfill the predetermined criteria, the method for example continues with at least the aforementioned step of individually tracking the selected sub-tracking structures.

If it is determined that the selected sub-tracking structures do not fulfill the predetermined criteria, for example a new tracking structure is identified using a dynamic DRR, a dynamic CT and/or a similarity image (see Annex A) or a dynamic atlas (see Annex B).

The new tracking structure is for example identified by a user. The new tracking structure is for example identified using a dynamic DRR, a dynamic CT and/or a similarity image (see Annex A) or a dynamic atlas (see Annex B) as described above. For example, the new tracking structure is identified in image data. For example, the image data is medical image data which describes at least one anatomical structure of a patient. Different types of image data can be used for this purpose which can for example be obtained using imaging methods as laid out in the chapter "Definitions" below. For example, CT image data of a patient can be used as the image data used for identifying the new tracking structure. In this case, the new tracking structure is for example identified as a 3D object. The image data can for example be segmented using a segmentation algorithm to enable the identification of the new tracking structure. The segmentation algorithm can use an anatomic(al) atlas.

The new tracking structure is for example an anatomical body part of the patient. For example, the new tracking structure includes a target such as a target for treatment (for example treatment by radiotherapy and/or radiosurgery), for example a tumor. The new tracking structure is a structure which shall be tracked, for example to determine the position of the target, for example using a known relative position of the target to the tracking structure. The new tracking structure for example includes additional structures surrounding the target which move similar like the target. For the assessment of this degree of similarity of movement a user may study a 4DCT and/or a dynamic DRR, a dynamic CT and/or a similarity image (see Annex A) or a dynamic atlas (see Annex B) may be used as described above. For example, the additional structures surrounding the target and included in the new tracking structure are structures which are easily identifiable in image data, for example visible for a user and/or detectable, for example detectable by a user and/or by an algorithm. The new tracking structure is for example identified as being a part of the image data, i.e. is not identical to the whole content of the image data. For example, the new tracking structure is an anatomical body part of the patient included in the image data, while the image data includes additional structures not being part of the new tracking structure.

Consequently, the new tracking structure may be identified in the same way as described above for the tracking structure, with the exception that different thresholds for determination of the dynamic DRR, the dynamic CT and/or the similarity image (see Annex A) or an image generated based on the dynamic atlas (see Annex B) may be used (with respect to the thresholds used for determining the dynamic DRR see Appendix A).

For example, the identified new tracking structure is acquired in the next step and the new tracking structure is tessellated into a plurality of sub-tracking structures. This tessellation is for example performed in the same way as described above with reference to the tracking structure. More precisely, the meaning of "tessellating" comprises the meaning of "dividing", "partitioning", "sub-dividing", "apportioning" and/or "splitting up" into the plurality of sub-tracking structures. Before the tessellation, the data is constituted so that it defines one block as a new tracking structure. Only this one block can be used for tracking, resulting in a single tracking position. The plurality of voxels which form the one block which represents the new tracking structure cannot change relative position during tracking. This allows only tracking of the new tracking structure as a whole.

After tessellation, the relative positions of sub-tracking structures may change relative to each other, i.e. voxels within individual sub-tracking structures cannot change their relative positions, but voxels in different sub-tracking structures can change their relative positions. This enables an individual tracking of sub-tracking structures which are part of the new tracking structure, which is not possible before the tessellation. It should be noted that the sub-tracking structures may each comprise one or move voxels, e.g. a group of voxels, e.g. 2, 4, 8, 27, 64 or other amounts of voxels.

The step of tessellating the identified new tracking structure into a plurality of sub-tracking structures may for example take into account movement information provided to a user by a 4DCT and/or information of a dynamic DRR, a dynamic CT and/or a similarity image (see Annex A) or a dynamic atlas (see Annex B) describing the similarity of movement of parts of the new tracking structure, for example in relation to other parts of the new tracking structure or in relation to the target. For example, sub-tracking structures are formed having the same range of similarity of movement. A measure of the similarity can for example be the sum of the magnitudes or the squares of the magnitudes of the difference between two movement indicating values, wherein a first movement indication value is for example the difference between a first position of a first part of the identified new tracking structure at a first point in time and a second position of the first part at a second point in time and wherein a second movement indication value is for example the difference between a first position of a second part of the identified new tracking structure (or a first position of the target) at a first point in time and a second position of the second part (or a second position of the target) at a second point in time.

The maximum similarity may be determined in case the magnitudes or squares of magnitudes are at a minimum and/or below a predetermined threshold. The identified new tracking structure may be tessellated into several groups of sub-tracking structures, wherein each group has the same range of similarity. For example, parts of the identified new tracking structure which exhibit closely similar movements (i.e. parts for which the correlations between the respective trajectories lie below a predetermined first threshold and/or above a predetermined second threshold) are grouped together as sub-tracking structures. Alternatively or additionally, a user may select the parts of the identified new tracking structure which are to be grouped as individual sub-tracking structures. For this user selection, a representation of the patient image which indicates the movements of the individual anatomical body parts may be used, which may be a 4DCT or generated on the basis of a 4DCT of the patient. For example, parts of the new identified tracking structure which exhibit closely similar movement in relation to the target (i.e. parts for which the correlations between the trajectories of the parts and the trajectory of the target lie below a first predetermined threshold and/or above a second predetermined threshold) are grouped together as sub-tracking structures. For example, where correlations are determined, the maximum similarity is determined if the correlations are at a maximum. For example, parts of the identified new tracking structure which are spatially continuous, i.e. which represent connected and/or joined together anatomical body parts are grouped together into the sub-tracking structures.

For example, the tessellation is based on one or more predetermined criteria such as a minimum size in one or more dimensions, a maximum size in one or more dimensions, an average size in one or more dimensions and a predetermined geometric shape of the sub-tracking structures such as a cube, a tetrahedron, a pyramid or else. For example, the predetermined criteria set the sub-tracking structures to be cubes with a minimum size of a certain amount of pixels in each dimension. The tessellation may be performed automatically (by a computer) or alternatively or additionally be based on user input. For example, a user designates the sub-tracking structures and/or the predetermined criteria to be applied to the tessellation. The sub-tracking structures for example are structures which shall be tracked, for example to determine the position of the target, for example using a known relative position of the target to at least some of the sub-tracking structures.

After the tessellation of the identified new tracking structure into the plurality of sub-tracking structures, the method for example continues at least with the aforementioned step of acquiring a patient image describing anatomical patient structures. In this and all subsequent steps, the sub-tracking structures which were generated by tessellating the identified new tracking structure are used as the sub-tracking structures (i.e. replacing the sub-tracking structures which were generated by tessellating the identified tracking structure).

The invention also relates to a computer program which, when running on at least one processor of at least one computer or when loaded into the memory of at least one computer, causes the at least one computer to perform the method as described above. It also relates to a signal wave, for example a digital signal wave, carrying information which represents the program. Furthermore, the invention relates to a non-transitory computer-readable program storage medium on which this program is stored. Also, the invention relates to at least one computer, comprising at least one processor and a memory, wherein the aforementioned program is running on the at least one processor or is loaded into the memory, or wherein the at least one computer comprises the program storage noted above. The invention also relates to a system comprising the at least one computer noted above and a radiotherapy or radiosurgery treatment device.

This device may further include an imaging device and/or a first imaging device and a second imaging device, for example configured to obtain the patient image, for example a first and a second patient image, for example X-ray images, for example from different points of view.

Definitions

In this section, definitions for specific terminology used in this disclosure are offered which also form part of the present disclosure.

A universal atlas can for example be generated by a data processing method for determining data which are referred to as atlas data and comprise information on a description of an image of a general anatomical structure, wherein this image is referred to as the atlas image, the method comprising the following steps performed by a computer:

acquiring patient data which comprise a description of a set of images of an anatomical structure of a set of patients, wherein the images are referred to as patient images and each patient image is associated with a parameter set which comprises one or more parameters given when the patient images are generated, wherein the parameters influence representations of anatomical elements as expressed by image values in the patient images, the patient data comprising the patient image set and the parameter sets associated with the patient image set;

acquiring model data which comprise information on a description of an image of a model of an anatomical structure of a patient which is referred to as the model image and is associated with the parameter set;

wherein the model of an anatomical structure is referred to as the model structure and comprises a model of at least one anatomical element which is referred to as model element;

wherein the model data comprise:
  model spatial information on a description of the spatial information on the model structure; and
  model element representation information on a description of a plurality of representation data sets which contain information on representations of the at least one model element in the model images to be generated and are referred to as model representation data sets, wherein the model element representation information also describes a determination rule for determining out of the plurality of representation data sets (Table 3) respective model representation data sets for one or more respective model elements in accordance with respective parameter sets, the representation data sets do not include spatial information relating to the at least one model element;

wherein acquiring the model data involves generating, on the basis of the model data and the patient data, the set of model images which respectively represent at least a part of the model structure by using the spatial information on the model structure and particular model representation data sets which are determined by applying the determination rule in accordance with the one or more associated parameter sets and at least one particular model element referred to as corresponding model element, which is to be matched to at least one corresponding anatomical element represented in the patient image and referred to as patient element;

determining matching transformations which are referred to as PM transformations and which are constituted to respectively match the set of patient images of the set of patients to the set of model images by matching images associated with the same parameter set;

determining an inverse average transformation by applying an inverting and averaging operation to the determined PM transformations; and determining the atlas data by:
  applying the determined inverse average transformation to the model data; or
  respectively applying the determined PM transformations to the respective patient images in order to determine matched patient images, averaging the matched patient images in order to determine an average matched patient image, and determining the atlas data by applying the determined inverse average transformation to the average matched patient image. One property of the universal atlas is for example that the spatial information (e.g. positions and/or geometry) and the representation information (e.g. grey values) are stored separately. For further details on the generation of the universal atlas, it is also referred to PCT/EP2013/072005 published as WO 2014/064063.

Matching by the universal atlas (e.g. using the universal atlas) can for example be performed using the method according to one of the following aspects 1) to 10). In particular, aspects 4) to 7) concern the matching between several patient images of different modalities using the universal atlas.

Aspect 1) A data processing method for determining a matching transformation for matching a set of one or more images of an anatomical body structure of a patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the method comprising the following steps performed by a computer:
  acquiring atlas data, comprising the sub-steps of
    acquiring atlas spatial information which contains spatial information on the general anatomical structure, and
    acquiring element representation information which describes a plurality of representation data sets, wherein the element representation information further describes a determination rule for determining out of the plurality of representation data sets respective representation data sets for respective atlas elements in accordance with different respective parameter sets, the representation data sets containing information on representations of the plurality of atlas elements in the atlas images to be generated but not containing the spatial information on the general anatomical structure;
  acquiring patient data, comprising the sub-steps of
    acquiring the patient image set, and
    acquiring one or more of the plurality of parameter sets which are respectively associated with the one or more images of the patient image set;
  generating, on the basis of the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image;
  determining the matching transformation which matches the atlas image set and the patient image set, by matching images associated with the same parameter set to each other.

Aspect 2) The data processing method according to aspect 1), wherein determining the atlas image set involves:
  determining the representation data sets for the corresponding elements, wherein for each atlas image to be determined, one of the representation data sets is determined for each of the corresponding elements in accordance with the determination rule, wherein the determination rule comprises an assignment rule for assigning a respective representation data set to a respective corresponding element in accordance with the parameter set associated with the patient image to which the atlas image which includes the corresponding element is to be matched; and
  determining the atlas image set comprising one or more images which are respectively associated with one of the parameter sets, by respectively using the determined representation data sets to determine the representations of the corresponding elements.

Aspect 3) The data processing method according to any one of the preceding aspects, wherein in order to determine the representation of one or more of the corresponding elements in the one or more atlas images, image values of patient elements are used in combination with determining the matching transformation.

Aspect 4) The data processing method according to any one of the preceding aspects, wherein the step of determining the matching transformation, which matches one of the atlas images and one of the patient images associated with one of the parameter sets to each other, is configured such that the matching transformation is determined on the basis of information on the matching transformation between another of the atlas images and another of the patient images associated with another of the associated parameter sets.

Aspect 5) The data processing method according to any one of the preceding aspects, wherein the matching transformation is designed to deform a part of the geometry of the general anatomical structure in order to match the atlas images to the patient images, and wherein determining the matching transformation involves taking into account information on the influence on matching quality of a deformation of at least one of the atlas images associated with at least one of the parameter sets in order to determine the deformation of at least another of the atlas images which is associated with at least another of the parameter sets and includes corresponding elements which are identical to the corresponding elements included in said at least one of the atlas images.

Aspect 6) The data processing method according to the preceding aspect, wherein determining the matching transformation involves taking into account the fact that the spatial information described by the atlas images is identical and also taking into account information on the spatial correlation between the spatial information described by the patient images in order to determine deformations described by the matching transformation which is applied in order to match the atlas images and patient images to each other.

Aspect 7) The data processing method according to any one of the preceding aspects, wherein the matching transformation comprises a set of coupled transformations referred to as matching sub-transformations, wherein the respective matching sub-transformations respectively match the atlas images associated with one of the associated parameter sets and the patient image which is associated with the same respective associated parameter set to each other, and the matching sub-transformations are coupled in that they each influence the determination of the other.

Aspect 8) The data processing method according to any one of the preceding aspects, wherein the determination rule describes an assignment between the plurality of atlas elements and the plurality of representation data sets by describing a subjective assignment between the atlas elements and representation classes, wherein the respective representation classes respectively represent subsets of the plurality of representation data sets, and wherein for each of the respective representation classes, there is a unique set of characteristic bijective assignments between individual representation data sets of the subsets and individual parameter sets.

Aspect 9) The data processing method according to any one of the preceding aspects, wherein the representation data sets describe at least one of the following types of information on representation: image values for the anatomical elements; ranges of image values for the anatomical elements; the relationship between image values of different anatomical elements; the relationship between image values for one or more of the anatomical elements represented in images associated with different parameter sets; maximum image values for the anatomical elements; minimum image values for the anatomical elements; average image values for the anatomical elements; standard deviations of the average image values and structures of modulations of the image values for the anatomical elements; characteristics of transitions between representations of different anatomical elements.

Aspect 10) The data processing method according to any one of the preceding aspects, wherein the atlas data also comprise spatial flexibility information which describes a flexibility of the position of atlas elements within the general anatomical structure, and wherein the matching transformation is determined on the basis of the spatial flexibility information.

For further details on the aspects 1) to 10) relating to the matching using the universal atlas it is also referred to PCT/EP2012/071241 published as WO 2014/063746.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

The movements of the treatment body parts are for example due to movements which are referred to in the following as "vital movements". Vital movements can be cyclic movements which can for example be caused by breathing which is performed in accordance with a breathing cycle. Reference is also made in this respect to EP 2 189 943 A1 and EP 2 189 940 A1, also published as US 2010/0125195 A1 and US 2010/0160836 A1, respectively, which discuss these vital movements in detail. In order to determine the position of the treatment body parts, analytical devices such as x-ray devices, CT devices or MRT devices are used to generate analytical images (such as x-ray images or MRT images) of the body. Analytical devices for example use imaging methods and are for example devices for analyzing a patient's body, for instance by using waves and/or radiation and/or energy beams, for example electromagnetic waves and/or radiation, ultrasound waves and/or particles beams. Analytical devices are for example devices which generate images (for example, two-dimensional or three-dimensional images) of the patient's body (and for example of internal structures and/or anatomical parts of the patient's body) by analyzing the body. Analytical devices are for example used in medical diagnosis, for example in radiology. However, it can be difficult to identify the treatment body part within the analytical image. It can for example be easier to identify an indicator body part which correlates with changes in the position of the treatment body part and for example the movement of the treatment body part.

The present invention relates to the field of controlling a treatment beam. The treatment beam treats body parts which are to be treated and which are referred to in the following as "treatment body parts". These body parts are for example parts of a patient's body, i.e. anatomical body parts.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

A treatment body part can be treated by one or more treatment beams issued from one or more directions at one or more times. The treatment by means of the at least one treatment beam thus follows a particular spatial and temporal pattern. The term "beam arrangement" is then used to cover the spatial and temporal features of the treatment by means of the at least one treatment beam. The beam arrangement is an arrangement of at least one treatment beam.

The "beam positions" describe the positions of the treatment beams of the beam arrangement. The arrangement of beam positions is referred to as the positional arrangement. A beam position is preferably defined by the beam direction and additional information which allows a specific location, for example in three-dimensional space, to be assigned to the treatment beam, for example information about its co-ordinates in a defined co-ordinate system. The specific location is a point, preferably a point on a straight line. This line is then referred to as a "beam line" and extends in the beam direction, for example along the central axis of the treatment beam. The defined co-ordinate system is preferably defined relative to the treatment device or relative to at least a part of the patient's body. The positional arrangement comprises and for example consists of at least one beam position, for example a discrete set of beam positions (for example, two or more different beam positions), or a continuous multiplicity (manifold) of beam positions.

For example, one or more treatment beams adopt(s) the treatment beam position(s) defined by the positional arrangement simultaneously or sequentially during treatment (for example sequentially if there is only one beam source to emit a treatment beam). If there are several beam sources, it is also possible for at least a subset of the beam positions to be adopted simultaneously by treatment beams during the treatment. For example, one or more subsets of the treatment beams can adopt the beam positions of the positional arrangement in accordance with a predefined sequence. A subset of treatment beams comprises one or more treatment beams. The complete set of treatment beams which comprises one or more treatment beams which adopt(s) all the beam positions defined by the positional arrangement is then the beam arrangement.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionizing radiation is for example used for the purpose of treatment. For example, the treatment beam comprises or consists of ionizing radiation. The ionizing radiation comprises or consists of particles (for example, sub-atomic particles or ions) or electromagnetic waves which are energetic enough to detach electrons from atoms or molecules and so ionize them. Examples of such ionizing radiation include x-rays, high-energy particles (high-energy particle beams) and/or ionizing radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumor are treated using ionizing radiation. The tumor is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

The information on the imaging geometry preferably comprises information which allows the analysis image (x-ray image) to be calculated, given a known relative position between the imaging geometry analysis apparatus and the analysis object (anatomical body part) to be analyzed by x-ray radiation, if the analysis object which is to be analyzed is known, wherein "known" means that the spatial geometry (size and shape) of the analysis object is known. This means for example that three-dimensional, "spatially resolved" information concerning the interaction between the analysis object (anatomical body part) and the analysis radiation (x-ray radiation) is known, wherein "interaction" means for example that the analysis radiation is blocked or partially or completely allowed to pass by the analysis object. The location and in particular orientation of the imaging geometry is for example defined by the position of the x-ray device, for example by the position of the x-ray source and the x-ray detector and/or for example by the position of the multiplicity (manifold) of x-ray beams which pass through the analysis object and are detected by the x-ray detector. The imaging geometry for example describes the position (i.e. the location and in particular the orientation) and the shape (for example, a conical shape exhibiting a specific angle of inclination) of said multiplicity (manifold). The position can for example be represented by the position of an x-ray beam which passes through the center of said multiplicity or by the position of a geometric object (such as a truncated cone) which represents the multiplicity (manifold) of x-ray beams. Information concerning the above-mentioned interaction is preferably known in three dimensions, for example from a three-dimensional CT, and describes the interaction in a spatially resolved way for points and/or regions of the analysis object, for example for all of the points and/or regions of the analysis object. Knowledge of the imaging geometry for example allows the location of a source of the radiation (for example, an x-ray source) to be calculated relative to an image plane (for example, the plane of an x-ray detector).

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyze the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change. In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation).

These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

A 4D-CT is a sequence of three-dimensional CTs. The 4D-CT for example allows to take moving pictures with x-rays. According to an exemplary embodiment, the moving pictures are sorted into "bins", each bin representing one CT which is assigned to a particular point in time. According to exemplary embodiment, for each breathing cycle (which cycles between exhalation and inhalation) several "bins" (CTs) are generated. The sequence of CTs is referred to herein as 4D-CT.

The 4D-CT of a body can show different kinds of movement by the body parts represented in the analytical images of the sequence. The body parts represented by the analytical images are subject to vital movements (see for instance EP 08 169 422.6 and EP 09 160 153.4 as mentioned above). This means that the body parts are moved due to vital functions of the body such as respiration and/or the beat of the heart.

Respiration has usually the dominating influence on the vital movements. Different body parts undergo different changes in position depending on the cause of the vital movement. The magnitude, direction, velocity, acceleration and/or frequency of a change in position can for example differ in accordance with the cause for the change in position and/or in accordance with the position or type of the body part which undergoes the change in position. Body parts moved by the beat of the heart, for example, generally show a smaller amplitude in their changes in position than body parts which are moved due to respiration. In particular, the direction of changes in position, in particular the direction of movements, can differ depending on the cause, i.e. for example, the direction of a movement by a body part caused by respiration differs from the direction of a movement by a body part caused by the beat of the heart. The frequency of changes in position is also for example higher if they are caused by the beat of the heart than if they are caused by respiration.

If, for example, bone structures such as ribs and a diaphragm are shown in an analytical image (CT), these body parts can undergo different changes in position, in particular in different directions, even if due to the same cause such as for instance respiration. The differences between the changes in position are then in particular due to the different types of body parts and/or due to the different positions of the body parts. It is possible for the treatment body part (for example, the tumor) to undergo changes in position which differ from both the changes in the position of the diaphragm and the changes in the position of the bone structure (ribs).

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method, which in the illustrative example of FIG. 1 starts with a step S1.1 of acquiring an identified tracking structure of a patient and continues with a step S1.2 of tessellating the acquired identified tracking structure of the patient into a plurality of sub-tracking structures.

FIG. 2 shows a tracking structure A which is tessellated into a plurality of sub-tracking structures 1 to 9. In this example, the tracking structure comprises different anatomical body parts which are not in contact with each other. As shown in FIG. 2, sub-tracking structure 9 covers a first anatomical body part, whereas sub-tracking structures 1 to 8 cover another anatomical body part which is not in contact with the first anatomical body part. However, all sub-tracking structures may cover the same (integral) anatomical body part. In this example, each portion of the tracking structure which is not connected to other portions is covered by an individual sub-tracking structure, i.e. each sub-tracking structure only includes parts of one (integral) anatomical body structure. The tessellation may be based on additional rules such as a maximum size of the sub-tracking structures. In the example shown in FIG. 2, each sub-tracking structure lays in a cuboid of the same size. Of course, other structures could be used instead of a cuboid, for example tetrahedrons, spheres, cubes or else. Only the parts of the tracking structure which lay in one of these bounding boxes are chosen as the individual sub-tracking structures. FIG. 2 shows a 3D tracking structure and 3D sub-tracking structures as well as 3D bounding boxes. Instead, 2D versions could be used, i.e. a 2D tracking structure, 2D sub-tracking structures and/or 2D bounding boxes, depending on the type of imaging data used.

FIG. 3 shows the tracking structure of FIG. 2 projected into the imaging planes of two imagers. The two imagers may be the first imaging device and the second imaging device described earlier. For example, the imagers are part of a radiotherapy and/or radiosurgery system. Preferably, the imagers have different viewing directions onto the patient. In this example, the imagers acquire X-ray images, i.e. 2D image data. The tracking structure A is projected into the imaging planes of the two imagers for example by creating a DRR of the tracking structure based on information describing the viewing direction of each of the imagers and based on the image data used for identifying the tracking structure. As can be seen in FIG. 3, the projected tracking structure (including the projected sub-tracking structures) has a different appearance in the two images acquired by the two images which depends on their respective viewing angles onto the patient.

This projection might be performed in case 2D image data is used for tracking the tracking structure and/or the sub-tracking structures. For example, a plurality of 2D X-ray images of the patient acquired by the two imagers at different points in time can be used for tracking. Image matching/fusion algorithms may be used to detect an identified structure in each of the plurality of pictures. This results in a detection of a position of an identified structure, for example a sub-tracking structure, in 2D coordinates. Since the spatial and angular relationship between the two imagers is known, the determined 2D coordinate of the identified structure in an X-ray image of the first imager can be used together with the determined 2D coordinate of the identified structure in an X-ray image of the second imager to calculate a 3D coordinate of the identified structure. This process is often referred to as reconstruction.

Figure 4:
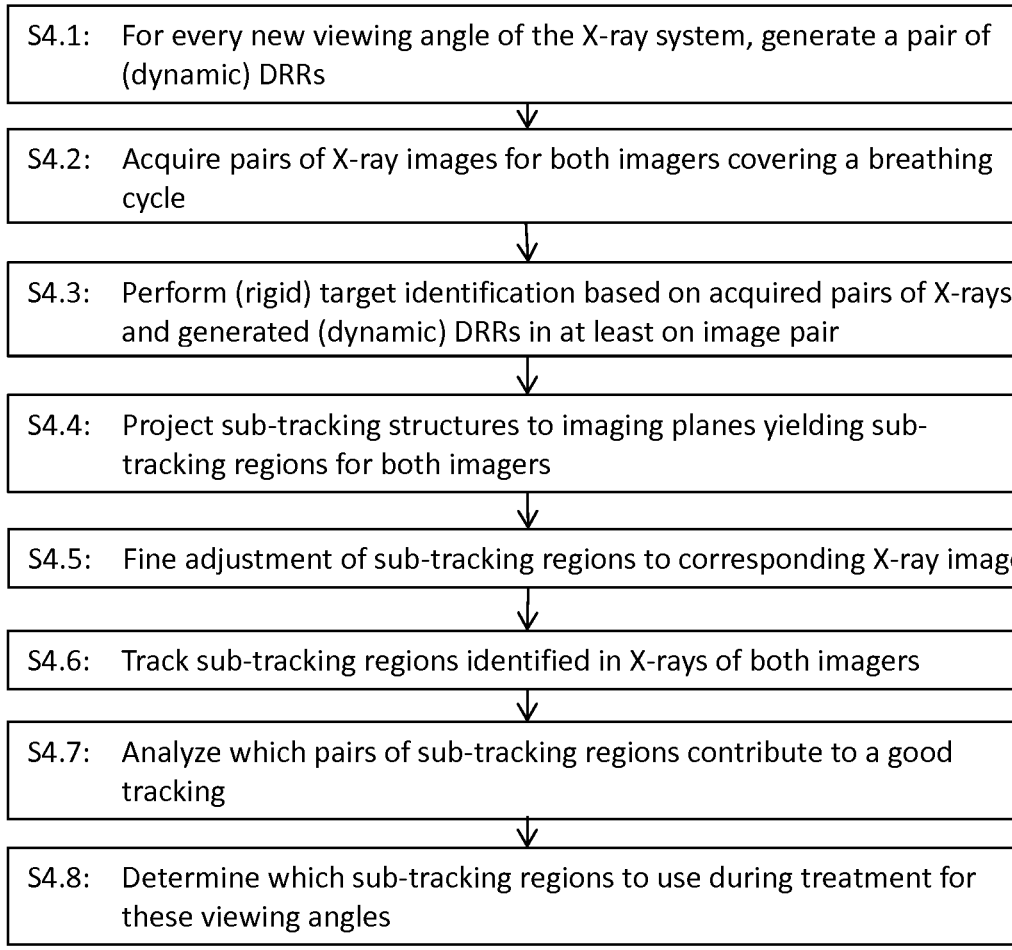
FIG. 4 shows a first sequence of steps of a specific embodiment of the disclosed method.
Figure 5:
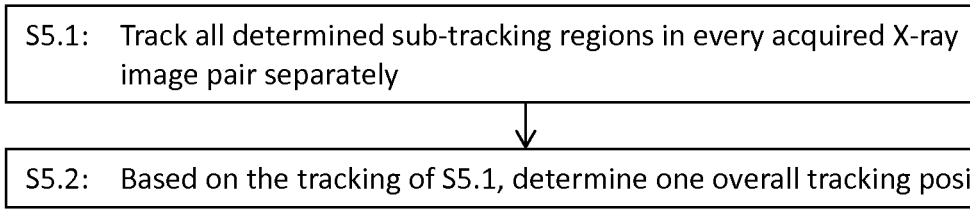
FIG. 5 shows a second sequence of steps of a specific embodiment of the disclosed method.

FIG. 4 shows a first sequence of steps of a specific embodiment of the disclosed method. It should be noted that one or more of the method steps shown in FIGS. 4 and 5 can be performed at the same time or subsequently, some of the steps may be replaced or omitted and additional/alternative steps may be used, wherever possible. In other words, the sequence of steps shown in FIGS. 4 and 5 is not the only embodiment covered by this disclosure. The method may start with the steps S1.1 and S1.2 described above and continue with step S4.1. In step S4.1, a pair of (dynamic) DRRs is created for every new viewing angle of the X-ray system. For example, the "every new viewing angle" corresponds to each viewing angle of each imager (imaging device) and may be defined by a treatment plan. Data on the position of a patient support device such as a patient couch and on the position of a treatment beam may be used to determine the "every new viewing angle". Also, for this purpose a projection from 3D image data to 2D image data may be performed.

Next, in step S4.2 pairs of X-ray images for both imagers are acquired which cover a breathing cycle of a patient, i.e. a plurality of (X-ray) images showing the patient (and/or the anatomical structures and/or anatomical body parts of the patient) at different time points from the viewing angle of each imager are acquired. The pair of X-ray images consists of one image of a first imager and one image of a second imager. The images may have been obtained beforehand, i.e. may be acquired by loading data. The images for example comprise at least a part of the tracking structure and for example a target structure.

Figure 2:
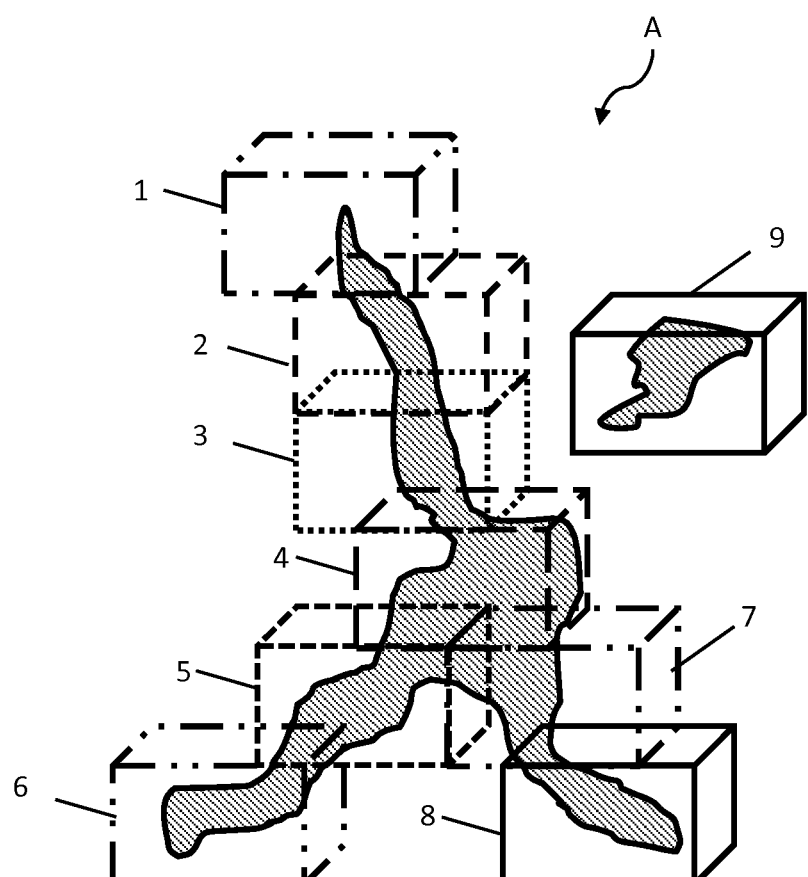
FIG. 2 shows a tracking structure which is tessellated into a plurality of sub-tracking structures.

Next, in step S4.3 a (rigid) target identification is performed based on the acquired X-ray images and the generated (dynamic) DRRs in at least one image pair. This means that the target structure which is comprised (in projected form) in the generated (dynamic) DRRs is matched with a corresponding structure in a pair of X-ray images. For example, the tracking structure A in the generated DRRs shown in FIG. 2 is matched with a corresponding structure in a pair of X-ray images. Alternatively, another structure may be used for this matching and (rigid) target identification process, for example a target structure. In this case, the another structure must also be included in the generated (dynamic) DRRs and in the acquired X-ray images.

After step S4.3, the position of the tracking structure can be identified in 3D coordinates by reconstruction. However, in addition to a positional change of the tracking structure, it may also change its shape during movement of the patient, i.e. during a breathing cycle. In this case, tracking results of the tracking structure may be inaccurate and/or invalid. To take the deformation of the tracking structure into account, individual parts of the tracking structure (the sub-tracking structures) are used as laid out below.

Figure 3:
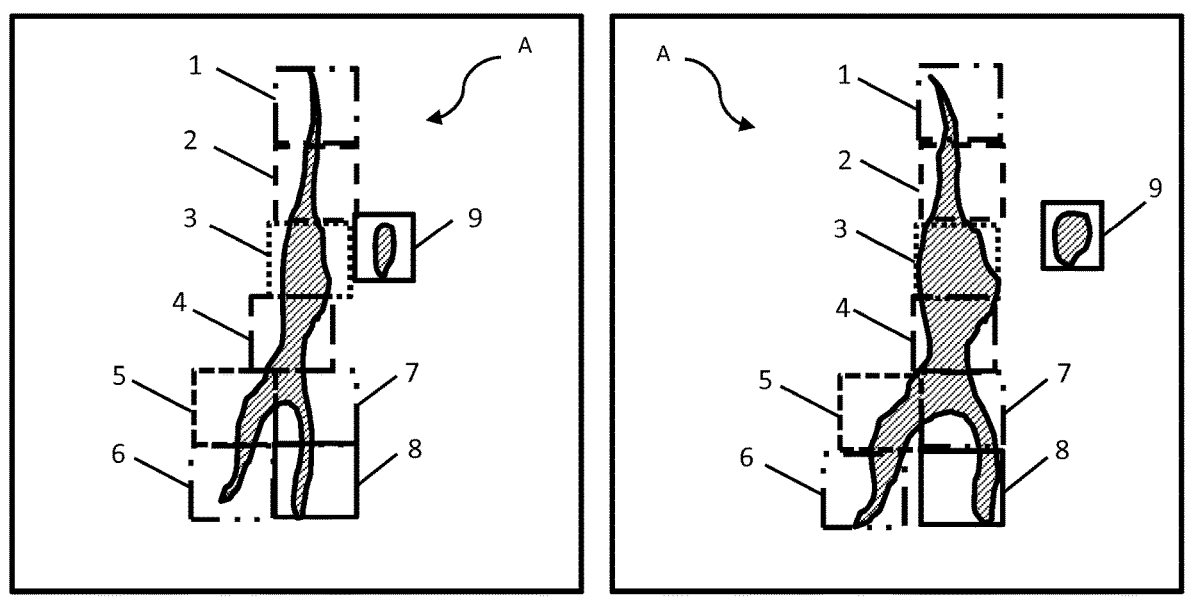
FIG. 3 shows the tracking structure of FIG. 2 projected into the imaging planes of two imaging devices.

In the next step S4.4, the sub-tracking structures are projected to imaging planes (of the two imagers, for example two imaging devices) yielding sub-tracking regions for both imagers. This projection is the same as described above with respect to the target structure. Each of the projected sub-tracking regions corresponds to a part of the identified tracking structure included in one of the bounding boxes as shown in FIG. 3. In case the identified target structure has already been projected into the imaging planes, an additional projection of the sub-tracking structures may be replaced by using information on the tessellation of the tracking structure. For example, the bounding boxes may be projected onto the projected tracking structure to obtain the sub-tracking regions.

In step S4.5, a fine adjustment of the sub-tracking regions to the corresponding X-ray image is performed. This fine adjustment may be a matching of each individual sub-tracking region to the corresponding structure in the X-ray image, for example using an image fusion algorithm. Some or all of the sub-tracking regions may be matched, for example depending on the visibility of the tracking structure in the X-ray images. It should be noted that this fine adjustment as well as the other steps might also be performed using 3D images used for tracking. In this case, the 3D sub-tracking structures are matched with the 3D tracking image(s) for fine adjustment. An elastic fusion may be performed to match the whole tracking structure to the corresponding structure in the X-ray image. Subsequently, the position of each of the sub-tracking structures may be identified using the result of the elastic fusion. The fine adjustment makes sure that a deformation of the tracking structure as shown in the X-ray images is taken into account for subsequent steps. By way of fine adjustment of the sub-tracking regions (or, in case of 3D tracking images the sub-tracking structures), not only a change of position of the tracking structure, but also a deformation thereof can be detected. The fine adjustment may also be necessary in case the shape of the target structure in the image data used for identifying the targets structure is different from the shape of the target structure in the X-ray images, for example in case the position of the patient during CT acquisition is different from the position of the patient when the X-ray images are obtained.

Afterwards, in step S4.6, the sub-tracking regions identified the X-ray images of both imagers (the pair of X-ray images) are tracked. The tracking is performed as described above, for example using additional X-ray images and detecting the position of the identified sub-tracking regions in each of the additional images. A 3D position of the sub-tracking structure corresponding to a pair of sub-tracking regions in each pair of X-ray images may be determined by reconstruction. Thus, the 3D position of each sub-tracking structure can be tracked based on the tracking of the sub-tracking regions.

In step S4.7 it is analyzed which pairs of sub-tracking regions contribute to a good tracking. For this purpose, the visibility of the sub-tracking regions in the plurality of X-ray images may be taken into account, for example using a threshold describing the minimum amount of images in which a sub-tracking region has to be visible or describing the minimum amount of a sub-tracking region which has to be visible in a certain amount of X-ray images. Other parameters may be used to analyze which pairs of sub-tracking regions contribute to a good tracking. For example, pairs which result in a reconstruction error exceeding a certain threshold might be regarded as not contributing to a good tracking. Also, movement information of sub-tracking structures (for example trajectories which describe positional movement over time in 2D or 3D coordinates) may be used for the analysis. In this case, the trajectories may be compared with predetermined trajectories, for example using correlation. Additionally or alternatively, minimal and/or maximal values of the movement information (acceleration and/or absolute movement into a particular direction) may be used to analyze which pairs of sub-tracking regions contribute to a good tracking, for example using threshold values. Of course, other parameters may also additionally or alternatively be used for the analysis.

In step S4.8 it is determined which sub-tracking regions to use during treatment for these viewing angles. The result of the analysis of step 4.7 may be used for this determination. Additional parameters may be used in addition to the parameters described for step S4.7 for this determination. For example, different sub-tracking structures may be used for different viewing angles. The steps S4.1 to S4.7 are performed for each of a plurality of viewing angles which are for example determined by treatment planning data. Therefore, the determination in step S4.8 takes the results of these steps for each of the viewing angles into account and determines which sub-tracking regions to use for tracking for these viewing angles. Not only are the pairs of sub-tracking regions which contribute to a good tracking (S4.7) selected, but some of these selected sub-tracking regions are chosen for each of the different viewing angles (S4.8). This results in a selection of the sub-tracking regions best suitable for tracking for each viewing angle.

FIG. 5 shows a second sequence of steps of a specific embodiment of the disclosed method. The method may perform some or all of the steps S1.1 to S4.8 before continuing with step S5.1. In step S5.1 all determined sub-tracking regions (determined in step S4.8) are tracked in every acquired X-ray image pair separately, i.e. each sub-tracking region is individually tracked. Also, the tracking may include a reconstruction process which results in positions of the sub-tracking structures in 3D coordinates. The tracking is performed as laid out above. This tracking may also be referred to as "swarm-tracking" since not a group of sub-tracking regions (or sub-tracking structures) is tracked as a whole, but each sub-tracking region (or structure) is tracked individually.

This results in swarm-tracking data describing time-dependent positions of each of the sub-tracking regions and/or sub-tracking structures. In contrast thereto, tracking the whole tracking structure or a certain group of sub-tracking structures (regions) results in tracking data describing only one time-dependent position of the tracking structure or the group of sub-tracking structures (regions). This additional information of the swarm-tracking data can be used in a subsequent step (e.g. step S5.2) to improve the tracking accuracy, efficiency and reliability.

In the subsequent step S5.2 an overall tracking position is determined based on the (swarm-)tracking of step S5.1. For example, an average position of the sub-tracking regions is used to determine a reference position in each of the images. Additionally or alternatively, a weighted average may be used. One or more positions of the sub-tracking structures may be discarded for this determination (weighted zero) or used as the only positions (all others weighted zero). Also, the geometrical relationship between the sub-tracking structures (and/or between the sub-tracking regions) can be used for the determination of the overall tracking position. For example, a reference position can be determined in relation the identified tracking structure beforehand, i.e. a target structure. The relative position of each of the sub-tracking structures to the reference position is thereafter determined based on the position of the sub-tracking structures and the reference position. This relative position can subsequently be used during tracking to obtain a positional change of the reference position depending on the movement of the sub-tracking structures, as overall tracking position. As noted above, weighting of the amounts of movement of the individual sub-tracking structures (and/or sub-tracking regions) may be applied in this process. Other alternatives may also be used to determine the overall tracking position. The overall tracking position may also include information on the shape of a target structure. For example, the determined movement of the sub-tracking structures can be used to determine a deformation of anatomical structures adjacent to the sub-tracking structures or included in the tracking structure. This deformation may be used to determine the deformation of a target structure which may lie within or outside of the tracking structure.

Figure 6:
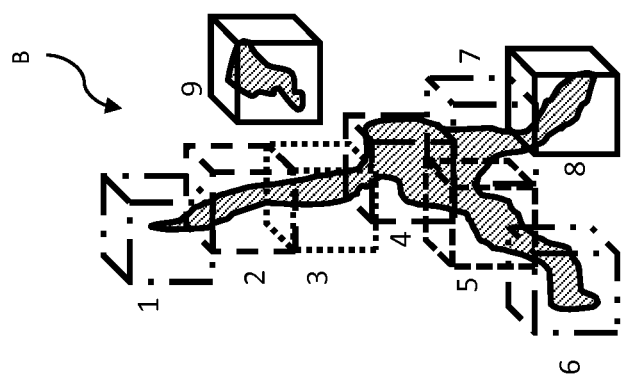
FIG. 6 shows a tracking structure in a first configuration which is tessellated into a plurality of sub-tracking structures.

FIG. 6 shows a tracking structure B in a first configuration (at a first point in time) which is tessellated into a plurality of sub-tracking structures 1 to 9. The tracking structure B may correspond to the tracking structure A described above and the sub-tracking structures 1 to 9 may correspond to the sub-tracking structures 1 to 9 described above. The first point in time is for example the point in time at which a planning image (e.g. planning CT) used for identifying the tracking structure B describes the patient.

Figure 7:
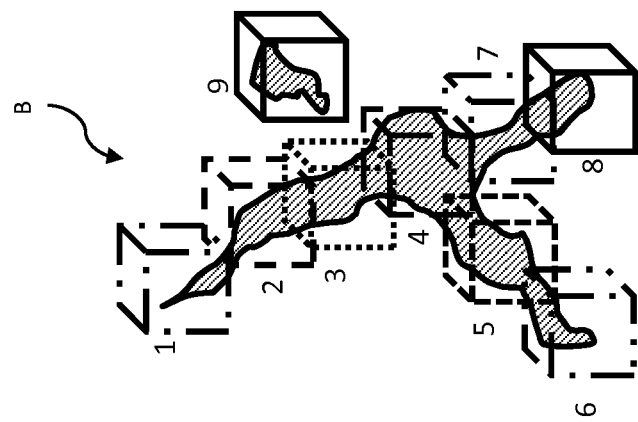
FIG. 7 shows the tracking structure of FIG. 6 in a second configuration wherein the tracking structure is tessellated into the plurality of sub-tracking structures.

FIG. 7 shows the tracking structure B of FIG. 6 in a second configuration (at a second point in time which is later than the first point in time), wherein the tracking structure B is tessellated into the plurality of sub-tracking structures. For example, the second point in time represents a point in time during which tracking of the sub-tracking structures is performed. As can be seen, the geometry of the tracking structure B is different in FIG. 7 compared with FIG. 6. To take this change of geometry and position of the tracking structure into account, the plurality of sub-tracking structures 1 to 9 are tracked individually (swarm-tracking) and an overall tracking position of the tracking structure can be determined since the relative positions of all sub-tracking structures 1 to 9 in the tracking structure B and in relation to one another in the first configuration are known. As described above, a weighted average may be used to determine the overall tracking position of the tracking structure B based on the tracked positions of the sub-tracking structures 1 to 9 in the second configuration. In addition, the geometry (deformation) of the tracking structure B can be determined based on positional differences between the respective positions of the sub-tracking structures 1 to 9 at the first point in time and the respective positions of the sub-tracking structures 1 to 9 at the second point in time, for example by using reference systems for the first and second point in time in which the overall tracking position has not changed. That is, the positional differences (positional changes) are respectively determined for the respective sub-tracking structures. That is, a shift of the overall tracking position is compensated before determining the deformation. For determining the deformation, for example interpolation, elastic image fusion algorithms or the thin-plate spline technique for medical image deformation can be used as described above.

Figure 8:
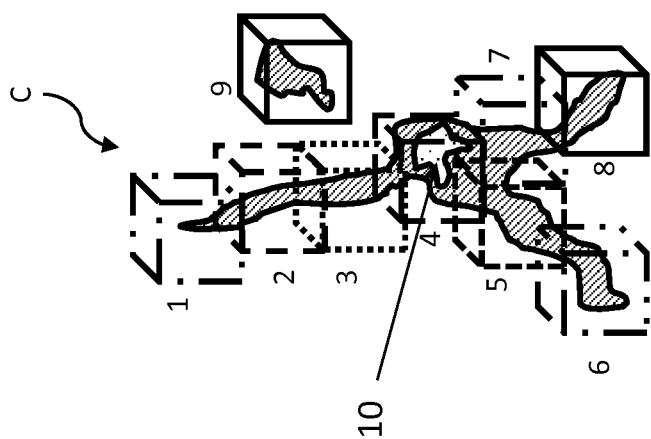
FIG. 8 shows a tracking structure in a first configuration which is tessellated into a plurality of sub-tracking structures, the tracking structure including a target structure.

FIG. 8 shows a tracking structure C in a first configuration (at a first point in time) which is tessellated into a plurality of sub-tracking structures 1 to 9, the tracking structure including a target structure 10. The tracking structure C can correspond to the aforementioned tracking structure A or the aforementioned tracking structure B. Also, the plurality of sub-tracking structures 1 to 9 can correspond to the aforementioned sub-tracking structures 1 to 9. The target structure 10 is in the shown example of FIG. 8 an anatomical body part included in the tracking structure C, but this is not necessarily the case. The target structure 10 can also lie outside of the tracking structure C. The target structure 10 can be planned at the same time the tracking structure C is identified, i.e. during a planning phase using a patient image. The targets structure 10 can also be referred to as "planned target volume" (PTV). The first point in time is for example the point in time at which a planning image (e.g. planning CT) used for identifying the tracking structure C and/or the target structure 10 describes the patient. The relative positions of the sub-tracking structures 1 to 9 to the target structure 10 are known.

Figure 9:
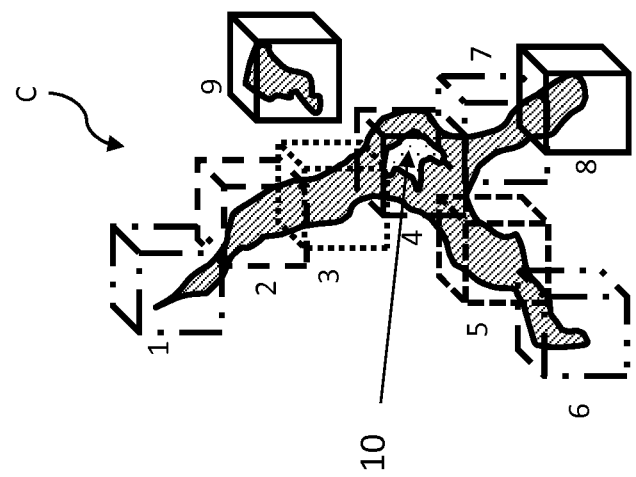
FIG. 9 shows the tracking structure of FIG. 8 in a second configuration wherein the tracking structure is tessellated into the plurality of sub-tracking structures and includes the target structure.

FIG. 9 shows the tracking structure C of FIG. 8 in a second configuration (at a second point in time which is later than the first point in time), wherein the tracking structure C is tessellated into the plurality of sub-tracking structures 1 to 9 and includes the target structure 10. Based on the tracked positions of the sub-tracking structures 1 to 9 and their known relative position to the target structure 10 in the first configuration, the position of the target structure 10 in the second configuration can be determined. For this purpose, a weighted average of the tracked positions of the sub-tracking structures 1 to 9 may be used. For example, the positions of the sub-tracking structures close to the target structure 10 in the first configuration as shown in FIG. 8 are weighted more heavily. In this example, the tracked positions of the sub-tracking 4 may be weighted most heavily, followed by the tracked positions of the sub-tracking structures 3, 5, and 7. The tracked positions of the sub-tracking structures 6, 8 and 3 may be weighted even less, and the tracked position of the sub-tracking structure 9 may be disregarded (weighted zero) since this sub-tracking structure is a small part of the tracking structure which is not attached to the rest of the tracking structure tessellated into the sub-tracking structures 1 to 8. The (weighted) tracked positions of the sub-tracking structures 1 to 9 can be used to determine the position of the target structure 10 at the second configuration (at the second point in time, i.e. during tracking) and/or to determine a deformation of the tracking structure C and/or the target structure 10 compared to the first configuration. For example, first positions of the tracked sub-tracking structures 1 to 10 at a first point in time are determined. For example, second positions of the tracked sub-tracking structures 1 to 10 at a second point in time (which is later than the first point in time) are determined. A transformation between the first positions and the second positions can then be calculated describing a transformation of each of the first positions to the corresponding one of the second positions. Based on a plurality of such transformations, a deformation field can be obtained. The deformation field can for example be calculated so as to describe a positional transformation of the position of several or all voxels or the position of a plurality of groups of voxels (e.g. of each sub-tracking structure) from the first point in time to the second point in time. The deformation field can then be applied to the identified tracking structure (e.g. the tracking structure C shown in FIG. 8) and/or to the target structure (e.g. the target structure 10 shown in FIG. 8) to determine the deformation of the tracking structure (the geometry of the target structure C as shown in FIG. 9) and/or of the target structure (as shown in FIG. 9).

Figure 10:
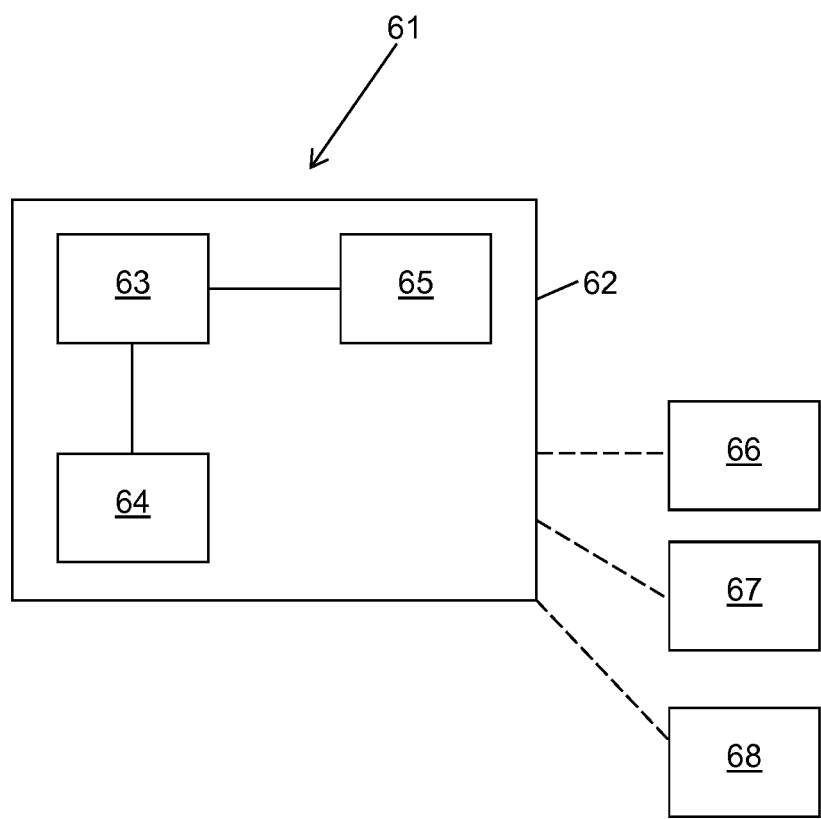
FIG. 10 shows a principle configuration of a system of a specific embodiment of the invention.

FIG. 10 shows a principle configuration of a system of a specific embodiment of the invention: the system 61 comprises a computing environment 62 including at least one computer 63 having at least one digital electronic processor which is operably coupled to at least one electronic data storage device 65 and an output device 64 (e.g. a graphical output device such as a display). The electronic data storage device 65 stores at least one of the (medical) image data or the atlas data or a program. The computer 63 is configured to output, to the output device 64, electronic signals representing a (graphical) representation of a result of the data processing conducted by the computer 63. Furthermore, the computing environment 62 can be coupled to other devices such as a patient positioning device 66, a patient treatment device 67 (for example a radiotherapy and/or radiosurgery device), one or more medical imaging devices (imagers) 68 or else.

Annex A

One aspect of Annex A relates to the digital reconstructing (also called "rendering") of three-dimensional x-ray images (CTs) into two-dimensional images. Those two-dimensional images are referred to as in the art as DRRs. The DRR represents a simulated two-dimensional x-ray under the precondition of a particular (assumed) imaging geometry. The definition of imaging geometry is given below. For example, the rendering is performed so that the particular imaging geometry corresponds to the imaging geometry of at least one (for example one or two) monitoring x-ray device (for generating two dimensional x-ray images) which is used for monitoring a position of a patient in order to place a patient for radiotherapy or radiosurgery in accordance with a plan (for example based on a planning CT). For example an isocenter of the radiotherapy or radiosurgery device and/or an isocenter of the planning CT and/or an isocenter of the particular imaging geometry and/or and isocenter of the at least one monitoring x-ray device are identical.

For example, in the medical field of radiotherapy or radiosurgery (in the following, and in an unlimiting manner the term "radiotherapy" is used only, but has to be understood to cover at least one of radiotherapy or radiosurgery), CTs are used for planning a radiotherapeutic treatment of a patient (for example to treat the targets, for example tumors). The CTs used for planning a radiotherapeutic treatment are referred to in the art as "planning CTs". Planning CTs are used to position the patient during the radiotherapeutic treatment. The radiotherapeutic treatment uses ionizing radiation (particles and/or electromagnetic waves) which are energetic enough to detach electrons from atoms or molecules inside the body and so ionize them. The treatment radiation is for example used in radiotherapy, for example in the field of oncology. For the treatment of cancer in particular, the parts of the body comprising a tumor (which is an example for a "treatment body part") are treated using the ionizing radiation. Since the body and in particular the treatment body part can be moved during positioning of the patient for radiation treatment or during the radiation treatment, it is advantageous to control the position of the treatment beam such that the treatment beam hits the treatment body parts as accurately as possible.

The movements of the treatment body parts are in particular due to movements which are referred to in the following as "vital movements". Reference is made in this respect to the European patent applications EP 0 816 422 and EP 09 161 530 as well as EP 10 707 504 which discuss these vital movements in detail.

In order to determine the position of the treatment body part, analytical devices such as x-ray devices, CT devices, and CBCT devices are used to generate analytical images of the body. The analytical devices are in particular devices for analyzing a body of a patient, for instance by using waves and/or radiation and/or beams of energy in particular electromagnetic waves and/or radiation and/or ultrasound waves and/or particle beams. The analytical devices are in particular devices which generate the above-mentioned two or three-dimensional images of the body of the patient (in particular of anatomical body parts) by analyzing the body.

However, it can be difficult to identify the treatment body part within the analytical image (for instance two-dimensional x-ray image). To this end, the above-mentioned DRRs which are generated from a planning CT in a usual manner are used by an operator to identify the treatment body part in a two-dimensional x-ray image. To this end for instance the (usual) DRR is overlaid over an x-ray image generated when the patient is placed for treatment by means of the ionizing radiation or the DRR is placed aside the two dimensional x-ray image on a display.

According to exemplary embodiments described in Annex A, there is at least one "primary anatomical element". This at least one primary anatomical element corresponds for example to a treatment body part (e.g. tumor) or to one or more other anatomical elements (for example secondary anatomic elements). For example the one or more other anatomical elements are anatomic elements which undergo a vital movement. For example, the other anatomical element is the heart, diaphragm, or rip cage or part thereof. For example, the at least one primary anatomic element is an anatomic element which is represented by at least one voxel (for example cluster of voxels) in for example the undynamic CT or planning CT. The at least one primary anatomical element undergoes particular vital movements. The primary anatomical element can be identified by an operator (for example physician or physicist) in a undynamic CT or in a planning CT. Other anatomical elements, in particular the reminder of anatomical elements shown in the undynamic CT or the planning CT are referred to herein as secondary anatomic elements. Those secondary anatomical elements can or cannot undergo vital movements or can or cannot undergo the same vital movements as the primary anatomical elements. According to at least one exemplary embodiment, an anatomical atlas is used for segmentation of the undynamic CT or the planning CT to identify at least one of primary and secondary anatomical elements. According to at least one exemplary embodiment, an anatomical atlas is used for segmentation of the undynamic CT or the planning CT to segments unlikely to undergo vital movements and to exclude those segments from a determination of trajectories (see below) in order to save processing time and/or to make the determination of the dynamic DRR more robust. For example a vertebral column could be identified to be not subjected to vital movements and corresponding image elements of the 4D-CT could be excluded from the determination of the trajectory similarity values as described below.

According to an exemplary embodiment, the primary anatomical element is represented by at least one voxel, usually a cluster of voxels in the planning CT. The term "a primary anatomical element" does not exclude that there is more than one anatomical element but covers the expression "at least one primary anatomical element". If there is more than one primary anatomical element than those undergo the same vital movements according to an exemplary embodiment. If there is more than one primary anatomical element those are for example distinct, i.e. separated by secondary anatomical elements. According to an exemplary embodiment, there are more than one primary anatomical element and for example the more than one primary anatomical elements are represented by a plurality of imaging elements in the planning CT or 4D-CT. For example, at least some of which are adjacent. For example at least some of which are distinct.

Acquisition of Basic Data

According to at least one exemplary embodiment, 4D-CT data (short "4D-CT") are acquired. The 4D-CT represents a sequence of three-dimensional medical computer tomographic images (sequence of CTs) of an anatomical body part of a patient. The respective three-dimensional images (CTs) of the sequence for example represent the anatomical body part at different points in time. For example, the anatomical body part adopts different positions during a vital movement (e.g. caused by breathing and/or heartbeat). For instance, each CT (also referred to as "volume" or "bin" in the art) corresponds to a specific respiratory state which can be described as percentages of the fully inhaled or fully exhaled state of the patient.

For example, a plurality of different respiratory states are described by the sequence, for example, at least three, for example at least five different respiratory states are respectively described by at least one CT (bin).

For example, the extremes of the cyclic movement (for instance maximum inhalation and/or maximum exhalation) are respectively described by one CT of the sequence.

As mentioned above, one advantage of the exemplary embodiments described herein is that additional information can be provided (for example to an operator) which allows for a better interpretation and/or analysis of the CT and/or the two dimensional x-rays generated for monitoring the position of the patient. According to at least one exemplary embodiment, one of the CTs (bins) of the sequence or a CT determined by interpolation between two CTs defines the planning CT. For example, the interpolation represents a state of the body part intermediate between two neighboring states (respectively described by a sequence CT) which are subsequently adopted by the body part which undergoes the vital movement (for example cyclic movement).

For example, if the 4D-CT does not define the planning CT (e.g. in that one of the CT of the sequence is the planning CT or in that an interpolation of at least two of the CTs of the sequence defines the planning CT), then the planning CT is acquired separately.

Determination of Trajectory Similarity Values

In the following, the determination of trajectory similarity values is described. This determination based on the 4D-CT represents in itself a separate exemplary embodiment which can be supplemented by other steps of other exemplary embodiments (for example a step of displaying the trajectory similarity values) or the determination of the trajectory similarity values of image elements is embedded in at least one exemplary embodiment as described herein.

According to at least one exemplary embodiment a three-dimensional image is acquired from the 4D-CT. The acquisition of the image can for instance be done by selecting one of the CTs (bins) of the sequence defined by the 4D-CT or by determining a three-dimensional image by means of interpolation (as described above) from the 4D-CT. These three dimensional image is referred undynamic CT and for example comprises at least one first image element representing the primary anatomical element. For instance, a plurality of voxels of the undynamic CTs (for instance a cluster of voxels) represents the primary anatomical element (for instance target). For example, only one voxel represents a particular one of the at least one primary anatomical element, for example only one primary anatomical element. The second image elements represent the secondary anatomical elements. For example the undynamic CT is selected by an operator from the sequence CTs to be that one in which a tumor is best discernable. An example for determining a CT suitable for tumor identification and for positioning the patient is given in the following application: WO 2015/127970. According to at least one exemplary embodiment, the undynamic CT is used to determine trajectories. A trajectory which describes the path of a first image element and is referred to as "primary trajectory". A primary trajectory describes the path of the first image element as a function of time. For example, the trajectory describes the path defined by positions of the first image element for different points in time which the first image element adopts in different sequence CTs. The different points in time correspond to different states of the cyclic movement (vital movement) of the primary anatomical element (for instance target). For example the primary trajectory describes in a representative manner the trajectory of more than one first image element as described below.

According to an exemplary embodiment, one of the first image elements in the undynamic CT is defined to correspond to the isocenter of the planning CT. For example, this first image element (which is for example one voxel or more voxels) is referred to as reference image element and used to determine a primary trajectory referred to as reference primary trajectory which describes the path of the reference image element. for this one image element. The reference primary trajectory can be used for calculation of the trajectory similarity value as explained below.

According to a further exemplary embodiment, the reference image element is defined to be that one which is the center of mass of the at least one primary anatomical element (for example center of mass of tumor). Thus, the reference primary trajectory is the trajectory of the center of mass. According to a further exemplary embodiment, the center of mass and the isocenter are identical.

According to a further exemplary embodiment, the reference primary trajectory can be acquired by determining a plurality of trajectories each one describing a trajectory of one or more of the at least one first image elements. Thus a plurality of trajectories are determined which represent the movement of more than one first image element which represent the at least one primary anatomical element. Then the reference primary trajectory is determined by averaging the plurality of trajectories. The averaging can be performed by different mathematical methods, for instance by at least one of mean or mode or median or by weighing particular trajectories (for instance by weighing a trajectory which represents the center of the primary anatomical element (for instance calculated by means of "center of mass" calculation where each voxel is assumed to have the same weight) or the isocenter of the planned radiation treatment) or a combination of the aforementioned methods.

The secondary trajectories respectively describe the trajectory of at least one second image element. For example, a second trajectory may describe the trajectory of only one image element or the second trajectory may describe the trajectory of a plurality (e.g. cluster) of second image elements. The determination of the first and second image elements can in particular be performed by segmentation of the undynamic CT by using an anatomical atlas. For example, image elements are excluded from trajectory determination which are part of an anatomical segment (determined by means of an atlas) which is known to do not undergo vital movements.

According to an exemplary embodiment, the aforementioned at least one primary trajectory and the secondary trajectories are used for determining the trajectory similarity values. The trajectory similarity values respectively describe a similarity between the primary and secondary trajectories. The trajectory similarity value describes in particular a similarity in positional changes of the trajectories (for example correlation, for example correlation coefficient) and/or a similarity of amplitude of cyclic movement (for example similarity of absolute maximum and/or minimum amplitude of the cyclic movement described by the compared trajectories).

According to at least one exemplary embodiment, a respective trajectory similarity value describes a similarity between a respective one of the second trajectories and one of the at least one primary trajectories (which is for example the reference primary trajectory) and/or between a respective one of the at least one primary trajectory and one of the at least one primary trajectories (which is for example the reference primary trajectory).

The trajectory similarity value is for example calculated by using the sum of squared differences (or for example an absolute value function) for each coordinate in which the trajectories is described. The sum of square of differences (or for example absolute value function) can be weighed in dependence on the coordinate. For example, the coordinate system is an orthogonal coordinate system. For example, one or more of the axes of the coordinate system are chosen to be directed along a major movement direction of the vital movement, for example inferior-superior or anterior-posterior. For example, the axes of the coordinate system are the main axes of a three dimensional surface (for example surface of a rotational ellipsoid), the surface being spanned by at least one of the trajectories, for example the reference primary trajectory which describes a cycling movement. For example, the main axes of the rotational ellipsoid can represent the axes of the coordinate system. For example, one of the minuend and subtrahend of the squared difference describes a deviation of a position one of the (primary or secondary) trajectory adopts at a particular point in time (that is the position of an image element (for example a first or second image element)) from an average position the trajectory adopts for the particular point in time (the point in time being within the time covered by the sequence described by the 4D-CT). For example, the average position is determined for one of the coordinate axes and averaged over all points in time (of the sequence). For example, the other one of the minuend and subtrahend of the squared difference describes a position which is adopted by one of the primary trajectories, for example by the reference primary trajectory. Thus, the squared difference is a measure for deviation along an axis. Any other function being a measure for such a deviation and the result of which is independent from an algebraic sign, like the absolute value function, can be used.

The similarity values can also be calculated by using a calculation of correlation coefficients which are for example a measure of the similarity of the trajectories.

The similarity measure (described by the trajectory similarity values) describes for example a similarity of the trajectories which describes for example a similarity of the movement of the image elements described by the trajectories.

The trajectory similarity values can be normalized. The trajectory similarity values can be a function of the peak to peak amplitude. According to exemplary embodiment, the trajectory similarity value describes at least one of the following: the similarity of the movement (e.g. described by correlation coefficient or sum of square differences) or the similarity of the amplitude (for instance peak to peak amplitude) described by the trajectories or the frequency of the cyclic movements described by the trajectories. Details of examples of the calculation of the trajectory similarity value are given below in the description of the detailed exemplary embodiments. According to an exemplary embodiment, the trajectory similarity value describes at least the correlation of the paths of the trajectories and/or of the movements described by the trajectories. According to an exemplary embodiment, for each of the secondary trajectories, the trajectory similarity value is calculated which describes for each of the secondary trajectories the correlation between the secondary trajectory and at least one of the at least one primary trajectory, for example reference primary trajectory. According to an exemplary embodiment, the trajectory similarity value determined in dependence on the correlation coefficient is additional a function of the similarity of the amplitude and/or similarity of the frequency. The function comprises in particular a threshold function. According to an exemplary embodiment, image values of a particular image element of the dynamic DRR are determined as a function of the trajectory similarity values. For example image values are set to black level (lowest brightness) during rendering of the DRR if all trajectory similarity values related to the image values of all image elements used for rendering the particular image element are lower than a threshold value. According to another exemplary embodiment image values of image elements of a planning CT are disregarded (for example by setting them to black level) during rendering of the dynamic DRR if the trajectory similarity value related to the image values of the image used for rendering (for example planning CT or dynamic planning CT) is lower than a threshold value or are changed in color value, for example set to lower brightness than before or changed in color, for example set to a particular color (for example red). According to another exemplary embodiment image elements of a dynamic planning CT are set to black level if the trajectory similarity value related to them is lower than a threshold value or are changed in color value, for example set to lower brightness than before or changed in color, for example set to a particular color (for example red). According to another exemplary embodiment image values of the similarity image or the transformed similarity image are set to black level if the trajectory similarity value related to them is lower than a threshold value or are changed in color value, for example set to lower brightness than before or changed in color, for example set to a particular color (for example red). For example, image values related to trajectory similarity values above a predetermined threshold remain unchanged are not influence by the trajectory similarity values, and remain for example unchanged during determination of the dynamic DRR or their color value is changed, for example are set to higher brightness than before or changed in color (for example hue or saturation), for example set to a particular color (for example green), for example color different from that color set in case of below threshold value.

Determination of the Dynamic DRR

The trajectory similarity values determined as described above are preferably used to determine the dynamic DRR. According to at least one exemplary embodiment, the dynamic DRR is designed to reflect dynamic information on the movements (for example relative movement and/or amplitude and/or frequency) described by the at least one primary trajectories (for example reference primary trajectory) and the secondary trajectories, for example the movement relative to each other, the information being reflected in at least some of the image elements of the dynamic DRR and reflect information of movement related to image elements used for rendering the dynamic DRR. According to at least one embodiment, the dynamic DRR reflects information on the dynamics of anatomic elements in relationship to the dynamics of the at least one primary anatomic element. The information on dynamics (e.g. vital movement) is included in the dynamic DRR which is helpful for identification of the at least one primary anatomic data elements (for example helpful for more reliable target identification) in for example, the dynamic DRR and/or the dynamic CT and/or the similarity image. The information on dynamics helps for an identification of secondary anatomic elements having similar (for example same) vital movements as the at least one primary anatomic element (for example target), in addition to or alternatively to an identification of the at least one primary anatomic element. For example, those secondary anatomic elements identified in the dynamic DRR having similar (for example same) vital movement as the at least one primary anatomic elements are used for positioning a patient (for example for radio therapeutic treatment) for example relative to a beam arrangement (for example treatment beam).

If for example the least one primary anatomic element is an anatomic element other than a treatment body part, like for example the heart or diaphragm or rip cage or part thereof, the dynamic DRR and/or the dynamic CT and/or the similarity image allows to identify secondary anatomic elements having similar (for example same) movement dynamics (for example undergo the same vital movements), for example move in the same way as the heart or diaphragm or rip cage or part thereof.

According to at least one exemplary embodiment, the trajectory similarity values describe information on the dynamics, for example movements (for example relative movement and/or amplitude of (cyclic) movement and/or frequency of (cyclic) movement) described by the at least one primary trajectories (for example reference primary trajectory) and the secondary trajectories, for example information on the dynamics, for example movement (for example relative movement and/or amplitude of (cyclic) movement and/or frequency of (cyclic) movement) relative to each other, for example information on the similarity of the dynamics (for example movements) described by the at least one primary trajectories relative to the secondary trajectories.

If the 4D-CT does not define the planning CT but the planning CT is acquired independently, then preferably a transformation (referred to as "planning transformation") from the undynamic CT to the planning CT is determined and used for determining the dynamic DRR. According to at least one exemplary embodiment, at least a part of the image values of the image elements of the dynamic DRR is determined in dependence on the trajectory similarity values. The dynamic DRRs can be calculated as known in the art. That is, a particular imaging geometry can be defined. This imaging geometry is for instance defined by the position of an x-ray source and an x-ray detector. For instance, the imaginary rays of the x-ray source pass through an imaginary three-dimensional anatomical body part defined by the planning CT or the dynamic planning CT. According to at least one exemplary embodiment, the transmission properties of the image elements (for example voxels) are for example described by Hounsfield units and are for example defined by the brightness of the respective voxels. According to at least one exemplary embodiment, the trajectory similarity values assigned to the respective image elements (e.g. voxels or clusters thereof) of the three-dimensional image have an influence on the virtual absorption properties of the virtual three-dimensional anatomical body part with respect to the virtual rays passing there through. According to other exemplary embodiments, the image values of the respective image elements (e.g. voxels or clusters thereof) describing the virtual three-dimensional anatomical body part and defining the absorption properties of the respective image elements (e.g. voxels or clusters thereof) are changed in dependence on the trajectory similarity values assigned to the respective voxels before the virtual rays pass through the virtual three-dimensional anatomic body part in order to determine the dynamic DRR.

According to an aspect, the planning CT is not used for determining the dynamic DRR, and/or the similarity image and/or the dynamic CT. For example only the 4D-CT is used for determining the dynamic DRR and/or the similarity image and/or the dynamic CT, this is for example done in order to reflect the dynamics, in a static two or three images dimensional image or a sequence of those images, for example to get deeper insight in the vital movements.

According to at least one exemplary embodiment, the image values of image elements of the dynamic DRRs are determined by using (for example considering) the trajectory similarity values such that the brightness of the at least some of the image values are different compared to a DRR determined from the planning CT in a usual manner (i.e. not using the trajectory similarity values, but anything else used for the determination, for example the assumed imaging geometry is the same), such a DRR being referred to herein as "usual DRR". For example, the image values being different relate to image elements representing secondary anatomical elements. According to at least one exemplary embodiment, the image values (for instance brightness) are changed compared to the usual DRR as a function of the trajectory similarity values related to the secondary anatomical element represented by the image value. Trajectory similarity values related to primary anatomical elements are referred to herein as first trajectory similarity values. For example, the first trajectory similarity values are 1. Trajectory similarity values related to secondary anatomical elements are referred to herein as second trajectory similarity values and are for example equal to or lower than the first trajectory similarity values.

The term "related" mentioned above means for example, that they relate to the same particular anatomical element represented in at least one three-dimensional matrix which describes at least one three dimensional image. For example, a trajectory similarity value is related (for example assigned) to a particular image element (for instance voxel) of the planning CT (which particular image element has a particular position in a matrix which describes the planning CT). For example an image value of a particular image element (e.g. voxel or clusters thereof) has been modified based on the trajectory similarity value related to the particular image element, the particular image element representing a particular anatomical element.

Herein, the "positions" in a matrix mean that they relate to a particular anatomical element represented by an image element (for example voxel or cluster thereof) in a three dimensional image. "Same positions" means that they relate to the same particular anatomical element.

Instead of setting image values of image elements (voxels) representing the virtual three-dimensional anatomical body part to black level, it is also possible to disregard those image elements (voxels) when virtually passing the rays there through during rendering of the dynamic DRR. That is, those image elements are handled as if no absorption of the virtual ray happens at the location of the image element (for instance voxel). Correspondingly, if the image value (for instance brightness) is only modified and not set to for instance to minimum brightness (black level), a corresponding procedure would be to modify correspondingly the absorption of the virtual ray when passing to the corresponding image element (for instance voxel). As explained above, there are different ways to determine the dynamic DRR based on the determined trajectory similarity values. At least some of which will be explained below.

According to an exemplary embodiment, the undynamic CT is the planning CT. That is, the planning CT and the acquired undynamic CT are identical. In this case, the step of determining the dynamic DRR uses, according to an exemplary embodiment, the planning CT and the determined trajectory similarity values for determining the dynamic DRR. According to an exemplary embodiment, during determination of the DRR (for example during rendering the DRR) from the planning CT, the trajectory similarity values are considered. According to an exemplary embodiment, the "consideration of the trajectory similarity values", is performed when virtually passing the rays from the virtual radiation source through the virtual three-dimensional anatomical body part described by the planning CT. For example, the image values describe the transmission and/or absorption properties of the virtual three-dimensional body parts, for example by means of Hounsfield values (for example Hounsfield units). According to an exemplary embodiment, the transmission and/or absorption properties described by the image values of the planning CT are modified in accordance with the trajectory similarity values related to (for example assigned to) the different positions of the three dimensional matrix representing the planning CT. For example, if a trajectory similarity value assigned to a particular position of the matrix indicates no similarity, then unattenuated transmission is defined for the position during rendering of the dynamic DRR.

Herein, a change, for example a modification of an image value covers at least one of change of brightness or change of color (for example change of hue and/or change of saturation).

According to a further exemplary embodiment, the brightness values of the planning CT describes the transmission and/or absorption properties of anatomical elements represented by image values of the planning CT. For example, the brightness values are modified in accordance with the trajectory similarity values assigned to the respective positions of the matrix describing the planning CT. Alternatively or additionally, the colors of the image elements are modified in accordance with the trajectory similarity values (for example red in case of low similarity and green in case of high similarity). According to this exemplary embodiment, the planning CT is modified based on the trajectory similarity values assigned to the respective image elements (e.g. voxels) of the planning CT. That is, a modified planning CT is determined based on the trajectory similarity values. This modified planning CT describes a modified virtual anatomical body part through which the virtual rays pass in order to determine the dynamic DRR. For example elements of the virtual anatomical body part are fully transmissive for x-ray, if trajectory similarity values related to these elements are below a threshold value. The planning CT modified by the trajectory similarity values respectively assigned to the image elements of the planning CT is also referred to herein as "dynamic planning CT". For example, the dynamic planning CT describes the transmission and/or absorption properties of a virtual anatomical body part through which the virtual ray pass during rendering of the dynamic DRR. Sometimes in the art, a CT generated by using contrast agents is referred to as a "dynamic CT". Herein "dynamic" is used in a different manner and a "dynamic CT" or a "dynamic planning CT" can be generated by using a contrast agent or by not using a contrast agent. Correspondingly, "undynamic" is used in a different manner and a "undynamic CT" can be generated by using a contrast agent or by not using a contrast agent.

According to further exemplary embodiments, the planning CT is not determined based on the 4D-CT but determined separately. According to an exemplary embodiment, in this case, a transformation is determined from the acquired undynamic CT to the planning CT.

Based on the trajectory similarity values determined as mentioned above, a three-dimensional image is acquired. This three-dimensional image is referred to as "similarity image". The positions of the image elements (for example voxels or clusters thereof) of the similarity image in a matrix which describes the similarity image correspond to positions of image elements of a matrix which describes the undynamic CT and the image values of the image elements of the similarity image correspond to the trajectory similarity values assigned to the corresponding image elements of the undynamic CT. For example, "corresponding positions" means that the respective trajectory similarity values are at the same positions in a matrix which describes the similarity image as the image elements of another matrix which describes the undynamic CT to which they are respectively assigned.

For example, the transformation is applied to the similarity image in order to determine a transformed similarity image. The transformed similarity image is transformed so that the image elements of the transformed similarity image are at positions in a matrix which describes the transformed similarity image which correspond to positions of image elements of another matrix which describes the planning CT, the corresponding positions relate to the same anatomical element. That is, the transformation results in that trajectory similarity values are assigned to the respective image elements of the planning CT.

For example, the dynamic DRR is determined by using the planning CT and the determined trajectory similarity values wherein, during determination of the DRR from the planning CT, the trajectory similarity values represented by the image elements of the transformed similarity image are used. That is, the attenuation of the virtual ray passing through the virtual three-dimensional body represented by the planning CT is modified in dependence on the image values of the transformed similarity image being assigned to respective image elements of the playing CT (as mentioned before).

According to a further example, the image elements of the planning CT are modified based on the transformed similarity image. As mentioned above, the transformed similarity image allows to assign to each image element of the planning CT a trajectory similarity value which is a corresponding image value of the transformed similarity image. The assigned trajectory similarity value is used to change the image values of the planning CT. The term "corresponding" means in this respect that the trajectory similarity values of the transformed similarity image adopt the same position in the transformed similarity image as the corresponding image elements of the planning CT do.

The planning CT modified as mentioned above is referred to herein as "dynamic planning CT". The procedure for determining the DRR is applied to the dynamic planning CT in order to determine the dynamic DRR.

According to at least one further exemplary embodiment, the planning CT is acquired independently from the undynamic CT as described above. In this case, for example, a transformation from the undynamic CT to the planning CT is determined.

Furthermore, for example, a three-dimensional image (referred to as dynamic CT) is determined by changing image values of at least a part of the second image elements of the undynamic CT. The change of the image values is performed in dependence on the trajectory similarity values assigned to respective image elements of the undynamic CT. In other words, for the respective image elements of the undynamic CT, the respectively assigned trajectory similarity values modify the respective image value of the respective image element of the undynamic CT. For example, the trajectory similarity values are determined as mentioned above for the respective image elements of the undynamic CT and then assigned to the respective image elements of the undynamic CT for which they have been determined.

For example, the determined transformation is applied to the dynamic CT in order to determine a CT referred to as "dynamic planning CT". That is the transformation (transformations herein are spatial transformations) transforms the dynamic CT into the dynamic planning CT. At least a part of the second image elements of the dynamic planning CT reflect the previously determined correlation.

For determining the dynamic DRR, for example, the dynamic planning CT is used as a basis for digitally reconstructing the two-dimensional image from the dynamic planning CT. That is, the virtual rays pass through a virtual anatomical body part, the transmission and/or absorption properties of the elements of the body part being described by the image values of the dynamic planning CT.

According to an example of at least one exemplary embodiment, the primary and secondary trajectories are determined as described in the following. Transformations referred to as sequence transformations are determined. The sequence transformation describe transformations between sequence CTs. For example a transformation from the undynamic CT to another one of the sequence CTs (in case the undynamic CT is one of the sequence CTs). For example, the sequence transformations allow to transform between subsequent ones of the sequence CTs. For example, the sequence transformation are constituted to transform from the undynamic CT to other ones of the sequence CTs. The transformations are preferably performed by using image fusion. For example, the sequence transformations are constituted so that the positions of the image elements of a respective one of the sequence CTs can be transformed to the positions of the respective image elements in another respective one of the sequence CTs. Thus, the determined sequence transformations allow to determine a change of position of image elements in the sequence. This change of positions represents trajectories of anatomical elements described by the respective image elements.

For example, the trajectories of the at least one first image element and of at least some of the second image elements are determined by applying the determined sequence transformations to the at least one first image element and to the at least some of the second image elements.

According to at least one exemplary embodiment, the trajectory similarity values are determined based on the trajectories. According to an example of the at least one exemplary embodiment, the trajectory similarity values are determined as a function which has a positive value and is the higher the higher an absolute value of a difference between a minuend and a subtrahend is. The function is referred to as absolute difference function and is for example the function of squared differences, difference to the fourth power, sixth power . . . or a function for obtaining an absolute value of the difference. The minuend and subtrahend depend on positions of two different trajectories at a particular (same) time. One of the two trajectories being a primary trajectory, according to an embodiment the reference primary trajectory.

For example the calculation of the trajectory similarity values can be performed for each coordinate of a coordinate system in which the trajectories are at rest. For instance, a first deviation (difference) of a first image element from a mean average value of the position of the first image element can be subtracted from a second deviation (difference) of a second image element from an average position with respect to the same coordinate and then those two deviations are subtracted and for example the absolute difference function is applied to this difference.

The aforementioned positive values can be weighed differently for each coordinate axis in order to determine a value which reflects the correlation for example for all three axes of the coordination system. This determined value is for example the trajectory similarity value. Furthermore, a threshold function can be applied to value in order to obtain the trajectory similarity value.

According to at least one further exemplary embodiment, the trajectory similarity value is determined based on calculation of a correlation coefficient. For example, the trajectory similarity value is a function of a product of the aforementioned first and second deviations. For example, this function is calculated for each axis of the coordination system. The different values for different axes of the coordination system can be weighed. Optionally a threshold function can be applied to the result of the function in order to obtain trajectory similarity values.

According to a further exemplary embodiment, the trajectory similarity value is a value referred to as amplitude similarity value. For example, the trajectory similarity value is a function, for example threshold function of the amplitude similarity value. For example, the amplitude similarity value reflects similarity of amplitudes of first and second image elements while they undergo a cyclic (for instance periodic) movement. More details are given below in the detailed exemplary embodiments. The aforementioned exemplary embodiments and examples for determining the trajectory similarity value can be combined. According to a further exemplary embodiment both the correlation coefficient and the amplitude similarity value (which describes for example similarity of a peak to peak amplitude) can be combined. For example, both the correlation coefficient and the amplitude similarity value are respectively subjected to a threshold function having respective threshold values. For example, the trajectory similarity value is determined by using a function which sets the trajectory similarity value to a value which indicates similarity if both the correlation coefficient and the amplitude similarity value are above their respective threshold values. If one of them is below, then the trajectory similarity value is set to indicate "not similar" (which for example results in that a corresponding image element in the dynamic DRR is set to black level).

According to at least one exemplary embodiment of Annex A, the computer implemented method further comprises the steps of determining at least one of the at least one first image element or the second image elements by using an anatomical atlas. The steps in particular comprise segmenting the undynamic CT by using the atlas. The segments achieved by means of the segmenting being identified to correspond to one or more (for instance clusters) of the second image elements and/or the at least one first image element. In particular, image elements can be excluded from the processing (for example by not calculating the trajectories for them) which are part of segments known to be not subjected to a vital movement or a vital movement which is not similar to that of the treatment body part. Or for those image elements the trajectory similarity values are set to indicate no similarity.

According to at least one further exemplary embodiment, the computer implemented method comprises the step of displaying the dynamic DRR over an x-ray image (for example by superposition) or besides an x-ray image. The x-ray image is for example used by an operator (for instance surgeon or physicist) to determine the position of a treatment body part to be subjected to treatment radiation. The display of the dynamic DRR can be used for (planning) the positioning of the patient for the radiotherapeutic treatment.

According to an example, image values (for example of the similarity image) representing the trajectory similarity values can have a brightness or color (for example hue and/or saturation) which depends on the trajectory similarity value.

Figure 1:
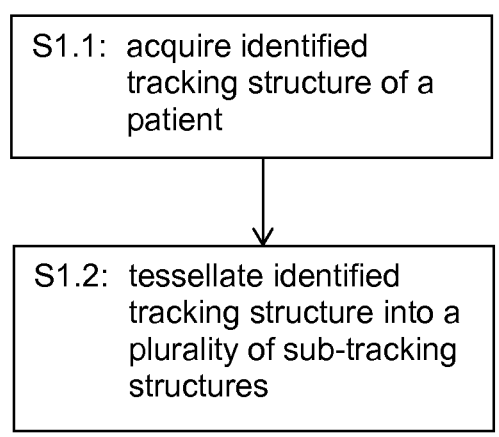
FIG. 1 is a flow diagram showing the basic steps of the disclosed method.

According to a further aspect, a computer implemented method is provided which is for example used to determine the above mentioned similarity image and/or dynamic CT and/or dynamic DRR. The determination is for example based on a 4D-CT, for example not based on a planning CT, for example uses (only) the 4D-CT. The 4D-CT describes for example a sequence of three-dimensional medical computer tomographic images of an anatomical body part (referred to as sequence CTs). The sequence CTs represent the anatomical body part at different points in time. The anatomical body part comprises at least one primary anatomical element and secondary anatomical elements. This further aspect is for example used if no radiotherapeutic treatment is intended for the patient and if there is no need for a planning CT. This further aspect is for example used if further insights in the (anatomical) dynamics of the patient is required. With exception of the use of the planning CT, the method according the further aspect comprises one or more step combinations as described above. According to a further aspect, a complete implement method is provided which uses at least or only the steps shown in FIG. 1 for determining the trajectory similarity values. According to a further aspect, a computer implemented method is provided that uses the steps S20 and S24 of FIG. 2, while in step S24 the dynamic DRR is determined by using the undynamic CT instead of the planning CT. According to further aspects, method uses the steps in FIG. 3 with exception of step as 32. Furthermore, step 34 has changed in that the dynamic CT is determined by using the undynamic CT and the determined trajectory similarity values and by changing image values of the undynamic CT independence on the trajectory similarity values. Finally the step S36 has changed in that the dynamic DRR is determined from the dynamic CT. According to aspects, at least one of the dynamic DRR or the dynamic CT is displayed. According to a further aspect, the steps of FIG. 1 are supplemented by step of displaying the determined trajectory similarity values as three-dimensional similarity image.

The computer implemented method according to the further aspect comprises steps as mentioned below, examples for at least some of the steps are described with respect to other aspects described herein and are therefore not (again) described in detail.

For example, the 4D-CT is acquired. A planning CT is acquired. The planning CT is according to a first exemplary embodiment acquired based on the 4D-CT. For example, by interpolation between one of the sequences CTs or by defining one of the sequence CTs to be the planning CT. According to a further alternative exemplary embodiment, the planning CT is acquired independently from the 4D-CT for example by receiving CT data from a medical analytical imaging device which is constituted to generate CTs.

For example the computer implemented method further comprises the step of acquiring a three-dimensional image, referred to as undynamic CT, from the 4D-CT. For example, one of the sequence CTs is selected as the undynamic CT. The selection is for instance performed on a visual basis. For instance, an operator selects one of the sequence CTs in which a treatment body part can be visually best segmented from other body parts. According to a further example, a segmentation of the treatment body part by using an atlas has highest confidence level for the treatment body part in case of the selected sequence CT. The aforementioned features can be combined also with the other aspects mentioned before.

In a further step, for example, a trajectory is acquired, the trajectory is referred to as primary trajectory. The acquisition is for example based on the 4D-CT. The primary trajectory describes a path of the at least one first image element as a function of time.

For example, in a further step, trajectories of the second image elements are acquired. The trajectories are referred to as secondary trajectories. The acquisition is for example based on the 4D-CT.

For example, in a step trajectory similarity values are determined. The trajectory similarity values are determined for the image values of the undynamic CT. The determination is for example based on the primary trajectory and the secondary trajectories. The trajectory similarity values respectively describe a means for similarity as described herein.

For example, in another step, the similarity image is determined by determining the trajectory similarity values to be image values of image elements of a similarity image. The image elements of the similarity image are referred to as similarity image elements. The image elements of the undynamic CT are referred to as undynamic image elements. As described with respect to other aspects, the determination of the similarity image is performed so that the positions of the similarity image elements correspond to the positions of the undynamic image elements of the undynamic CT to which the trajectory similarity values are respectively related.

The acquisition of a planning CT is optional. For example, the similarity image can be determined without using the planning CT.

Optionally, in case the planning CT is not acquired based on the 4D-CT but independently from the 4D-CT, a transformation is further determined from the undynamic CT to the planning CT (examples therefore are described above with respect to the other aspect). For example the determined transformation is applied to the similarity image (examples therefore are described herein with respect to the other aspects).

According to a further exemplary step, the similarity image or the transformed similarity image is displayed For Example, the similarity image is determined for each CT of the sequence CT. For example a change of the similarity images is visualized by a movie play feature.

According to another exemplary embodiment of this aspect, the similarity image or the transformed similarity image is displayed over or besides a CT, for example sequence CT and/or planning CT. According to another exemplary embodiment, a DRR (referred to as similarity DRR) is rendered using the similarity image as the tree dimensional image in the manner described above. For example, the same imaging geometry is used for the rendering of the similarity DRR as for generation of a two-dimensional x-ray image which is for example used for placing a patient. The similarity DRR is for example display over the two-dimensional x-ray (for example superposed) or displayed besides the two-dimensional x-ray image.

According to a further aspect, a program is provided which when running on a computer or when loaded into a computer causes the computer to perform at least one of the computer implemented methods described herein.

According to a further aspect, a signal wave is provided, which carries information which represent the program according to the aforementioned aspect.

According to a further aspect, a program is provided, which comprises code means adapted to perform all the steps of at least one of the computer implemented methods described herein.

According to a further aspect of Annex A, a program storage medium is provided, on which the program according to at least one of the aforementioned aspects is stored. The program is for example stored in a non-transitory manner.

According to a further aspect of Annex A, a computer is provided, on which the program according to at least one of the aforementioned aspects is running or in which such a program is loaded. The computer is for example constituted to perform at least one of the aforementioned computer implemented methods. For example, the computer comprises the program storage medium of one of the aforementioned aspects.

According to further aspects of Annex A, a system is provided. The system comprises for example the computer according to the aforementioned aspect. For example, the system further comprises a display device (for example a computer monitor) for displaying the dynamic DRR determined in accordance with one of the aforementioned aspects. For example, the display device is alternatively or additionally constituted to display the similarity image according to one of the aforementioned aspects. For example, the computer comprises an interface (for example a digital and/or electronic interface) for receiving data, for example the 4D-CT and/or the planning CT.

According to a further exemplary embodiment of this aspect, the system comprises a couch for placing a patient, for example for treatment with treatment radiation. The system for example further comprises according to this exemplary embodiment, a treatment device constituted to emit a treatment beam for treating the patient by means of treatment radiation.

According to a further exemplary embodiment of this aspect, the system comprises an analytical device constituted for generating the 4D-CT.

For example, according to a further exemplary embodiment, the system alternatively or additionally comprises an analytical device constituted for generating the planning CT.

Description of FIGS. 11 to 19

Figure 11:
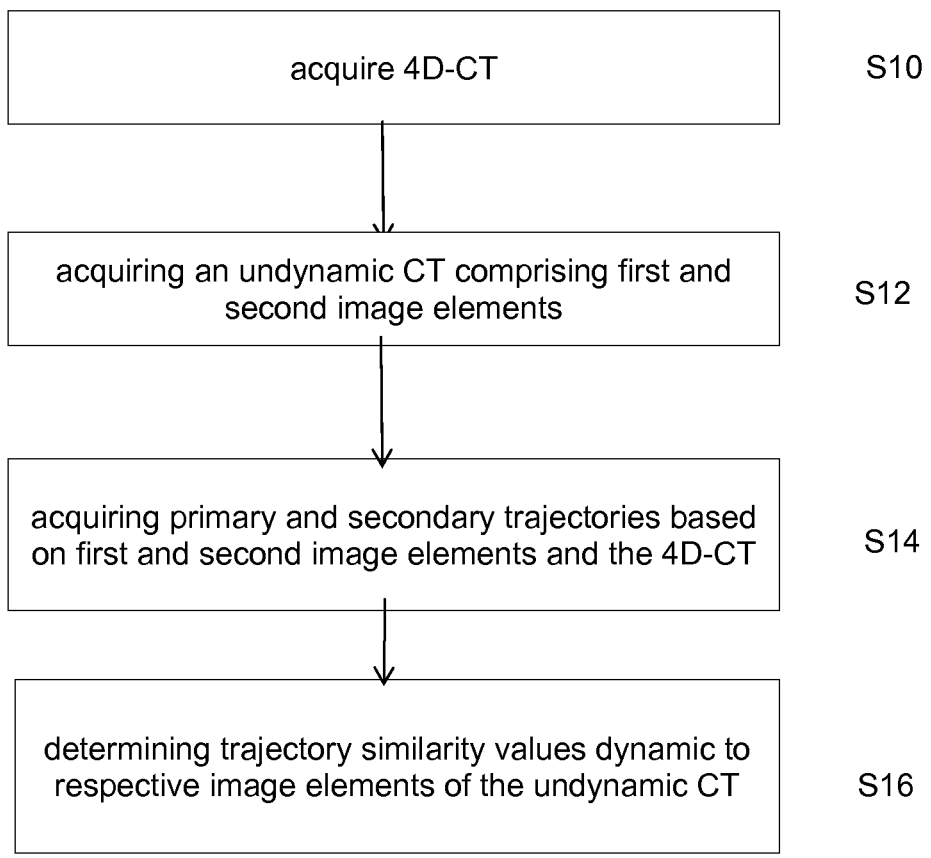
FIG. 11 shows a flowchart related to the determination of trajectory similarity values as described in Annex A.

FIG. 11 shows steps for determining the trajectory similarity values. According to step S12, the undynamic CT is acquired. According to step S14, the primary and secondary trajectories are acquired. For example, the primary and secondary trajectories are determined based on the acquired undynamic CT, for example based on the at least one first image element and the second image elements. For example, the first image element is a tumor. For example the second image elements represent secondary anatomical elements. For example the secondary anatomical elements are discernible in an x-ray image. For example, those secondary anatomical elements have a strong interaction with x-rays (for example by absorbing the x-rays) than fluids (for example water, air).

Figure 17:
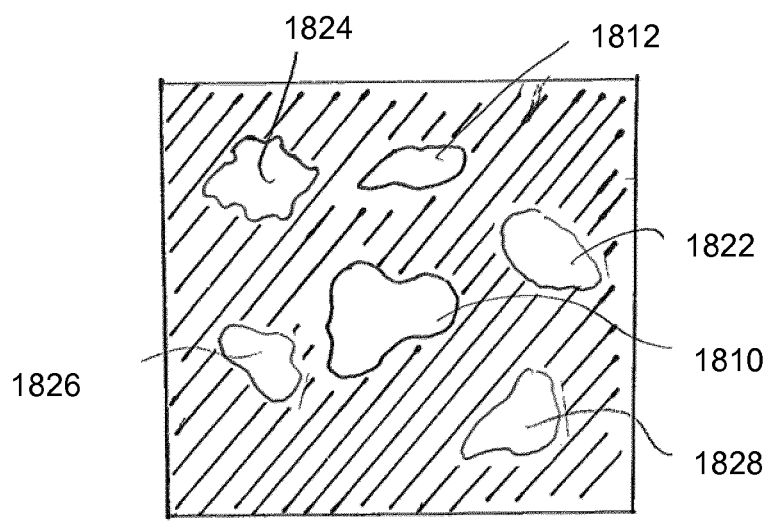
FIG. 17 shows a schematic representation of a usual DRR which was generated from a schematic planning CT in accordance with methods known in the art as described in Annex A.

Having a reference to FIG. 17, it is assumed that FIG. 17 represents a schematic usual DRR generated from the dynamic CT which is assumed to correspond to the planning CT. Then according to an example, region 1810 represents the treatment body part and is generated from a cluster of voxels of the planning CT which corresponds to the undynamic CT. That is, the region 1810 in FIG. 17 corresponds to a cluster of first image elements of the undynamic CT from which the usual DRR of FIG. 17 is generated. Accordingly, according to an example, the regions 1812, 1822, 1824, 1826, and 1828 are generated from clusters of second image elements of the undynamic CT (which is identical to the planning CT).

According to step S14 of the FIG. 11, primary and secondary trajectories are acquired based on first and second image elements of the undynamic CT and based on the other sequence CTs defined by the 4D-CT. As mentioned above, preferably image fusion methods are used to determine the trajectories. In a next step, for example, the trajectory similarity values related to the respective image elements of the undynamic CT are determined. For example, this is done for each voxel of the undynamic CT or for voxel clusters. According to an example, the trajectory similarity values for the voxels being inside the region generated from a voxel cluster of the undynamic CT which results in the regions 1822, 1824, and 1826 are lower than a threshold value and the trajectory similarity values for the voxels inside the voxel clusters of the undynamic CT from which the regions 1810 and 1812 are generated in FIG. 17 have a value above the threshold value. Again, the aforementioned example relates to the case where the undynamic CT corresponds to the planning CT.

Detailed examples for the calculation of trajectory similarity values are given below.

Figure 12:
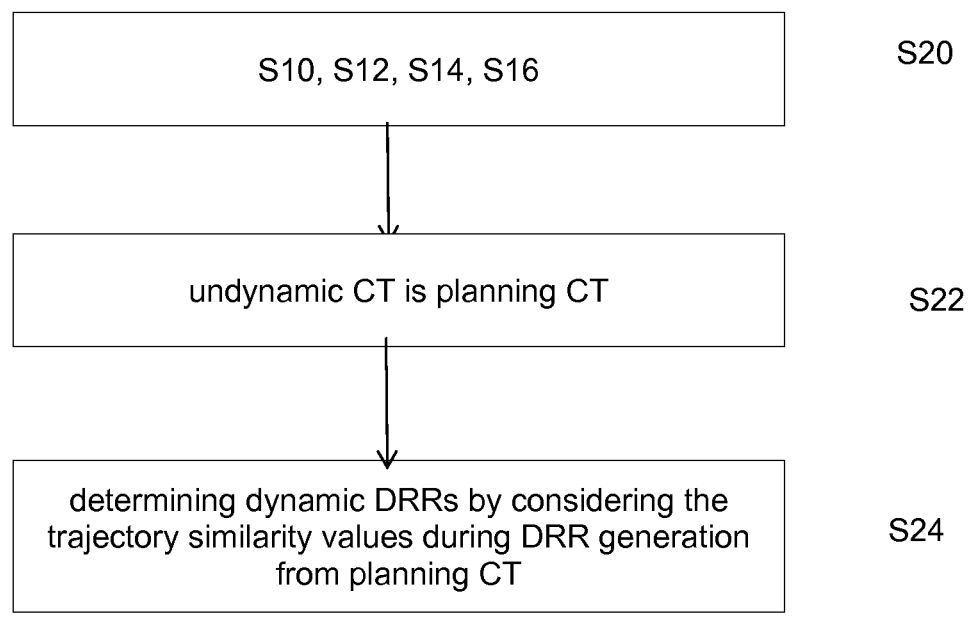
FIG. 12 shows a flowchart according to one exemplary embodiment according to at least one exemplary embodiment for determining dynamic DRRs as described in Annex A.

FIG. 12 relates to an exemplary embodiment for determining the dynamic DRRs according to the flowchart shown in FIG. 12. According to the flowchart shown in FIG. 12, the computer implemented method relates to the case where the undynamic CT is the planning CT. For example, there is a step of selecting one of the sequence CTs as the planning CT and the undynamic CT. This step can be performed by an operator.

For example, the steps of FIG. 11 are also performed according to an exemplary embodiment described in FIG. 12. The combination of steps of FIG. 11 are indicated as step S20 in FIG. 12. For example, it can be defined that the undynamic CT should be the planning CT before or after step S20 or simultaneously to step S20 (see step S22 in FIG. 12).

Figure 18:
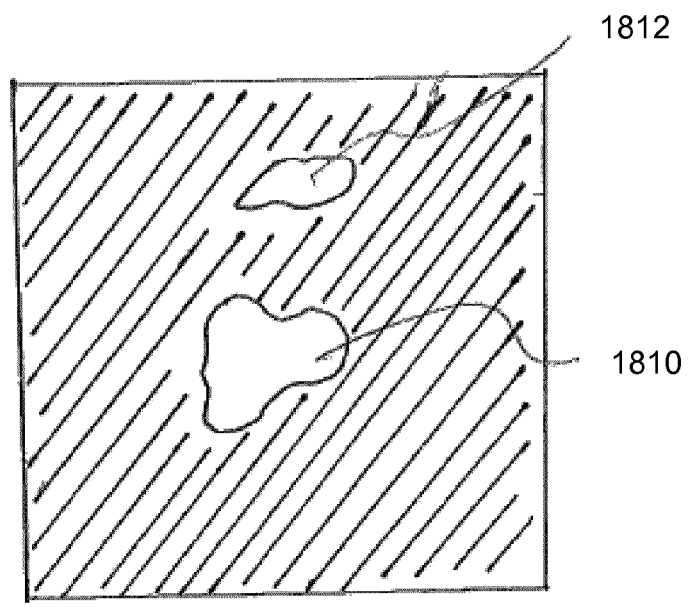
FIG. 18 shows a dynamic DRR generated from the same assumed schematic planning CT according to an example as described in Annex A.

In step S24 the dynamic DRRs are determined by considering the trajectory similarity values during DRR generation from the planning CT. As mentioned above, the consideration can be performed by modifying the absorption properties (Hounsfield values) described by the image values of the planning CT in dependence on the trajectory similarity value assigned to the corresponding image element. For instance assume, the trajectory similarity values related to anatomical elements represented by regions 1822, 1824, 1826, and 1828 are below a threshold, then for example the image values for these regions are set to black as shown in FIG. 18.

Figure 13:
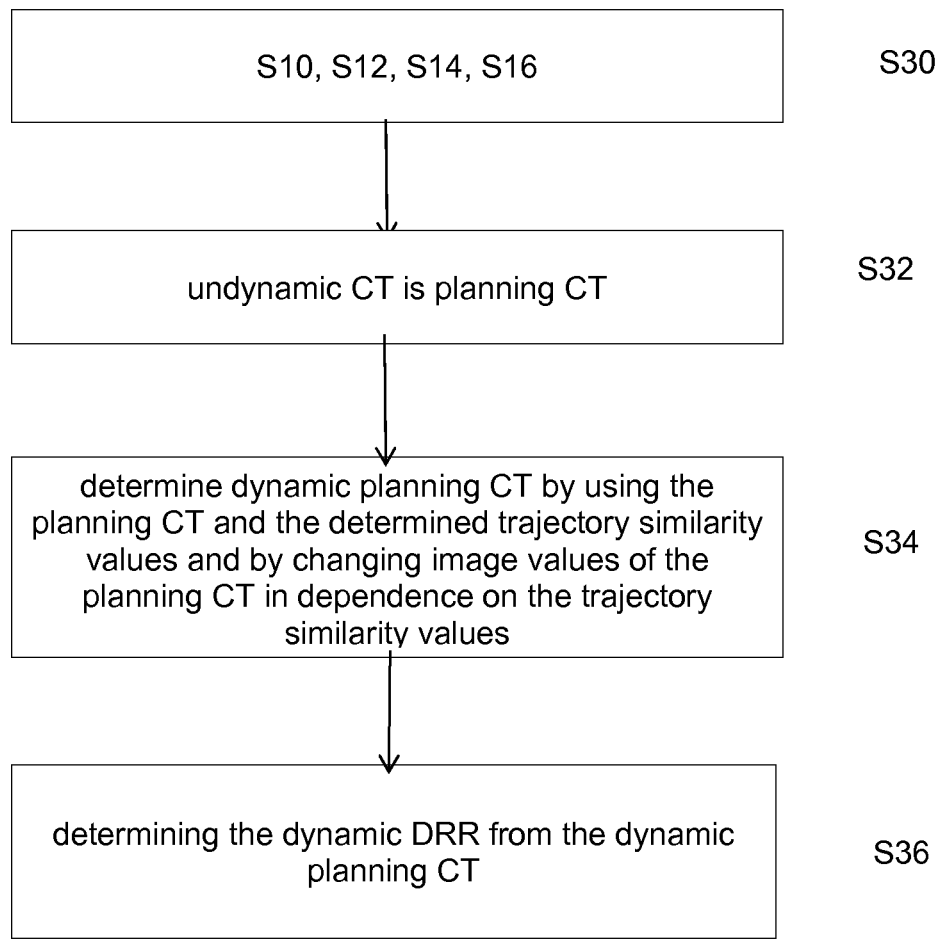
FIG. 13 shows a flowchart according to one exemplary embodiment according to at least one exemplary embodiment for determining dynamic DRRs as described in Annex A.

FIG. 13 is a further flowchart which represents at least one further exemplary embodiment.

The steps S30 and S32 correspond to steps S20 and S22 in FIG. 12 and can be interchanged or performed simultaneously.

According to step S34, the dynamic planning CT is determined by using the planning CT and the determined trajectory similarity values and by changing the image values of the planning CT in dependence on the trajectory similarity values. For example, the image values of the planning CTs represent Hounsfield values which are a measure for the interaction of the corresponding anatomical body part represented by the image value with the x-rays. By changing the image values of the planning CT in dependence on the trajectory similarity value, the subsequent determination of the dynamic DRR is influenced. This determination is performed in step S36. The dynamic DRR is performed in the usual manner of generating a DRR but not based on a usual planning CT but on the dynamic planning CT determined in step S34.

Figure 14:
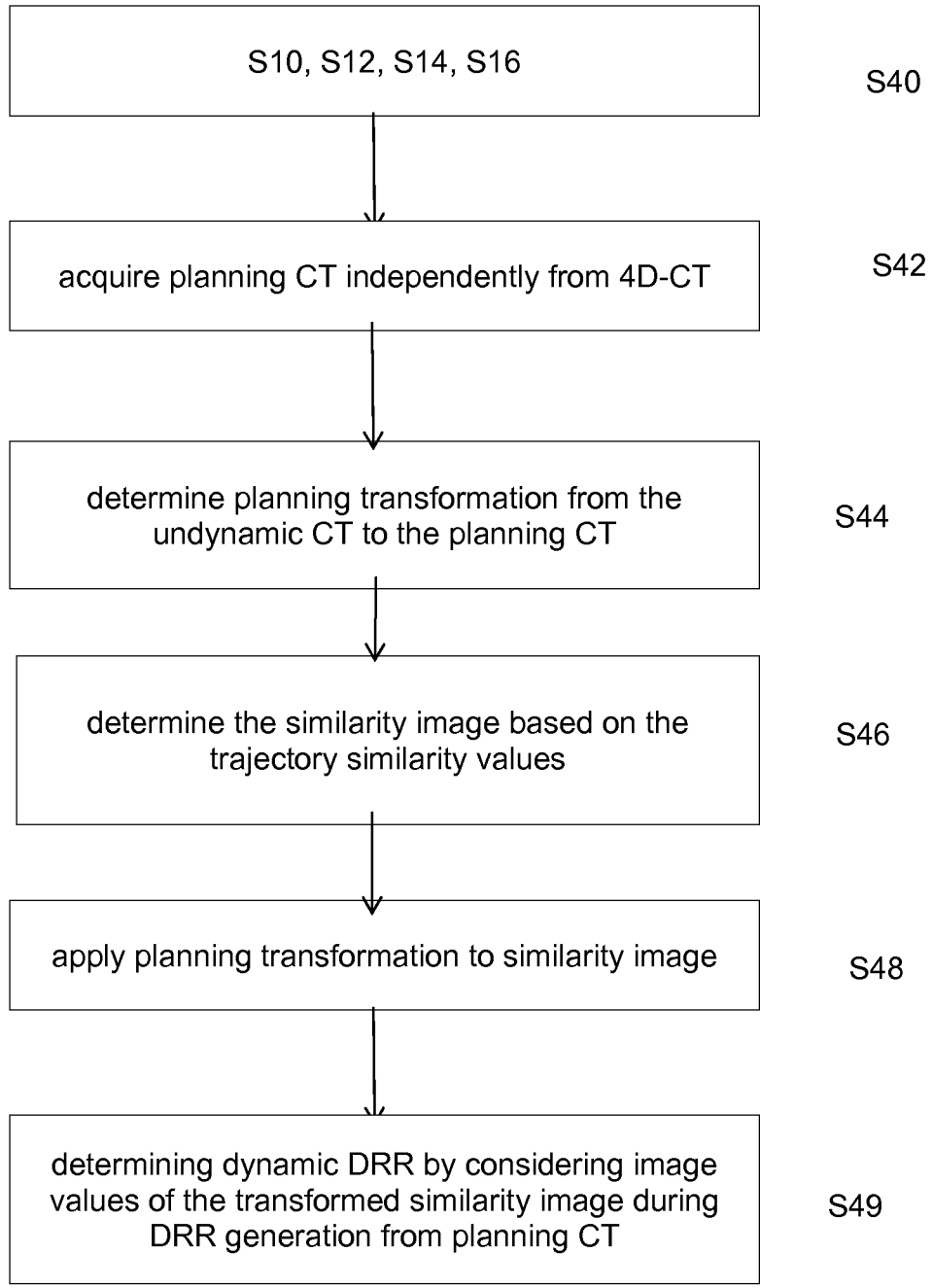
FIG. 14 shows a flowchart according to one exemplary embodiment according to at least one exemplary embodiment for determining dynamic DRRs as described in Annex A.

According to the at least one exemplary embodiment shown in FIG. 14, there is first the step S40 which corresponds to the combination of steps shown in FIG. 11. Before, after or simultaneously this step, a step S42 is performed for acquiring a planning CT independently from the 4D-CT. This step is step S42. Based on the undynamic CT determined in step S40, a planning transformation is determined from the undynamic CT to the planning CT for instance by using image fusion. This is done in step S42.

The step S46 can be performed before S42 or step S44 or simultaneously thereto, for example. The step S46 uses the trajectory similarity values determined in step S40 to determine the similarity image explained above.

According to step S48, the planning transformation determined in step S44 is applied to the similarity image.

According to step S49, the dynamic DRR is determined by considering image values of the transformed similarity image during DRR generation from the planning CT. The "consideration of image values" is performed in the same manner as described above with respect to the generation from the planning CT in step S24.

Figure 15:
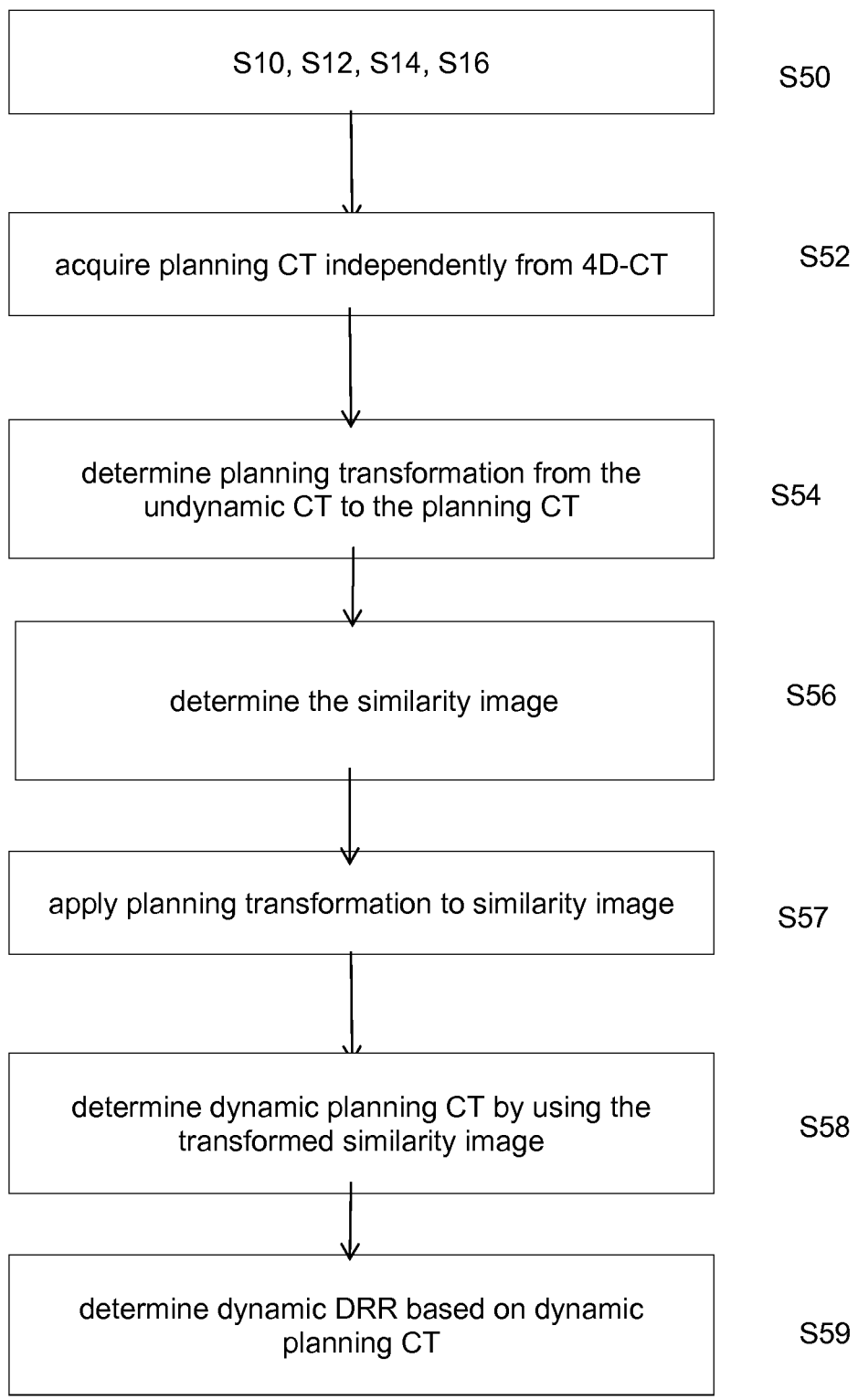
FIG. 15 shows a flowchart according to one exemplary embodiment according to at least one exemplary embodiment for determining dynamic DRRs as described in Annex A.

According to the at least one exemplary embodiment shown in FIG. 15, which is an exemplary flowchart, a step S50 is performed, which comprises the steps of the FIG. 11.

For example, a step S52 is performed, which relates to the acquisition of the planning CT independently from the 4D-CT. That is, the patient is for instance before or after the generation of the 4D-CT subjected to medical image generation by means of an analytical device for generating a CT. According to at least one exemplary embodiment, the planning CT is static and not time dependent.

According to the step S54, a planning transformation is determined from the undynamic CT to the planning CT. For example, this is performed in the manner as described before with respect to step S44.

According to step S56, the similarity image is determined by using the trajectory similarity values determined in step S50. For example, the step S56 is performed before or after step S54 or before or after step S52 or simultaneously to one of those steps.

According to step S57, the planning transformation is applied to the similarity image for determining a transformed similarity image.

For example according to a further step S58, the dynamic planning CT is determined by using the transformed similarity image. That is, the trajectory similarity values of image elements of the similarity image are used to modify image values of corresponding image elements of the planning CT. "corresponding image elements" are image elements which are at the same position in the planning CT as corresponding image elements in the similarity image.

For example, in a step S59, the dynamic DRR is determined based on the dynamic planning CT by applying usual methods known in the art for determining a DRR from a CT.

Figure 16:
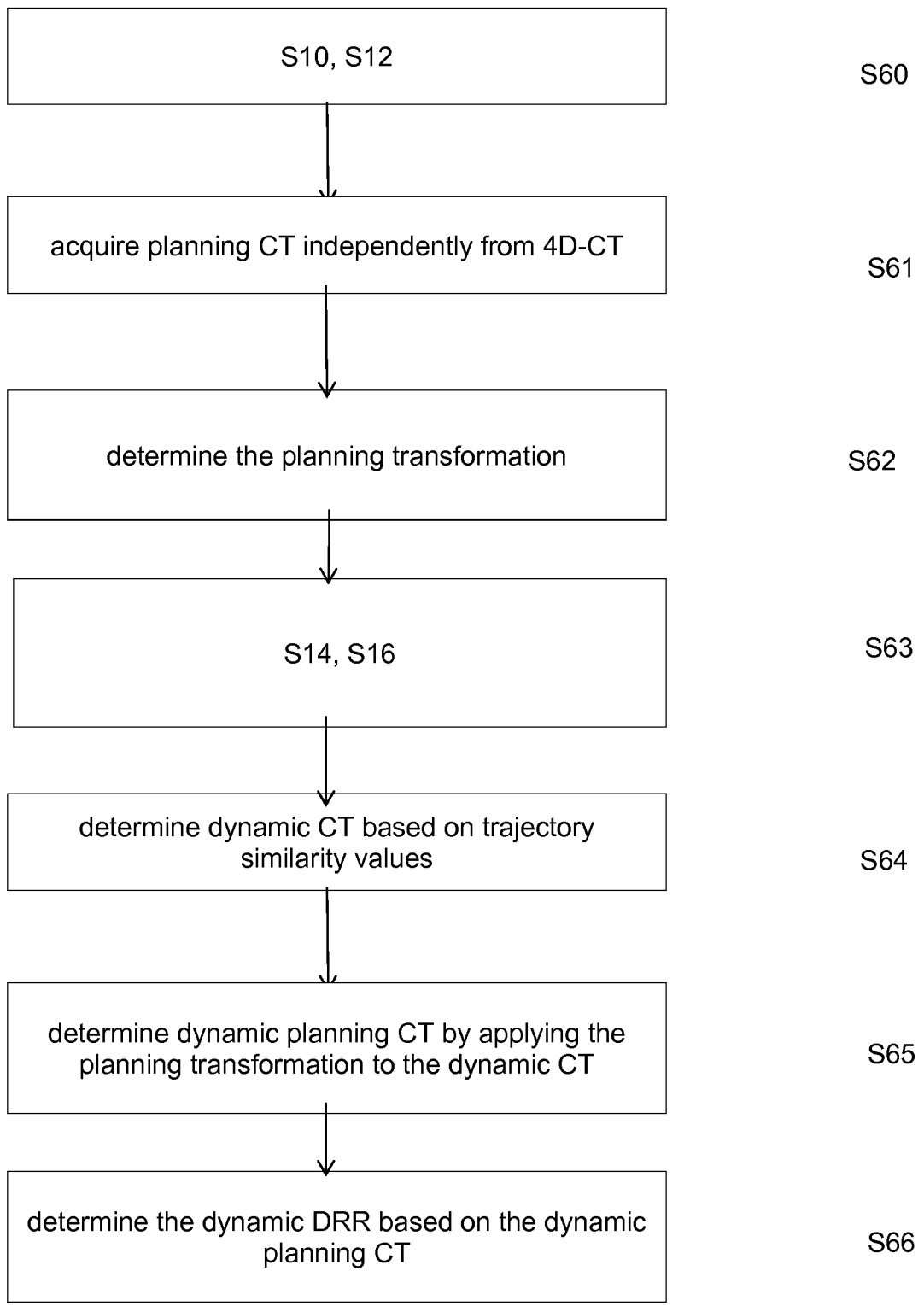
FIG. 16 shows a flowchart according to one exemplary embodiment according to at least one exemplary embodiment for determining dynamic DRRs as described in Annex A.

According to at least one further exemplary embodiment, a flowchart shown in FIG. 16 describes method steps of the at least one further exemplary embodiment. According to step S60, the steps S10 and S12 are performed. According to step S61 the planning CT is acquired independently from a 4D-CT as described above with respect to step S42 or step S52. For example, the step S60 is performed before, after or simultaneously to step S61 or S62.

For example, according to step S62, the planning transformation is determined based on the undynamic CT and the planning CT.

For example in a step S63, the steps S14 and S16 of FIG. 11 are performed for determining the trajectory similarity values. For example, the determined trajectory similarity values are used in step S64 to determine the dynamic CT. The dynamic CT is a three-dimensional image which is for example determined by changing image values of the undynamic CT. The change is performed based on the trajectory similarity values determined in step S63. For example, in step S63 the trajectory similarity values are determined for particular image elements of the undynamic CT. That is, the trajectory similarity values are assigned to the respective image elements. The assigned trajectory similarity values are then used to change the image values of image elements of the undynamic CT in step S64. For example, this is at least done for at least a part of the second image elements. For example, this is done in case the trajectory similarity values are below a predetermined threshold.

For example, according to another step S65, the dynamic planning CT is determined by applying the planning transformation to the dynamic CT.

For example, according to a step S66, the dynamic DRR is determined based on the dynamic planning CT in a manner which is usual for determining a DRR from a CT.

FIG. 17 has already been described above.

FIG. 18 represents a schematic and exemplary example of a dynamic DRR. It is assumed that the region 1810 represents the treatment body part (for instance tumor). FIG. 18 represents a region which has been generated from the planning CT. The region represents the DRR projection of a voxel cluster. The trajectory similarity values assigned to the voxel cluster are above a predetermined threshold value. That is, the region 1812 represents a body part which undergoes a similar vital movement as the treatment body part 1810. The term "similar" covers herein identical and the usual meaning of "similar". For example, image values related to trajectory similarity values above a predetermined threshold remain unchanged are not influence by the trajectory similarity values, and remain for example unchanged during determination of the dynamic DRR. In FIG. 18, the regions 1822, 1824, 1826 and 1828 are missing since the trajectory similarity values relating to those regions are below a predetermined threshold value. According to an exemplary alternative embodiment, the trajectory similarity value is a value which represents the result of application of the threshold function. That is, the trajectory similarity value is for example a binary value which is for example zero for "non-similarity" and one for "similarity". That is, in this exemplary embodiment, the trajectory similarity values for the voxel clusters which represent the regions 1822, 1824, 1826 and 1828 in the planning CT are related to trajectory similarity values which indicate non-similarity (for example having a value of 0).

Figure 19:
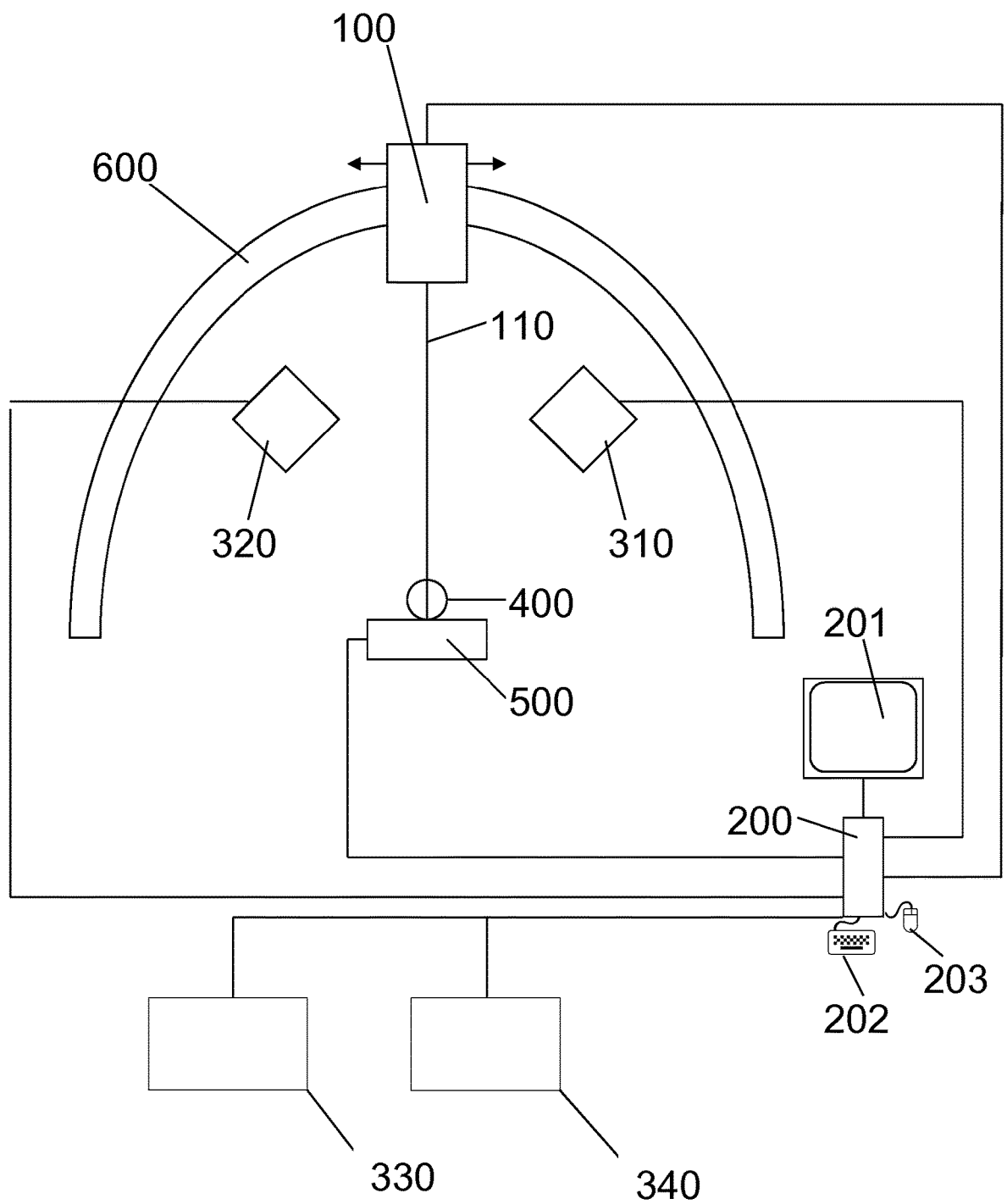
FIG. 19 shows a system according to at least one exemplary embodiment as described in Annex A.

FIG. 19 shows at least one exemplary embodiment according to an aspect of Annex A which is related to a system. The system comprises for example a computer 200. To the computer 200 is connected a monitor 201, a keyboard 202, and a mouse 203, for example. For example, the computer 200 is connected to the treatment device 100 constituted to emit a treatment beam 110 and which can, for example, be moved along an arc 600. For example, x-ray devices 310 and 320 are used to make a two-dimensional x-ray image from a patient 400 which is placed on a couch 500. Alternatively or additionally, the computer 200 can be connected to the couch 500 for changing the position of the couch 500. Alternatively or additionally, the computer 200 can be connected to an analytical device 330 for generating the 4D-CT. Additionally or alternatively, the computer 200 can be connected to the analytical device 340 for generating the planning CT. The connections described above are for example constituted to transfer image data. The connection can be wired or wireless.

Exemplary Steps of at Least One Example

According to an example, the different points in time assigned to respective sequence CTs referred to different breathing states of a patient. For example, the respective sequence CTs are assigned to 100% inhaled, 25% exhaled, 50% exhaled, 75% exhaled, 0% inhaled, 25% inhaled, 50% inhaled, 75% inhaled.

For example, one of the sequence CTs, to which a particular point in time (for instance particular respiratory state) is assigned, is selected as the undynamic CT. The selection is for instance performed as described in WO 2015/127970. That is, that one of the sequence CTs is selected as undynamic CT, in which the target is good discernible.

For example, in order to determine the primary and secondary trajectories, image fusion (for example elastic fusion) is performed for the different points in time (respiratory states).

For example, the undynamic CT acts as a source for the calculation of the trajectories. For example, elastic fusion mapping is used to get a first image element (target point) at a certain point in time (for instance certain phase of respiration) for every first image element of the undynamic image. For example, the image elements are voxels or cluster of voxels.

For example, the trajectory is defined by means of the image elements at different points in time. For example a trajectory is mathematically defined by T, then T={source point, target point (10%), target point (20%), . . . , target point (90%)}.

For example, the points of the trajectory describe positions of three-dimensional image elements for a particular point in time, for example of voxels or cluster of voxels. For example, the trajectory is a sorted list of the points. For example, the points are sorted by time (for example phase, for example phase of respiration).

Examples for calculating a measure of similarity for the trajectories is given in the following.

First example of calculation of a similarity measure is based on a sum of squared differences.

In the following, the abbreviation "SSD" stands for sum of squared differences. The abbreviations X, Y, Z stand for the coordinates of a three-dimensional coordination system within which the trajectory is described. The latter $T_1$ stands for example for a trajectory of a treatment body part, for example of an isocenter of the treatment body part or of center of mass of a treatment body part. That is $T_{1x}(i)$ is the x coordinate of the treatment body part at the time (for instance phase) "i". $\overline{T}_{1x}$ is the average x coordinate of the treatment body part averaged over all points in time (for example all states of respiration). Correspondingly, $T_{2x}$ stands for the x coordinate of an image element (for example voxel) of the undynamic CT at the point in time (i) and $\overline{T}_{2x}$ stands for the average x coordinate of this image element averaged over the different points in time (for example states of respiration). The calculation is for example as follows:

$$SSDX = \sum_{i=1}^{n} ((T_{1x}(i) - \overline{T}_{1x}) - (T_{2x}(i) - \overline{T}_{2x}))^2$$

$$SSDY = \sum_{i=1}^{n} ((T_{1y}(i) - \overline{T}_{1y}) - (T_{2y}(i) - \overline{T}_{2y}))^2$$

$$SSDZ = \sum_{i=1}^{n} ((T_{1z}(i) - \overline{T}_{1z}) - (T_{2z}(i) - \overline{T}_{2z}))^2$$

$$SSD_{XYZ} = \frac{w_x * SSDX + w_y * SSDY + w_z * SSDZ}{w_x + w_y + w_z}$$

The above equations represent an approach to compute a measure of similarity of trajectories based on sum of squared differences. $SSD_{XYZ}$ is an example for a trajectory similarity value or the result of applying a threshold function to $SSD_{XYZ}$ is an example for a trajectory similarity value.

According to another example, correlation and amplitude correspondence are determined separately for determining the measure of similarity. For example, as described below, the correlation and the amplitude correspondence can be mixed, after separate determination in order to determine a trajectory similarity value as a measure of similarity or can respectively be used as a measure of similarity.

According to an example, a normalized correlation coefficient is calculated as follows:

For all three dimensions x,y,z the correlation coefficient is computed separately and the average correlation coefficient is taken as final measure. One could also think about weighting the correlation coefficients e.g. if a tumor is moving with diaphragm I-S correlation coefficient y (I/S) should get more weight. The equations below describe computing the normalized correlation coefficient for x,y,z, and the combination to be taken as a trajectory similarity value. $T_1$ and $T_2$ have the meaning as described above, and n is the number of points of each trajectory.

$$CCX = \frac{\sum_{i=1}^{n}(T_{1x}(i) - \overline{T}_{1x}) - (T_{2x}(i) - \overline{T}_{2x})}{\sum_{i=1}^{n}(T_{1x}(i) - \overline{T}_{1x})^2 \sum_{i=1}^{n}(T_{2x}(i) - \overline{T}_{2x})^2}$$

$$CCY = \frac{\sum_{i=1}^{n}(T_{1y}(i) - \overline{T}_{1y}) - (T_{2y}(i) - \overline{T}_{2y})}{\sum_{i=1}^{n}(T_{1y}(i) - \overline{T}_{1y})^2 \sum_{i=1}^{n}(T_{2y}(i) - \overline{T}_{2y})^2}$$

-continued $$CCZ = \frac{\sum_{i=1}^{n}(T_{1z}(i) - \overline{T}_{1z}) - (T_{2z}(i) - \overline{T}_{2z})}{\sum_{i=1}^{n}(T_{1z}(i) - \overline{T}_{1z})^2 \sum_{i=1}^{n}(T_{2z}(i) - \overline{T}_{2z})^2}$$

$$CC_{XYZ} = \frac{w_x * CCX + w_y * CCY + w_z * CCZ}{w_x + w_y + w_z}$$

The above equations represent an example for an approached compute a similarity measure for describing the similarity between trajectories based on correlation coefficient. The abbreviation "CC" stands for correlation coefficient. $CC_{XYZ}$ is an example for a trajectory similarity value or the result of applying a threshold function to $CC_{XYZ}$ is an example for a trajectory similarity value.

To determine a trajectory similarity value, a correlation coefficient can be combined with a value which describes similarity of amplitude of trajectories. An exemplary approach is described below:

For correlation coefficients that exceed a certain threshold (e.g. 0.7) one could add a second threshold focusing on the amplitude. The more accordance in the absolute value of the value, the higher the value. Here an exemplary equation focusing on the main direction of the target, in this case inferior-superior (I-S), the breathing motion caused by the diaphragm.

$$A_{IS} = \frac{\text{Min}(A_1, A_2)}{\text{Max}(A_1, A_2)}$$

In the above equation $A_1$ describes the peak to peak amplitude of a trajectory of the treatment body parts (for example isocenter or center of mass of treatment body part). For example the amplitude is along a particular axis of the coordinate system or a long one of the axis described for instance by a rotational ellipsoidal. $A_2$ describes the corresponding peak to peak amplitude of an image element of the undynamic CT. The terms "Min" and "Max" stand for the function of determining the minimum respectively the maximum of $A_1$ and $A_2$.

According to a further embodiment, the threshold value of the above described threshold function is changed in dependence on the similarity of amplitudes which is for example described by $A_{IS}$. $A_{IS}$ is an example for an amplitude similarity value. As described above, the planning CT can be one of the sequence CTs (for example bins) of the 4D-CT or can be generated separately. In the following, examples for this are described.

A scenario is that the Planning CT is one of the bins of the 4DCT scan. Then, for example, the dynamic image is not registered to the treatment volume, that is the planning transformation is not performed. (Remark: A 4DCT scan consists of several volumes/bins, each volume/bin corresponding to a specific respiratory state. Typical labeling: 100% Inhaled, 25% Exhaled, 25% Exhaled, 75% Exhaled, 0% Inhaled, 25% Inhaled, 25% Inhaled, 75% Inhaled).

In case the Planning CT is not part of the 4DCT scan, the planning CT is registered to one of the sequence CTs (by using the planning transformation). The registration procedure and thus the determination of the planning transformation would mean for example a first rigid registration step (concentrating e.g. on bones) yielding a transformation that brings the two in a common coordinates system, followed by a second deformable registration yielding a second transformation which represents a deformation field. The combination of the first and second transformation represents an example for a planning transformation. The question which one of the sequence CTs to be used as undynamic CT:

If the planning CT was taken during a specific breathing phase one could register the planning CT to the sequence CT which corresponds to the same respiratory state.

One could also register consecutively to all sequence CTs, and select the most similar sequence CT as the undynamic CT. 'Most similar' could for instance mean selecting the registration that resulted in the fewest deformation around the target area.

Or as mentioned above, one could select that one of the sequence CTs in which the treatment body part is best discernable.

Or a combination of the above.

According to an example, the computer implemented method is constituted to display the dynamic DRRs in dependence on selected thresholds. In particular, the computer implemented method can be constituted that a user changes the threshold while getting immediate feedback of the effect of change of threshold by displaying the dynamic DRR. In more detail, this is for example as follows:

The computer implemented method can be constituted to display a page for defining the dynamic DRR. This page provides e.g. a slider enabling the user to set a certain threshold value used by the above described threshold function. A first page can show a very strict threshold resulting in a dynamic DRR nearly containing the treatment body part (target) only. Only voxels following exactly the same trajectory (normalized) are taken into account for rendering. In another page, the threshold can be decreased and thus more voxels—voxels whose trajectory is "very similar" to the target—are used for rendering the dynamic DRR.

With respect to the Figures showing flowcharts, generally, the sequence of the steps is not obligatory but just an example. The only requirement is that data necessary for a determination step have to be acquired before the respective determination.

Different Aspects According to Annex A

According to a first aspect, a computer implemented method for determining a two dimensional DRR is disclosed referred to as dynamic DRR based on a 4D-CT, the 4D-CT describing a sequence of three dimensional medical computer tomographic images of an anatomical body part of a patient, the images being referred to as sequence CTs, the 4D-CT representing the anatomical body part at different points in time, the anatomical body part comprising at least one primary anatomical element and secondary anatomical elements, the computer implemented method comprising the following steps:

acquiring (S10) the 4D-CT;

acquiring (S22, S32, S52, S61) a planning CT, the planning CT being a three dimensional image used for planning of a treatment of the patient, the planning CT being acquired based on at least one of the sequence CTs or independently from the 4D-CT, acquiring (S12) a three dimensional image, referred to as undynamic CT, from the 4D-CT, the undynamic CT comprising at least one first image element representing the at least one primary anatomical element and second image elements representing the secondary anatomical elements;

acquiring (S14) at least one trajectory, referred to as primary trajectory, based on the 4D-CT, the at least one primary trajectory describing a path of the at least one first image element as a function of time;

acquiring (S14) trajectories of the second image elements, referred to as secondary trajectories, based on the 4D-CT;

for the image elements of the undynamic CT, determining (S16) trajectory similarity values based on the at least one primary trajectory and the secondary trajectories, the trajectory similarity values respectively describing a measure of similarity between a respective one of the secondary trajectories and the at least one primary trajectory;

determining (S24, S36, S49, S59, S66) the dynamic DRR by using the determined trajectory similarity values, and, in case the planning CT is acquired independently from the 4D-CT, further using a transformation referred to as planning transformation from the undynamic CT to the planning CT, at least a part of image values of image elements of the dynamic DRR being determined by using the trajectory similarity values.

According to a second aspect, the computer implemented method according to aspect 1 is disclosed, wherein image values of image elements of the dynamic DRR are determined in dependence on the trajectory similarity values used for determining the image elements.

According to a third aspect, the computer implemented method according to one of the preceding aspects is disclosed, wherein the undynamic CT is the planning CT (S22, S32); and wherein the step of determining the dynamic DRR comprises at least one of the following steps a) or b):

a) determining (S24) the dynamic DRR by using the planning CT and the determined trajectory similarity values, wherein, during determination of the dynamic DRR from the planning CT, the trajectory similarity values are considered; or b) determining (S34) another three dimensional image, referred to as dynamic planning CT by using the planning CT and by changing image values of the planning CT in dependence on the trajectory similarity values, and determining (S36) the dynamic DRR by digitally reconstructing the two-dimensional image from the dynamic planning CT.

According to a fourth aspect, the computer implemented method according to one of the aspects 1 to 3 is disclosed, wherein the step of acquiring (S42, S52) the planning CT independently from the 4D-CT is performed and further comprising the steps of:

determining (S44, S54) the planning transformation;

acquiring (S46, S56) a three dimensional image referred to as similarity image from the determined trajectory similarity values related to the image elements of the undynamic CT;

applying (S48, S57) the planning transformation to the similarity image;

wherein the step of determining the dynamic DRR comprises at least one of the following steps a) or b):

a) determining (S49) the dynamic DRR by using the planning CT and the determined trajectory similarity values, wherein, during determination of the dynamic DRR from the planning CT, image values of the transformed similarity image are considered; or b) determining (S58) another three dimensional image, referred to as dynamic planning CT by changing image values of the planning CT in dependence on the corresponding trajectory similarity values of the transformed similarity image and determining (S59) the dynamic DRR by digitally reconstructing the two-dimensional image from the dynamic planning CT.

According to a fifth aspect, the computer implemented method according to one of aspects 1 to 3 is disclosed, wherein the step of acquiring (S61) the planning CT independently from the 4D-CT is performed and further comprising the steps of:
  determining (S62) the planning transformation; and
  wherein the step of determining the dynamic DRR comprises:
    determining (S64) a three dimensional image, referred to as dynamic CT by changing image values of at least a part of at least the second image elements of the undynamic CT in dependence on the trajectory similarity values determined for the respective image elements;
    determining (S65) a three dimensional image referred to as dynamic planning CT by applying the planning transformation to the dynamic CT; and
    determining (S66) the dynamic DRR by digitally reconstructing the two-dimensional image from the dynamic planning CT.

According to a sixth aspect, the computer implemented method according to one of the preceding aspects is disclosed wherein
  the step of acquiring the primary and secondary trajectories comprises:
    acquiring at least the at least one first image element from the undynamic CT;
    acquiring the second image elements from the undynamic CT;
    determining transformations referred to as sequence transformations which are constituted to transform the undynamic CT to one or more of the sequence CTs and/or to transform one of the sequence CTs to another one of the sequence CTs;
    determining the trajectories of the at least one first image element and of at least some of the second image elements by applying the determined sequence transformation to the at least one first image element and the at least some of the second image elements.

According to a seventh aspect, the computer implemented method according to one of the preceding aspects is disclosed, comprising a step of calculating trajectory similarity values as a measure of similarity between trajectories, the step comprising one of the following:
  a) determining the respective trajectory similarity values as a function of positional differences between a first position of the at least one first image element defined by the at least one primary trajectory for different points in times and an average of the first position for the different points in time and a positional difference between a second position of a respective one of the second image elements defined by the secondary trajectory for the different times and an average of the second position for the different points in time,
  b) determining correlation coefficients describing a correlation between the trajectories
  c) determining a normalized correlation describing a normalized correlation between the trajectories
  d) determining amplitudes of the trajectories
  e) a combination of one of steps a) to c) with d)

According to an eighth aspect, the computer implemented method of one of the preceding aspects is disclosed, wherein an anatomic atlas is used according to at least one of the following steps:
  at least one of the second image elements are determined by means of segmentation using the anatomic atlas; or
  for one or more of the second image elements no trajectories are determined in dependence on the result of the segmentation achieved by means of the anatomic atlas; or
  trajectory similarity values related to one or more of the second image elements are determined in dependence on the result of the determination.

According to a ninth aspect, the computer implemented method according to one of the preceding aspects is disclosed comprising a display of a superposition of the dynamic DDR over a two-dimensional X-ray image and/or aside the two-dimensional X-ray image.

According to a tenth aspect, a computer implemented method for determining a three dimensional image referred to as similarity based on a 4D-CT is disclosed and/or for determining a two-dimensional DRR referred to as dynamic DRR and/or for determining a three-dimensional image referred to as dynamic CT, the 4D-CT describing a sequence of three dimensional medical computer tomographic images of an anatomical body part of a patient which represent the anatomical body part at different points in time, the images being referred to as sequence CTs, the anatomical body part comprising at least one primary anatomical element and secondary anatomical elements, the computer implemented method comprising the following steps:
  acquiring the 4D-CT;
  acquiring a three dimensional image, referred to as undynamic CT, from the 4D-CT, the undynamic CT comprising at least one first image element representing the at least one primary anatomical element and second image elements representing the secondary anatomical elements;
  acquiring at least one trajectory, referred to as primary trajectory, based on 4D-CT, the at least one primary trajectory describing a path of the at least one first image element as a function of time;
  acquiring trajectories of the second image elements, referred to as secondary trajectories, based on the 4D-CT;
  for the image elements of the undynamic CT, determining trajectory similarity values based on the primary trajectory and the secondary trajectories, the trajectory similarity values respectively describing a measure of similarity between a respective one of the secondary trajectories and the at least one primary trajectory; and
  further comprising at least one of the following steps:
    a) determining the similarity image by determining the trajectory similarity values to be image values of image elements of the similarity image, referred to as similarity image elements; and
    optionally displaying the similarity image; or
    b) determining the dynamic DRR by using the determined trajectory similarity values, at least a part of image values of image elements of the dynamic DRR being determined by using the trajectory similarity values; and optionally displaying the dynamic DRR; or
    c) determining the dynamic CT by changing image values of at least a part of at least the second image elements of the undynamic CT in dependence on the trajectory similarity values determined for respective image elements and optionally displaying the dynamic CT.

According to a eleventh aspect, the computer implemented method of the tenth aspect is disclosed, comprising the step of acquiring a planning CT, the planning CT being a three dimensional image used for planning of a treatment of the patient, the planning CT being acquired based on at least one of the sequence CTs or independently from the 4D-CT; and
- the positions of the similarity image elements correspond to the positions of the image elements of the undynamic CT to which the trajectory similarity values are respectively related;
- and optionally, in case the planning CT is acquired independently from the 4D-CT, further determining a transformation from the undynamic CT to the planning CT and applying the transformation to the similarity image before displaying the similarity image.

According to a twelfth aspect, a program is disclosed which, when running on a computer or when loaded into a computer, causes the computer to perform the method according to any one of the preceding aspects and/or to and/or a signal wave, in particular a digital signal wave, carrying information which represents the program, in particular, the aforementioned program in particular comprises code means adapted to perform all the steps of the method of one of the preceding aspects.

According to a thirteenth aspect, a computer-readable program storage medium on which the program according to the twelfth aspect is stored, for example in a non-transitory manner.

According to a fourteenth aspect, a computer is disclosed, the computer comprising the compute-readable program storage medium of the thirteenth aspect.

According to a fifteenth aspect, a system is disclosed, comprising:
- the computer (200) of the preceding aspect; and at least one of the following:
  - a) a display device (201) for displaying the dynamic DRR and an interface for receiving the 4D-CT; or
  - b) a couch (500) for placing a patient (400) and a treatment device (100) constituted to emit a treatment beam; or
  - c) an analytical device (310, 320) constituted for generating two-dimensional x-ray images;
  - d) an analytical device (330) constituted for generating the 4D-CT; or
  - e) an analytical device (340) constituted for generating the planning CT.

Annex B

Annex B relates to a dynamic anatomic atlas comprising static atlas data and dynamic atlas data. It also relates to a computer implemented data processing method comprising the step of acquiring the dynamic anatomic atlas, a method for generating the dynamic anatomic atlas and a use of the dynamic anatomic atlas. It also relates to a computer program, a non-transitory computer-readable storage medium and a computer.

Physiologic movements like vital movements, conscious and unconscious movements and others as well as other time-dependent physical properties have not been considered within a known anatomical atlas. The term "vital movement" means that the body parts are moved by vital functions of the body such as respiration and/or heartbeat. These functions of the body sustain life. Conscious movements can be consciously controlled, i.e. muscle movements, for example to move a limb. Unconscious movements are movements which cannot be controlled by will, i.e. the heartbeat. Other physiologic movements for example include movements of body fluids such as the blood. Examples of other time-dependent properties include for example the change of temperature, the change of pressure and the change of concentration of a given substance.

One idea underlying Annex B is the integration of dynamic information described by dynamic atlas data (for example the information gained using physiologic volume rendering as disclosed in PCT/EP2016/053291 (as described in Annex A) into an anatomic atlas. According to PCT/EP2016/053291 (as described in Annex A), via elastic fusion—of a reference bin of a 4D CT to the remaining bins—for every voxel a trajectory is computed which describes a time-dependent change of position of the individual pixel. Each trajectory can then be correlated to other trajectories, for example to find out what structures move in a similar way as a target structure such as a tumor. The result can subsequently be displayed as a "heatmap" indicating the degree of similarity of movement of each voxel to a target structure, for example based on the determined correlations.

The dynamic atlas data (e.g. general trajectory, and movement correlation) of certain areas or structures obtained in this way shall be stored in an anatomical atlas, for example as meta data. This enables the analysis of newly acquired individual timely resolved patient image data (e.g. 4D CT data) using this dynamic information described by the dynamic atlas data.

Aspects of Annex B, examples and exemplary steps and their embodiments are disclosed in the following. Different exemplary features of Annex B can be combined wherever technically expedient and feasible.

In the following, a short description of the specific features of Annex B is given which shall not be understood to limit Annex B only to the features or a combination of the features described in this section.

A dynamic anatomic atlas is disclosed. Compared to a static anatomic atlas, this atlas comprises further dynamic atlas data. This dynamic atlas data describes time-dependent physical properties of the atlas segments (for example movement of the atlas segments or a correlation of movement of different atlas segments).

The dynamic anatomic atlas can be generated based on 3D image data enriched with dynamic data, referred to as dynamic DRR, dynamic CT or similarity image (see Annex A). The dynamic CT is for example generated based on a 4D CT. The dynamic CTs of a plurality of patients are each matched with static atlas image data. The dynamic data of a matched patient segment (contained in the dynamic CT of the patient) is transferred to the corresponding atlas segment (enrichment of static atlas with dynamic the data). Since a plurality of patients should be used to generate the atlas, a normalization of the dynamic data should be performed.

The dynamic anatomic atlas can be used to classify a patient into a patient category (age, sex, type of disease etc.) depending on the movement of patient segments. Also, structures in a patient which cannot be identified as critical in static patient images but which move abnormally compared to the atlas can be determined, e.g. non-enhancing lung tumors which are attached to a rib. Furthermore, the dynamic data can be used to divide static atlas segments into subsegments which move differently from each other (e.g. subdivision of lung into a plurality of segments), thereby increasing the accuracy of results obtainable using the anatomic atlas.

In the following, a description of the general features of Annex B is given for example by referring to possible embodiments of Annex B.

The method, the program and the system are defined by the below aspects. Advantages, advantageous features, advantageous embodiments and advantageous aspects of Annex B are disclosed in the following and contained in the subject-matter of the dependent aspects. Different advantageous features can be combined in accordance with Annex B wherever technically expedient and feasible. Specifically, a feature of one embodiment which has the same or a similar function to another feature of another embodiment can be exchanged with said other feature, and a feature of one embodiment which adds an additional function to another embodiment can for example be added to said other embodiment.

Annex B relates to a dynamic anatomic atlas. The dynamic anatomical atlas may be stored as data in a storage device such as a non-transitory storage medium. The dynamic anatomic atlas for example is an atlas which can be used in a way similar to that of an anatomical atlas. This type of atlas is for example described in the chapter "Definitions". The anatomical atlas can for example be an anatomical atlas referred to as "universal anatomical atlas", generated for example described in the chapter "Definitions" below and used for example as described in the chapter "Definitions" below. The dynamic anatomical atlas for example includes information on a dynamic property as will be described below, therefore being referred to as dynamic anatomical atlas.

The dynamic anatomical atlas for example comprises static atlas data. The static atlas data may be data comprised in an anatomical atlas as described in the chapter "Definitions". For example, the static atlas data describes the static position of at least one object, for example of at least one atlas segment.

The static atlas data for example describes a plurality of atlas segments. For example, the atlas segments represent anatomical body parts. The static atlas data may include information about at least one static property of the plurality of atlas segments such as for example a physical property such as at least one of the geometry (shape and/or size, volume, length, height, diameter etc.), position, (optical or physical) density and temperature of each of the atlas segments and pressure, flux (e.g. flow direction, flow rate, flow rate distribution, . . . ), and concentration of a substance (e.g. oxygen) within each of the atlas segments.

For the generation of the static atlas data, the geometry of a segment can for example be measured in medical images, using hardware measurement tools such as rulers or using common imaging methods such as digital images of a patient. The position can for example be determined in the same way. The optical density of an anatomic segment can be measured using medical images obtained by transmission imaging methods such as X-ray imaging. The physical density of an anatomic segment can also be measured by such methods but also using commonly available hardness measurement methods and tools (pressure-measurement, indentation measurement, elasticity measurement etc.). The temperature can for example be measured using a thermometer, a thermocamera, thermoresistive surgical tools or else. The pressure can be measured using pressure sensors or by determining the deformation of an anatomical region of which the elasticity module is known. The concentration of a substance may be detected using a chemical concentration sensor such as a ph-meter or using medical imaging methods such as functional MRT (fMRT). The flux can also be measured using medical imaging methods such as (4D)CT, (4D)fMRT, medical ultrasound (such as Doppler sonography), flow rate meters or else.

The dynamic anatomical atlas for example further comprises dynamic atlas data. The dynamic atlas data is for example stored as meta data.

The dynamic atlas data for example comprises information on a dynamic property. The dynamic property for example describes a (time-dependent) change of a physical property of an atlas segment. The dynamic property is for example at least one of the change of geometry (shape and/or size, volume, length, height, diameter etc.), position, (optical or physical) density and temperature of each of the atlas segments and the change of pressure and concentration of a substance within each of the atlas segments. The dynamic atlas data for example comprises information on at least one dynamic property, for example information on a plurality of dynamic properties, for example different types of dynamic properties.

The dynamic properties may be measured in a way similar to the measurement of the physical property described above for the static atlas data. Dynamic properties like temperature changes or changes in the concentration of oxygen in different segments may be determined by measuring a time dependent response of a patients' body to a change, like a stimulus, e.g. local and/or external temperature change, application of medication, physical exhaustion etc. The dynamic property may be described as a trajectory, for example a trajectory describing the time-dependent movement of a segment or a trajectory in a plane which is defined by two different physical properties such as temperature and density.

The information on the dynamic property for example is respectively linked to the atlas segments. For example, this information is included in dynamic atlas data which is stored as meta data associated with the atlas segments. Alternatively or additionally, this information is stored separately from the static atlas data and linked to the static atlas data using links such as hyperlinks or a table including linking information, i.e. associating each of the information on the dynamic property to individual atlas segments. "Respectively" in this context means that the information on the dynamic property is linked to individual atlas segments, meaning that an individual atlas segment is associated with individual information on the dynamic property.

For example, for an individual atlas segment, there is a bijective relationship between the static data related to this atlas segment and the dynamic data related to this atlas segment. For example, this bijectively linked relationship is given for some or for each single one of the individual atlas segments. For example, the link and the storage of the static and dynamic atlas data is such that, for an individual atlas segment (for example for each one thereof), both the dynamic data and the static data or only one thereof is extractable and further processable. This allows for instance the calculation of correlation of movements. The extraction is for example directly possible without performing an image analysis or an analysis of a sequence of images due to the storage of the dynamic data separately from but linked with the static data. "Separately" means for example at different storage locations (e.g. storage sections, for instance a header of a file) and that both information types (dynamic and static) are separated in different files and/or storage locations. For instance, the header of the file describes dynamic data and the file describes static data.

For example, this association is performed upon creating or improving the dynamic anatomic atlas as will be described below. The meaning that "information on a dynamic property is linked to an atlas segment" or "information on a dynamic property is linked to at least one of a plurality of atlas segments" is meant to cover for example the following: First information on a first dynamic property and optionally second information on a second dynamic property is respectively linked to a respective one of the atlas segments. This is meant to also cover the case where this link is performed not just for the respective one of the atlas segments but also for a plurality or all of the atlas segments. For example, a plurality of information on a plurality of (different) dynamic properties is respectively linked to the respective atlas segments. That is, it should be noted that although singular form may be used in the claims and the description, this formulation also includes the meaning of "at least one", for example a plural, i.e. in case the claims refer to a singular entity, they may well include a plurality of the entity.

The information on the dynamic property for example describes correlations between the dynamic properties of different ones of the atlas segments. For example, the information on the first dynamic property of a first atlas segment describes a correlation between the first dynamic property of the first atlas segment and the first dynamic property of a second atlas segment. Each correlation for example describes a correlation between the (same, in the example "first") dynamic properties of two individual and different atlas segments. In this case, for example, the information on the first dynamic property of a first atlas segment describes a plurality of correlations between the first dynamic property of the first atlas segment and the first dynamic properties of a plurality of other atlas segments, for example all other atlas segments. Furthermore "plurality of correlations" means that each one of the plurality of correlations describes a correlation between the first dynamic property of the first atlas segment and the first dynamic property of one of the plurality of other atlas segments. If there is more than one dynamic property, the term "first" can be replaced by "second", "third" and so on depending on the number of dynamic properties. The correlations may be stored in form of a matrix, an array or else and may for example be stored as meta data associated with the static atlas data describing the first atlas segment or stored as described above. For instance, each entry in a first one of a plurality of lines of the 2D matrix describes one correlation to one other atlas segment with respect to a first dynamic property and the entries in a second line of the matrix do the same for a second dynamic property and so on.

The correlations, for example in the form of a matrix, can for example be averaged and/or normalized between different individuals (for example patients) and/or between different atlas segments. For example, the information on the dynamic property describes correlations between the dynamic properties of a plurality of different ones of the atlas segments, for example all different ones of the atlas segments. The information on the dynamic property described above for a first anatomic atlas segment for example is determined (and for example stored in the dynamic anatomic atlas) for a plurality of atlas segments or for each of the atlas segments. The correlation may be determined upon creating or improving the dynamic anatomical atlas as will be described below.

As a correlation, for example the cross correlation between two trajectories of different atlas segments P and Q is used. In this example, each trajectory may describe the position of an atlas segment depending on time. The trajectory may be generated by connecting (and for example by interpolating) several positions of the atlas segment which differ from one another depending on time. For example, the positions are connected in a sequence corresponding to the point in time in ascending timely order. Interpolation might be used to smooth the connecting line of the positions and/or fill in voids (missing data points).

Of course, also other time-dependent physical properties are possible which can be described as vectors $\vec{p}(t)$, $\vec{q}(t)$ (e.g. deformation or temperature change). A plurality of such vectors may define the aforementioned trajectory. For example, values of two separate parameters x, y at a point in time t can be described by a vector $\vec{p}_{x,y}(t)$ which defines values x(t) and y(t). Several of these vectors $\vec{p}(t)$ may define a trajectory representing time-dependent changes of the values of the parameters x and y—in this case, the trajectory may lie in a plane defined by the first parameter x (e.g. temperature) and the second parameter y (e.g. blood flow rate), wherein each point of the trajectory indicates an amount of the first parameter x and an amount of the second parameter y at a given point in time.

The first parameter x may describe the position in a first spatial direction, whereas the second parameter y may describe the position in a second spatial direction. A third parameter z may describe the position in a third spatial direction. In this case, a vector $\vec{p}_{x,y,z}(t)$ for example describes time-dependent values x(t) of the first, time-dependent values y(t) of the second and time-dependent values of the third parameter. Several of these vectors $\vec{p}_{x,y,z}(t)$ for different points in time $t_0, t_1, \ldots, t_n$ can be combined, forming a trajectory in four dimensions (3 spatial and 1 time dimension). As noted above, the trajectory can be interpolated for smoothing and for filling in voids (missing data points).

A trajectory can for example be described by global vectors including all values of the vector $\vec{p}(t)$ (e.g. $\vec{p}_{x,y}(t)$ or $\vec{p}_{x,y,z}(t)$) at several points in time (e.g. all point in time for which data is available). For example, the global vector $\vec{p}_{glob}$ comprises all vectors $\vec{p}_{x,y,z}(t)$ for (n+1) points in time: $\vec{p}_{x,y,z}(t_0), \vec{p}_{x,y,z}(t_1), \ldots, \vec{p}_{x,y,z}(t)(t_n)$. For example, all vector values are stored in the global vector as follows:

$$\vec{p}_{glob} = \{p_x(t_0), p_y(t_0), p_z(t_0), p_x(t_1), p_y(t_1), p_z(t_1), \ldots, p_x(t_n), p_y(t_n), p_z(t_n)\}.$$

For the generation of the dynamic anatomic atlas (see below), only closed trajectories might be used which alternatively or additionally exhibit a periodic temporal behavior. For example, the dynamic property is dynamic spatial information in the form of at least one trajectory, for example in case the dynamic spatial information comprises information on a change of position of an atlas segment and/or information on a change of geometry of an atlas segment.

To determine the correlation between two trajectories, for example a global vector $\vec{p}_{glob}$ describing the respective trajectory can be used. For example, a global vector $\vec{p}_{glob,1}$ describing a first trajectory and a global vector $\vec{p}_{glob,2}$ describing a second trajectory can be used to determine the correlation between the first and the second trajectory. The correlation between the first trajectory described by all values of $\vec{p}(t)$ and the second trajectory described by all values of $\vec{q}(t)$ can for example be determined as follows:

$$\text{Corr} = \frac{\int_{t=t_0}^{t=t_n} (\vec{p}(t) - \vec{p}(t_0))(\vec{q}(t) - \vec{q}(t_0)) dt}{\sqrt{\int_{t=t_0}^{t=t_n} (\vec{p}(t) - \vec{p}(t_0))(\vec{p}(t) - \vec{p}(t_0)) dt} \sqrt{\int_{t=t_0}^{t=t_n} (\vec{q}(t) - \vec{q}(t_0))(\vec{q}(t) - \vec{q}(t_0)) dt}}.$$

Alternatively or additionally, a component-wise or weighted correlation may be used. For example, all correlations between all trajectories ($\vec{p}(t)$, $\vec{q}(t)$, $\vec{r}(t)$, $\vec{s}(t)$, ...) of different atlas segments (P, Q, R, S, ...) are calculated as a matrix (CM).

The direction Dir of each trajectory, for example of the trajectory described by all values of $\vec{p}(t)$ of atlas segment P, can also be calculated, for example as follows:

$$Dir = \frac{\vec{p}(t) - \vec{p}(t_0)}{\sqrt{\int_{t=t_0}^{t=t_n} (\vec{p}(t) - \vec{p}(t_0))(\vec{p}(t) - \vec{p}(t_0)) dt}}$$

or $$Dir = \frac{\vec{p}(t_0)}{|\vec{p}(t_0)|}.$$

The direction Dir can for example be averaged and/or normalized and associated to and/or stored for the corresponding atlas segment. The direction Dir may not be a scalar and may therefore for example be back-transformed into the dynamic anatomical atlas before averaging and/or normalizing.

As noted above, the information on the dynamic property for example describes correlations between the dynamic properties of different ones of the atlas segments. The dynamic properties of different ones of the atlas segments may include a plurality of different types of dynamic properties. For example, the information on the dynamic property for example describes correlations between the dynamic properties of different ones of the atlas segments The information on the dynamic property for example describes at least one normalized dynamic property of at least one atlas segment. For example, the dynamic property of some or all atlas segments is normalized between some or all of the atlas segments, for example so that the dynamic property of some or all of the atlas segments can be compared with the dynamic property of some or all atlas segments. For example, the dynamic property of all atlas segments is normalized between all atlas segments. For example, the dynamic property of some of the atlas segments is normalized between all atlas segments. For example, the dynamic property of some of the atlas segments is normalized between the some of the atlas segments.

Alternatively or additionally, the dynamic property of some or all atlas segments is normalized between different individuals, wherein information of the different individuals was used for creating and/or improving the dynamic anatomic atlas as will be described below. For example, the dynamic property of patient segments of a first group (class) of patients is normalized with respect to a common reference. As the common reference, a predetermined value and/or trajectory and/or vector and/or else of the dynamic property can be used. Alternatively or additionally, as the common reference, a certain patient segment of each of the patients is used (e.g. a rib). In this example, the common reference is different among patients or patient groups (classes). For example, trajectories of a first patient segment of all patients of a certain patient type (class) are normalized with respect to a common reference trajectory or parts thereof. For example, a maximum value of the common reference trajectory and/or a minimum value of the common reference trajectory are used as normalization values. For example, the trajectories of the first patient segment of all patients of the certain type (class) are adjusted so as to have the same minimum and/or maximum values as defined by the normalization values. For example, at least one of the maximum and minimum values of the trajectories in a certain spatial direction may be used as the maximum and minimum values. Of course, other methods are possible for normalization. The normalization is e.g. performed to make the individual dynamic properties of different patients comparable with each other.

Normalization of other dynamic properties can for example be performed using a common reference as well. The common reference may be a predetermined vector and/or matrix and/or value(s) or may be the change of the physical property of a certain patient segment or part thereof, i.e. the change of temperature, flux or geometry. For example, the dynamic properties associated with several voxels are averaged to serve as a common reference.

The term normalization in this disclosure does not relate to the reduction of data to a kind of canonical form but relates to the normalization of values, vectors, matrices and/or trajectories. For the correlation and normalization of trajectories describing time-dependent movement, reference is also made to Annex A.

The at least one dynamic property linked to an atlas segment is for example classified according to patient types. The patient types for example include one or more of patients with a certain disease, patients with a certain age, patients with a certain anatomical property (obese, missing organs, deformed organs etc.), patients with a certain gender or else. For example, the at least one dynamic property linked to an atlas segment is classified according to patient types depending on information of individuals from different patient types, for example information on the at least one dynamic property of an anatomic body part of individuals from different patient types, for example the individuals from different patient types used upon creating and/or improving the dynamic anatomic atlas.

For example, information on the dynamic property of first anatomical body parts of individuals of a certain age are determined upon creating and/or improving the dynamic anatomic atlas. The certain age is then for example associated with the information on the dynamic property of the first anatomical body parts. In case this information is used upon creating and/or improving the dynamic anatomic atlas, the at least one dynamic property linked to an atlas segment is classified according to the patient type of the certain age.

The dynamic anatomic atlas for example comprises information on a distribution of at least one dynamic property. The distribution of the at least one dynamic property may describe a probability of a value or values of the at least one dynamic property. For example, the distribution describes a probability of a value of the at least one dynamic property for a certain patient type. For example, the distribution describes a value or values of the at least one dynamic property for healthy patients, for example a value of probability of a correlation between two trajectories of two anatomic body parts of a healthy patient. In this example, if the value of correlation between two trajectories of two anatomic body parts of a patient with a disease deviates from the value of correlation between the two trajectories of the two corresponding anatomic body parts of the healthy patient, the information on a distribution of the dynamic property can be used as an indicator whether the patient with a disease has a disease. In this example, it can be determined that the patient with a disease has a disease if the value of correlation between two trajectories of the two anatomic body parts of the patient with a disease has a probability for healthy patients below a certain threshold, which probability is described by the distribution of the dynamic property. The distribution may be determined upon creating and/or improving the dynamic anatomic atlas.

The distribution of at least one dynamic property may describe different probabilities of a value of the at least one dynamic property for different patient types (patient classes). The classification according to patient types mentioned earlier can be used therefore. For example, a first dynamical property linked to a first anatomic atlas segment is classified into a first patient type and a second dynamical property linked to the first atlas segment is classified into a second patient type. This means that a first and a second dynamic property are linked to the one atlas segment, wherein these dynamic properties are classified into different patient types. As a consequence, there may be one dynamic property respectively linked to a first anatomic atlas segment for each one of the patient classes. This may also be the case for a plurality of for all of the atlas segments.

For example, a first patient class representing healthy patients and a second patient class representing patients with lung cancer can be provided. As noted earlier, a dynamic property can be assigned to each of these classes. For example, the movement of lung parts or the diaphragm can be classified according to patient types. The information on a distribution of the at least one dynamic property, for example the movement of the lung parts or the diaphragm, can be used to further increase an error rate of classifying a patient into one of the patient classes based on the dynamic anatomic atlas. As noted above, a dynamic property of a patient can be compared with the distribution. Depending on the result of the comparison (i.e. exceed a certain probability threshold), the patient can be assigned to the correct patient class which works as an indicator for a disease of the patient. The distribution gives more reliable results than fixes values because not all patients in one patient class may exhibit the same amount of dynamic property, for example the same amount of movement of the lung parts. The distribution can therefore be used as a measure of probability of a patient to fall into one of the patient categories.

The dynamic anatomic atlas for example comprises an atlas segment subdivided into atlas subsegments respectively linked with different dynamic properties while exhibiting the same segment representation information. For example, the different dynamic properties are of the same type of dynamic property but represent different values of the same type of dynamic property. For example, the atlas segment is subdivided into two atlas subsegments of the same tissue type (e.g. which have the same visual appearance in medical image data) or which exhibit the same segment representation information (which is for example stored associated with the static atlas data), wherein a first of the two atlas subsegments is respectively linked with a first value and a second of the two atlas subsegments is respectively linked with a second value of the same dynamic property. Different types of the dynamic property for example include movement, deformation, temperature change, pressure change or others as noted above.

Annex B also relates to a computer implemented data processing method comprising the step of acquiring the dynamic anatomic atlas.

Annex B also relates to a computer implemented data processing method for generating (e.g. improving or generating from the scratch) the dynamic anatomic atlas. The method for example comprises a step of acquiring, based on the static atlas data, a static atlas image of the atlas segments. For example, a 3D static atlas image such as a 3D CT or 3D MR image is generated based on the static atlas data. For example, a 2D static atlas image such as a 2D DRR image is generated based on the static atlas data. The generated static atlas image represents one or more of the atlas segments. Other medical image data may be generated as the static atlas image. For example, the static atlas image is generated taking into account a viewing angle of an imaging device used to obtain a static patient image, for example for the generation of the 2D DRR.

For example, the method further comprises a step of acquiring static patient data describing a static patient image of a patient segment. The static patient data may be medical image data, for example 3D CT image data, 3D MR image data, 2D X-ray image data or else. The static patient data may further include information on physical parameters such as temperature, concentration of a substance, pressure or else, for example in a locally-resolved manner. The static patient image may be an image of one or more patient segments. The patient segment for example is an anatomical body part of the patient and/or a part of the patient with a similar tissue structure which is for example represented by the same intensity and/or gray value in an X-ray image. As noted below, the acquisition may comprise loading of the static patient data, for example from a storage medium. The static patient data may be obtained beforehand, i.e. the obtaining of the static patient data, for example using a medical imaging device, is for example not part of the method.

The method for example further comprises a step of acquiring information on a dynamic property. The dynamic property is for example at least of the change of a physical property, like geometry, position, (optical or physical) density, temperature and volume of the patient segment and the change of pressure and concentration of a substance within a patient segment. The information for example is respectively linked to the patient segment. The patient segment for example is an anatomical body part of the patient, for example a segmented part in the static patient image, for example an anatomical body part having a certain tissue structure. The term "respectively" means that individual information on the dynamic property is linked to an individual patient segment, for example different information on the dynamic property is linked to each of a plurality or all of the patient segments. For example, the information on the dynamic property is obtained from dynamic 3D data and/or a similarity image and/or a dynamic DRR as described which are described in detail in Annex A and respectively linked to different patient segments.

The method for example further includes a step of matching the static patient image with the static atlas image. The matching for example matches one or more of the patient segments included in the static patient image with one or more atlas segments included in the static atlas data. The matching may comprise a step of adjusting the position of the static patient image with respect to the static atlas image, which step may be performed automatically or manually (e.g. adjustment performed by a user). For example, an automatic optimization of the position of the static patient image with respect to the static atlas image is performed. The matching may include image fusion, for example rigid and/or elastic image fusion and may be performed by a matching algorithm such as a rigid or an elastic image fusion algorithm. The matching is for example described by a transformation, for example by a transformation matrix, the transformation for example describing a transformation of a coordinate system of the static patient image to a coordinate system of the static atlas image. The coordinate system of the static patient image may be defined by the static patient data and the coordinate system of the static atlas image may be described by the static atlas data, for example as meta information included in the data.

The method may further comprise a step of determining, based on the matching, a corresponding atlas segment corresponding to the patient segment. For example, the matched static patient image is segmented using a segmentation algorithm, for example into different patient segments which for example have different tissue structures. The positions of the different segments of the matched static patient image are for example compared with positions of atlas segments of the matched static atlas image. Based on the matching, for example using the matching result, for example the transformation, and the determined position of each of the segments in the coordinate system of the static patient image and the known position of each of the atlas segments in the coordinate system of the static atlas image, and/or the segmentation results (for example the degree of similarity between the size and/or shape of the patient segments with atlas segments), a corresponding atlas segment is determined which corresponds to the patient segment. This determination may be performed for a plurality of patient segments included in the static patient image.

The method may further comprise a step for generating (improving or creating from the scratch) the dynamic anatomic atlas. This step for example comprises determining, based on the information on the dynamic property linked to the patient segment, the information on the dynamic property linked to the corresponding atlas segment. For example, the information on the dynamic property is newly linked to the corresponding atlas segment and/or the already linked information on the dynamic property is updated (e.g. averaged and/or overwritten). As a consequence of this step, information on the dynamic property is respectively linked to the corresponding atlas segment. This step can be performed for at least one atlas segment, for example a plurality of atlas segments, using a plurality of corresponding patient segments and the information on the dynamic property respectively linked to the plurality of patient segments. In other words, dynamic information of a patient is used to enrich the anatomic atlas comprising static atlas data so that it comprises static and dynamic atlas data as described above.

For example, data of multiple (for example classified, see above) patients may be used in this process to generate the dynamic anatomic atlas. For example, the information on the dynamic property of an atlas segment (which is for example classified according to patient types) may be determined as an average (value) of information on the dynamic property of the corresponding patient segment of a plurality of patients (for example a plurality of patients of a particular patient type).

For this purpose, one or more of an average, a weighted average, a median, a mean or a distribution of the (value(s) of) information on the dynamic property may be determined based on the information on the dynamic property respectively linked to the corresponding patient segment of each one of the plurality of patients. Alternatively or additionally, the information on the dynamic property respectively linked to the corresponding patient segment may be normalized before being stored or before being used as information on the dynamic property respectively linked to the atlas segment or before being determined as information on the dynamic property respectively linked to the atlas segment. The normalization may be performed as described above, for example using reference information, for example information on the dynamic property respectively linked to a reference structure of the patient.

Instead of acquiring the patient images, an anatomic atlas comprising several static atlas images describing physical properties (positions, temperature, pressure, concentration of a substance etc.) of the atlas segments at different points in time may be used. For example, the several static atlas images can be used to determine the trajectories and thereafter the correlations. In this case, no additional patient images are necessary. In other words, the patient image data can be replaced with atlas image data in case the atlas image data describes physical properties of the atlas segments at different points in time. With respect to such an atlas comprising static atlas images, which can for example be a universal atlas, it is referred to the chapter "Definitions".

The method for example comprises a step of calculating correlations between the dynamic properties of different patient segments based on the information on the dynamic properties linked to different patient segments for determining the correlations between the dynamic properties of different ones of the atlas segments described by the information on the dynamic property respectively linked to the atlas segments. These correlations as well as the calculation thereof have been described above. For example, correlations between the dynamic property of a first patient segment to dynamic properties (of the same type) of different patient segments are calculated. These correlations are thereafter determined as the correlations between the dynamic properties of the corresponding atlas segment (corresponding to the first patient segment) and the different corresponding atlas segments (corresponding to the different patient segments). The correlations are for example set and/or stored so as to be described by the information on the dynamic property respectively linked to the corresponding atlas segment. Consequently, a plurality of correlations may be stored for the corresponding atlas segment. This determination may be performed for a plurality or all off the patient segments to generate the dynamic atlas data comprised in the dynamic anatomic atlas.

Alternatively or additionally, based on at least the information on the dynamic property linked to a patient segment at least one normalized dynamic property for the patient segment is calculated for determining the at least one normalized dynamic property described above. For example, the dynamic property of some or all of the patient segments is normalized between some or all of the patient segments. The some of the patient segments are for example segments in a predetermined anatomical region (e.g. lung, abdomen, region defined by a predetermined distance from a reference segment, . . . ) and/or segments which are influenced by the same physical mechanism (e.g. heartbeat, breathing motion, conscious movement, . . . ) which segments can be chosen based on first predetermined selection criteria and/or segments which are known to have comparable dynamic physical properties (e.g. movement in a certain direction to a certain degree (movement amount below threshold), same cyclic phase of movement (same time constant of cyclic movement), same cyclic phase of change of other physical properties such as concentration of a substance, flow rate, temperature change and others, . . . ) which segments can be chosen based on second predetermined criteria. Alternatively or additionally, the dynamic property of some or all of the patient segments is normalized between different patients. Alternatively or additionally, the dynamic property of some or all of the patient segments is normalized with respect to a reference structure.

For example, a reference structure is identified in each of a plurality of patients which is used as a normalization reference, wherein static patient data and dynamic patient data of each one of the plurality of patients is used to generate the dynamic anatomic atlas. As described above, the information on dynamic properties of patient segments of different patients can be averaged, weighted averaged or else to determine the information on dynamic properties of corresponding atlas segments. The reference structure is for example identified in each of the patients which (static and dynamic) information are used to generate the dynamic anatomic atlas. The reference structure may differ amongst patient classes (for example amongst patient types).

For example, in case the dynamic property is dynamic spatial information in the form of at least one trajectory, a reference object with a reference trajectory is identified in each of the different individuals, for example a reference anatomical body part, for example a rib. The trajectories of other anatomical body parts are for example normalized for each of the different individuals using the individual reference trajectory (which may be different for each of the plurality of patients). Several normalization methods may be used for normalization. For example, a maximum and/or a minimum and/or average (e.g. mode, mean, median, weighted average) value of the reference trajectory are used as a reference for normalization, for example a maximum and/or minimum and/or average value of the reference trajectory in a particular direction (e.g. along the main axis or along a sub axis). For example, only closed loop trajectories, for example only cyclic (timely cyclic) trajectories are normalized. For example, the main axis (the amount of positional shift in the main axis) of a reference trajectory may be used to normalize one or more of the patient trajectories.

The normalization may be performed for patients of different patient types (classes) independently and/or differently. For example, the trajectories of patients of a first type (class) are normalized with respect to a first reference whilst the trajectories of patients of a second type (class) are normalized with respect to a second reference. For example, the first patient type defines patients with lung cancer whereas the second patient type defines healthy patients. For example, the first patient class defines patients who are older than a predetermined age, whereas the second patient class defines patients who are younger than the predetermined age.

The normalization may be performed for each patient individually. For example, the trajectories of each of the patients are normalized with respect to an individual reference. For example, the individual reference is a trajectory of a certain patient segment of the individual patient (e.g. the rib). For example, the individual reference is a reference which serves as an indicator of a certain movement such as a breathing movement, a heartbeat or else. Since these movements (e.g. breathing movement) may affect other anatomic body parts of a patient (e.g. lung is displaced by breathing movement), the individual reference serving as an indicator of the movement (e.g. a rib) can be used for normalization of the trajectories of the other body parts (e.g. the lung) with respect to the movement (e.g. the breathing movement). This results in trajectories which are normalized with respect to a certain type of movement. That can for example make several trajectories of different patients which have all been normalized with respect to the same kind of movement (e.g. breathing movement) comparable, independent on the exact amount of movement which might differ greatly between patients (e.g. older patients breath less air per breathing cycle than mid-aged patients). With respect to the trajectories and the calculations based on these trajectories (normalization, correlation etc.), it is also referred to Annex A.

Alternatively or additionally, the information on the dynamic property of the plurality of patients may be normalized using a common reference such as a predetermined reference which is for example independent of each of the patients. For example, a predetermined multiplication (and/or division and/or addition and/or subtraction) factor (and/or vector or matrix) is used to normalize the information on the dynamic property of each of the plurality of patients.

Also, at least one threshold value may be used to determine which of the information on the dynamic property of the patient segments of the plurality of patients shall be used to generate the dynamic anatomic atlas. For example, information on the dynamic property exceeding a certain threshold may not be used for generating the dynamic anatomic atlas. For example, only closed loop movements (e.g. (timely cyclic) closed loop trajectories) are used for generating the dynamic atlas data.

The method for example comprises a step of determining atlas subsegments corresponding to the dynamic subregions, based on subregions exhibiting different dynamic properties. The different dynamic properties are for example a dynamic property of the same type, i.e. the different dynamic properties are different dynamic characteristics, e.g. values, directions or vectors of a certain dynamic property (e.g. different temperatures or different direction of the main axis of a cyclic trajectory). For example, certain patient segments may comprise dynamic subregions exhibiting different characteristics of a dynamic property. In this case, the certain patient segments are for example subsegmented into a plurality of patient subsegments, wherein each subsegment exhibits a different dynamic property. The "different dynamic property" may correspond to a certain range of values of the dynamic property.

Similarly to the method described above with respect to the atlas segments, the information on the dynamic property of each patient subsegment may be used to determine the information on the dynamic property of each corresponding atlas subsegment. For example, the method comprises a step for generating (improving or creating from the scratch) the dynamic anatomic atlas by determining, based on the information on the dynamic property linked to the patient subsegments, the information on the dynamic property linked to the corresponding atlas subsegments. For example, the same information on the dynamic property is linked to several patient subsegments, i.e. depending on the resolution of the measurement method used to determine the information on the dynamic property. For example, several patient subsegments may correspond to the same atlas subsegment or vice versa. In this case, the information on the dynamic property of the several patient subsegments may be combined (e.g. averaged (weighted, mode, mean, . . . )) to determine the information on the dynamic property of the corresponding atlas subsegment or the information on the dynamic property of the patient subsegment may be determined as the information on the dynamic property of the corresponding several atlas subsegments.

Annex B also relates to a computer implemented data processing method for enabling an analysis of an anatomic dynamic of a patient. For example, the method comprises several steps as described above with reference to the method for generating the dynamic anatomic atlas: a step of acquiring the static atlas data and the dynamic atlas data of the dynamic atlas, wherein the static atlas data describes a static atlas image; a step of acquiring static patient data describing a static patient image of a patient segment; a step of acquiring dynamic patient data comprising information on a dynamic property which information is respectively linked to the patient segment; a step of matching the static patient image with the static atlas image; and a step of determining a corresponding atlas segment corresponding to the patient segment based on the matching.

For enabling the analysis, the method comprises an additional step. This step for example includes comparing the information on the dynamic property linked to the corresponding atlas segment and the information on the dynamic property linked to the patient segment. For example, the comparing includes calculating a correlation between the information on the dynamic property linked to the corresponding atlas segment and the information on the dynamic property linked to the patient segment. For example, the comparing includes calculating a difference between values described by the two information. The comparing may include additional mathematical steps to compare the two information.

The method may further comprise a step of determining, based on the comparing (comparison) and based on the information on the distribution of the at least one dynamic property described above, whether the determined dynamic property of the corresponding patient segment is within a predefined range or not. The predefined range may be a range of the distribution of the at least one dynamic property, for example determined by a threshold describing a minimal probability of a certain value of the dynamic property, wherein the probability of the certain value of the dynamic property is described by the distribution.

For example, the distribution of the at least one dynamic property may describe the distribution of values of the at least one dynamic property among the plurality of patients used to generate the dynamic atlas data. In case it is determined that the determined dynamic property of the corresponding patient segment is within the predefined range it may be determined that the corresponding patient segment exhibits a normal (healthy) behavior. In case it is determined that the determined dynamic property of the corresponding patient segment is not within the predefined range it may be determined that the corresponding patient segment exhibits an abnormal (unhealthy) behavior which can indicate the presence of a disease.

The determination may be based on the classification of the at least one dynamic property. As described above, a separate distribution may be available for each of the patient types. In this example, it may be determined that the determined dynamic property of the corresponding patient segment is not within the predefined range of a first patient type (which may be healthy) but is within the predefined range of a second patient type (which may have a particular disease). This determination may be used to determine the type of the patient and at the same time whether the corresponding patient segment exhibits an abnormal (unhealthy) behavior or a normal (healthy) behavior.

The method may comprise a step of acquiring the static atlas data and the dynamic atlas data of the dynamic atlas. As a next step, the method for example includes comparing at least one dynamic property associated with a certain patient class (e.g. patient type) of the corresponding atlas segment with the dynamic property of the patient segment. This comparison may be performed as described above and for example allows to determine for which patient class there is the highest similarity for one or more patient segments.

The method may further include a step of determining the type of the patient. For example, the dynamic property associated with the certain patient class (e.g. patient type) of the atlas segments is used in this context. For example, a first degree of similarity between the dynamic property of the patient segment and the dynamic property of the corresponding atlas segment which is associated with a first patient class is determined. For example, a second degree of similarity between the dynamic property of the patient segment and the dynamic property of the corresponding atlas segment which is associated with a second patient class is determined. Depending on which degree of similarity is higher, the type of the patient can be determined. For example, in case the first degree of similarity is higher than the second degree of similarity, it is determined that the patient is classified into the first class, i.e. the patient type is a patient type corresponding to the first class.

The degree of similarity may be determined as described above with respect to the comparing, i.e. a difference in dynamic characteristics such as values and/or a correlation between values and/or trajectories or else is used as a measure of a degree of similarity. Alternatively or additionally, the aforementioned distribution may be used in this context for the assessment of similarity. For example, the dynamic property of the patient segment is compared with the distribution of the dynamic property of the corresponding atlas segment which is associated with a first patient class. This may result in a first probability of the patient segment to fall into the first patient class. For example, the dynamic property of the patient segment is then compared with the distribution of the dynamic property of the corresponding atlas segment which is associated with a second patient class. This may result in a second probability of the patient segment to fall into the second patient class. The first and the second probability may be used as a measure of similarity.

The types of a patient may for example include a type of breathing of the patient, for example indicating an amount of diaphragmatic, thoracic, clavicular and/or paradoxical breathing. The types of a patient may for example include a type of a certain pathological appearance or a type of a certain disease.

Annex B also relates to a use of the dynamic anatomic atlas for matching a patient image and an atlas image. This use for example includes a step of using the information on the dynamic property of at least one atlas segment as a constraint for the matching. For example, the matching includes an image fusion.

For example, a patient image (e.g. a static patient image comprising only static image information) may be matched with an atlas image. In this case, a constraint for the matching may be defined by the dynamic property of an atlas segment. For example, it may be defined that the corresponding patient segment must have a physical property which lies within a certain range defined by the dynamic property of the corresponding atlas segment and a predetermined range threshold. For example, the location of a possibly corresponding patient segment may be constrained to a certain area. For example, the temperature or temperature change of a possibly corresponding patient segment may be constrained to a certain range. For example, the concentration of a substance within the possibly corresponding patient segment may be constrained to a certain range. In other words, static atlas data may be used for a matching, but in this example the dynamic atlas data is used in addition to the static atlas data for the matching in the form of a constraint, e.g. a constraint limiting the possible positions of a corresponding patient segment (corresponding to a corresponding atlas segment).

For example, a patient image comprising static and dynamic information may be matched with an atlas image. In this case, a constraint for the matching may be that a certain atlas structure to be matched with the patient image exhibits a certain dynamic property which the corresponding patient structure must also exhibit to a predetermined degree or to which the corresponding patient structure must not be in contradiction thereto.

For instance the dynamic property may describe a maximal change of geometry and/or position of a segment in absolute terms or relative to other segments (e.g. maximum distance to another segment during positional change caused by vital movements), which should not be violated by the image fusion. For example, in case the information on the dynamic property respectively linked to an atlas structure representing a rib describes a movement of max. 5 cm in z-direction a constraint for the matching may be that the corresponding patient structure is allowed to move max. 4-6 cm in z-direction which movement may be described by the information on the dynamic property respectively linked to the corresponding patient segment.

Alternatively or additionally only atlas structures exhibiting a certain degree of dynamic property such as a certain amount of movement are used for matching the patient image with an atlas image. For example, the atlas structure which exhibit the least amount of movement (indicated by the information on the dynamic property respectively linked to the atlas segments) are used for the matching.

For example, the dynamic anatomic atlas is used for matching two patient images (with one another). To this end, the matching is for example coupled (coupled transformation) by means of the atlas as described in the chapter "Definitions", in particular in the aspects 1) to 10). For example, the information on the dynamic property of at least one atlas segment is used as a constraint for the matching of the two patient images. For example, the first patient image is an image representing a certain patient at a first point in time, whereas the second patient image is an image representing the certain patient at a second point in time which is different from the first point in time. For example, the second point in time is later than the first point in time. For example, each of the first and the second patient images includes at least one patient segment such as an anatomical segment (e.g. bladder). For example, at least one particular patient segment is included in both the first and the second patient image.

For example, a first patient image to be matched with a second patient image is in a first step matched with a static atlas image generated from the static atlas data of the dynamic anatomic atlas. For this matching, for example an atlas segment which information on the dynamic property indicates a low rate of movement and/or a low change in position, i.e. a dynamic property which lies below a predetermined threshold, is used (for example a vertebra which moves less than 1 mm according to the information on the dynamic property respectively linked to the vertebra as atlas segment).

For example, the corresponding patient segments (e.g. lung, bladder, ribs) and the corresponding atlas segments (e.g. lung, bladder, ribs) are identified in a second step following the first step.

For example, the two patient images (the first patient image and the second patient image) are matched in a third step following the second step. For example, the information on the dynamic property (e.g. describing movement) respectively linked to one of the corresponding atlas segments (e.g. bladder) is used as a constraint for matching the first patient image with the second patient image. For example, it can be determined that the positional difference between the corresponding patient segment in the first patient image (e.g. bladder of the patient at the first point in time) and a patient segment identified in the second image has to lie in a certain interval, for example be lower than a maximal positional deviation described by the information on the dynamic property of the corresponding patient segment. In case this condition is not fulfilled, it can for example be determined that the patient segment identified in the second patient image and used for matching the corresponding patient segment of the first patient image is not the corresponding patient segment of the second patient image (e.g. in case the patient segment identified in the second patient image is a kidney whereas the corresponding patient segment in the first patient image is the bladder). In this case, another patient segment may be identified in the second patient image to be matched with the corresponding patient segment of the first patient image (e.g. the bladder). Alternatively or additionally, a second corresponding patient segment (e.g. a kidney) of the first patient image may be determined which fulfills the constraint for the matching with respect to the patient segment of the second patient image (e.g. the kidney). Of course, other kinds of dynamic properties can be used as constraint for the matching instead of the maximal positional deviation, for example maximum and/or minimum temperature change, maximum deformation, upper and lower limit of a change in oxygen saturation or else.

The anatomic atlas can for example be used by acquiring the static atlas data and the dynamic atlas data of the dynamic atlas, the static atlas data describing a static atlas image of the atlas segments. In a next step, static patient data describing a static patient image of a patient segment may be acquired. In a next step, the static patient image may be matched with the static atlas image. A corresponding atlas segment corresponding to the patient segment may be determined based on the matching.

The use of the dynamic anatomic atlas may further comprise a step of determining subsegments within the patient segment based on the atlas subsegments of the corresponding atlas segment. For example, the position and/or shape of the corresponding atlas subsegments (corresponding to the patient segment) are determined in coordinates of the static atlas image. These coordinates may be transformed into the coordinates of the static patient image based on the matching result, i.e. based on the (matching) transformation (matrix). Subsequently, the position and/or shape of subsegments within the patient segment may be determined based on the transformed coordinates.

The dynamic property is a dynamic physical property like for example at least one of dynamic spatial information or dynamic thermodynamic information or fluid-dynamic information. The dynamic spatial information for example comprises information on a change of position (movement)

of an object (e.g. described by a trajectory) and/or information on a change of geometry (deformation) of an object. The dynamic thermodynamic information for example comprises information on a change of temperature (e.g. heating-up or cooling-down) of an object, information on a change of pressure (e.g. pressure increase or pressure decrease) of an object, information on a change of volume of an object e.g. (expansion or contraction). The fluid-dynamic information comprises for instance information on a change of flux, velocity or density (e.g. concentration) of a substance within an object (e.g. change of oxygen in brain vessel, change of flux of blood in (heart) arteries etc.). All of the aforementioned dynamic information may describe time-dependent physical properties of an object. The object is at least one of the patient segment or a subsegment thereof or one of the atlas segments or a subsegment thereof.

Annex B also relates to a computer program which, when running on at least one processor of at least one computer or when loaded into the memory of at least one computer, causes the at least one computer to perform the aforementioned method, or a signal wave, for example a digital signal wave, carrying information which represents the program. It also relates to a non-transitory computer-readable program storage medium on which the aforementioned program is stored. It also relates to least one computer, comprising at least one processor and a memory, wherein the aforementioned program is running on the at least one processor or is loaded into the memory, or wherein the at least one computer comprises the aforementioned program storage medium.

Description of FIGS. 20 to 24

Figures 20, 21:
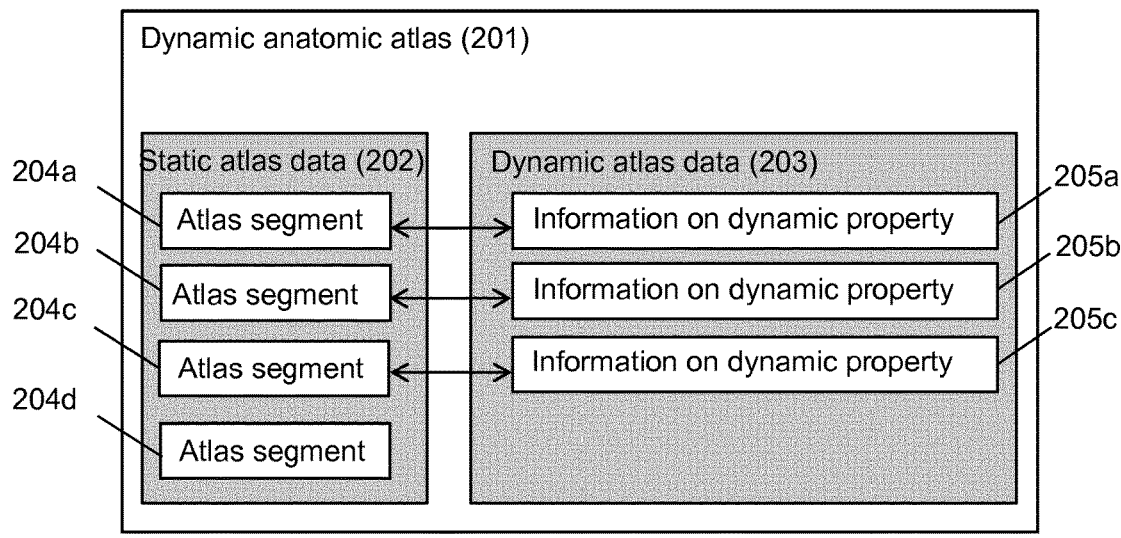
FIG. 20 is a diagram showing the basic components of the dynamic atlas as described in Annex B.
FIG. 21 is a diagram showing an example of the information on the dynamic property as described in Annex B.

FIG. 20 is a diagram showing the basic components of the dynamic anatomic atlas 201. The dynamic anatomic atlas 201 comprises static atlas data 202 and dynamic atlas data 203. The static atlas data 202 describes a plurality of atlas segments 204a, 204b, 204c, 204d whereas the dynamic atlas data 203 comprises information on a dynamic property 205a, 205b, 205c which information is respectively linked to the atlas segments 204a, 204b,204c. In the example shown in FIG. 20, four different atlas segments 204a, 204b, 204c, 204d are described by the static atlas data 202. The atlas segments 204a, 204b, 204c, 204d in this example represent a first rib, a diaphragm, a heart, and a second rib. The information on the dynamic property 205a, 205b, 205c in this example is information on the movement of an anatomical structure described by a (closed loop) trajectory. The three different information on the dynamic property 205a, 205b, 205c shown in FIG. 20 correspond to a trajectory of the atlas segment 204a (e.g. the first rib), a trajectory of the atlas segment 204b (e.g. the diaphragm) and a trajectory of the atlas segment 204c (e.g. the heart), each of which is associated with the corresponding atlas segment 204a, 204b, 204c in the dynamic anatomic atlas 201. In this example, the information on the dynamic property 205a, 205b, 205c is stored as meta data associated with the corresponding atlas segment 204a, 204b, 204c. As noted above, other and/or additional dynamical (time-dependent) physical properties may be described by the information on the dynamic property. Also, correlations between the dynamic property of a first atlas segment and the dynamic property of at least one other atlas segment may be stored as information on the dynamic property respectively linked to the first atlas segment.

In the example, there is no information on the dynamic property respectively linked to atlas segment 204d. This means that the dynamic anatomic atlas 201 shown in FIG. 20 comprises static atlas data 202 describing atlas segments (namely 204a, 204b and 204c) and dynamic atlas data 203 comprising information on a dynamic property (namely 205a, 205b and 205c) which information is respectively linked to the atlas segments (namely 204a, 204b and 204c).

FIG. 21 is a diagram showing an example of the information on the dynamic property. The example of FIG. 21 shows the information on the dynamic property 5a described by the dynamic atlas data 203, wherein the information on the dynamic property 205a is respectively linked to the atlas segment 204a described by the static atlas data 202. In this example, the information on the dynamic property 205a is represented as a matrix. Correlations between several different types of dynamical properties are described by the information on the dynamic property, namely a correlation of (movement) trajectories (first line in the matrix of FIG. 21) and a correlation of temperature change (second line in the matrix of FIG. 21).

The correlation in the first line, first column of the matrix is a correlation between the trajectory of the atlas segment 204a (e.g. the first rib) and the trajectory of the atlas segment 204b (e.g. the diaphragm). The correlation in the first line, second column of the matrix is a correlation between the trajectory of the atlas segment 204a (e.g. the first rib) and the trajectory of the atlas segment 204c (e.g. the heart). The correlation in the first line, third column of the matrix is a correlation between the trajectory of the atlas segment 204a (e.g. the first rib) and the trajectory of the atlas segment 204d (e.g. the second rib). In the shown example, a numerical value (in the example: 1, 9 and 5) as well as an indicator (in the example: "low", "high" and "medium") of the respective correlation is stored. Other parameters may be stored for each of the correlations (e.g. a value indicating correlation of the trajectories in a certain spatial direction, a difference of maximum or minimum values of the trajectories (for example in a certain spatial direction) etc.), for example measures of similarity of the trajectories.

The correlation in the second line, first column of the matrix is a correlation between the temperature change of the atlas segment 204a (e.g. the first rib) and the temperature change of the atlas segment 204b (e.g. the diaphragm). The correlation in the second line, second column of the matrix is a correlation between the temperature change of the atlas segment 204a (e.g. the first rib) and the temperature change of the atlas segment 204c (e.g. the heart). The correlation in the second line, third column of the matrix is a correlation between the temperature change of the atlas segment 204a (e.g. the first rib) and the temperature change of the atlas segment 204d (e.g. the second rib). In the shown example, a numerical value (in the example: 97, 52 and 8) as well as an indicator (in the example: "high", "medium" and "low") of the respective correlation is stored. Other parameters may be stored for each of the correlations (e.g. a value indicating correlation of the temperature changes in a certain time range, a value indicating correlation of the rise in temperature, a value indication correlation of the sinking of temperature etc.).

Figure 22:
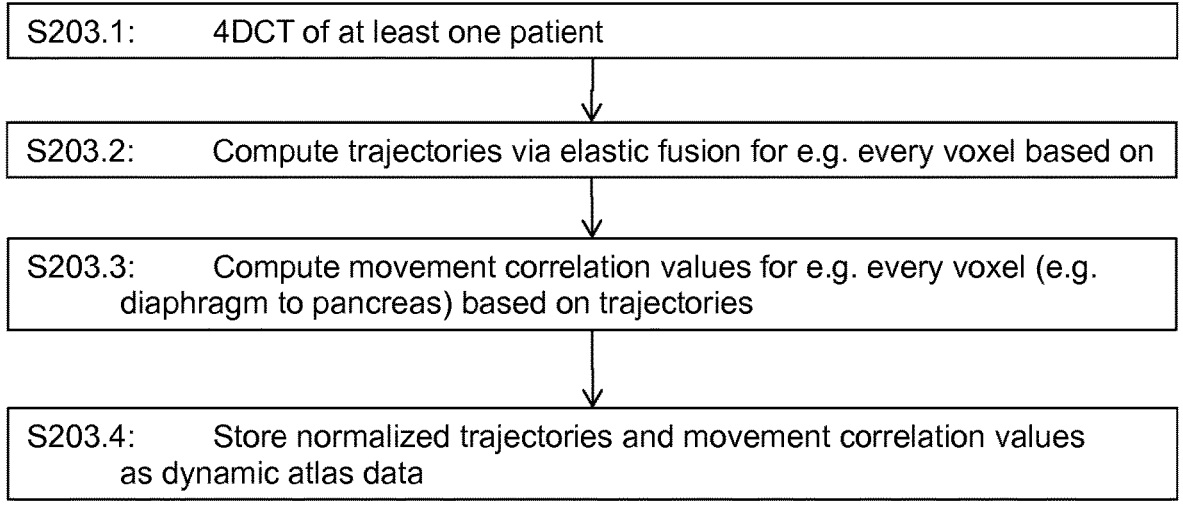
FIG. 22 shows a first sequence of steps of a specific embodiment of the method as described in Annex B.
Figure 23:
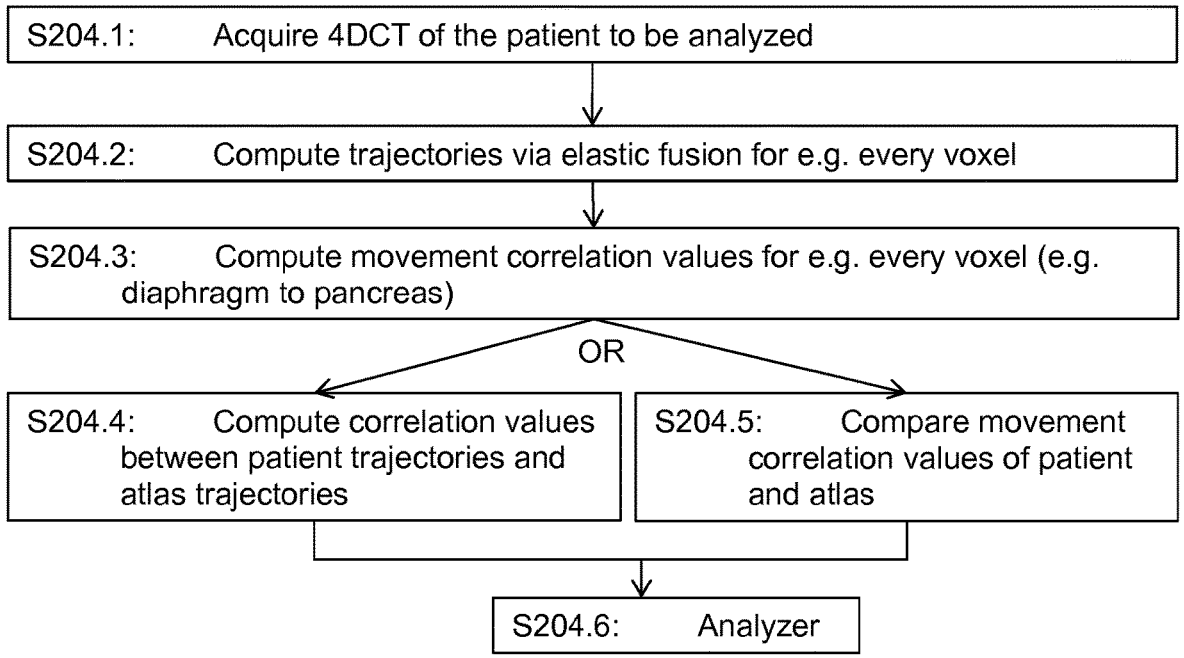
FIG. 23 shows a second sequence of steps of a specific embodiment of the method as described in Annex B.

FIG. 22 shows a first sequence of steps of a specific embodiment of the disclosed method. It should be noted that one or more of the method steps shown in FIGS. 22 and 23 can be performed at the same time or subsequently, some of the steps may be replaced or omitted and additional and/or alternative steps may be used, wherever possible. In other words, the sequence of steps shown in FIGS. 22 and 23 is not the only embodiment covered by this disclosure.

The method concerns the generation, improvement and/or enrichment of the dynamic anatomic atlas, in particular the generation of the information on the dynamic property. The depicted method comprises several steps S203.1 to S203.4. It should be noted that other and/or alternative and/or additional steps can be used to generate the information on the dynamic property. For instance, several (f)MRT images may be used to determine the change concentration of oxygen in certain segments.

In the first exemplary step S203.1, a 4DCT of at least one patient is acquired (e.g. loaded into a computer). Of course, other imaging modalities are possible as long as image data is acquired in step S203.1 which represents the patient at different points in time. For example, a 4DCT scan can be used which includes several 3DCT scans and information on their timely sequence (timely dependencies). For example, several 3DCTs can be acquired which represent the patient at different points in time. These can be combined into a 4DCT.

In the next exemplary step S203.2, a group of voxels or each individual voxel of a first 3D CT data set (e.g. acquired and/or generated in step S203.1) is matched with a corresponding group of voxels or a corresponding individual voxel of a second 3D CT data set which represents an image of the patient at a different point in time than the first 3D CT data set. Elastic fusion may be used for the matching. This step may be repeated with several image data representing the patient at further different points in time. Consequently, the position of the group of voxels or of the individual voxel depending on the point in time can be determined. Connecting all the determined positions results in a (e.g. closed-loop) trajectory which describes the time-dependent movement of the group of voxel or of each individual voxel.

In the next exemplary step S203.3, movement correlation values are calculated, for example for each individual voxel for which a trajectory has been determined (e.g. in step S203.2). The movement correlation values may be determined by forming a correlation of a first trajectory of a first voxel with a second trajectory of a second voxel. For example, a plurality of movement correlation values of a first trajectory of a first voxel with respect to other trajectories of several (or all) other voxels are determined.

In the next exemplary step S203.4, the trajectories are normalized. For example, the trajectories are normalized with respect to a reference trajectory. For example, a first plurality of trajectories of a first plurality of voxels are normalized in a different way (other reference, other normalization method, . . . ) than a second plurality of trajectories of a second plurality of voxels. For example, all voxels which are part of a first anatomical body part are normalized in the same manner. The anatomical body part may be determined by matching one of the plurality of patient images with a static atlas image or by a user. For example, normalization is performed so that each patient segment (representing an anatomical body part of the patient) is associated with a certain trajectory and certain movement correlation values (e.g. by averaging the trajectories of all voxels within the patient segment).

After normalization, the normalized trajectories and the movement correlation values (e.g. determined in step S203.3) which are associated with a certain patient segment are stored as dynamic atlas data 203 in the dynamic anatomic atlas 201. For this purpose, the normalized trajectories and the movement correlation values should be respectively linked to the individual atlas segments. Therefore, at least one of the patient images used to obtain the normalized trajectories is matched with a static atlas image. Image fusion may be used to determine a corresponding patient segment which corresponds to a corresponding atlas segment. Afterwards, the information on the dynamic property (e.g. 205a) of the corresponding patient segment (the information for example comprising the normalized trajectory and the (normalized) movement correlation values, e.g. the trajectory of a rib) is stored in the dynamic anatomic atlas 201 respectively linked with the corresponding atlas segment (e.g. the atlas segment 204a representing the rib). This results in the dynamic anatomic atlas 201 shown in FIG. 20.

FIG. 23 shows a second sequence of steps of a specific embodiment of the disclosed method. For example, the method includes one or more of the steps shown in FIG. 21 (S203.1 to S203.4) and continues with one of the steps shown in FIG. 23. For example, the dynamic anatomic atlas 1 has already been created (is available), and the method starts with step S204.1. In exemplary step S204.1, a 4DCT of a patient to be analyzed is acquired (e.g. loaded into a computer). As noted above, alternative imaging modalities may be used as long as they include information on a time-dependent behavior of the patient, e.g. a series of patient images representing the patient at different points in time.

In the next exemplary step S204.2, information of the dynamic properties is determined, i.e. trajectories are calculated for each or some of the voxels of the patient image (e.g. acquired in step S204.3). The (closed-loop and/or cyclic) trajectories may be calculated as described above with respect to step S203.2 and may describe the time-dependent position of a voxel or of a group of voxels.

In exemplary step S204.3, movement correlation values are calculated for every voxel or for some of the voxels or for the groups of voxels. As movement correlation values, correlations between different trajectories may be used (as described above with respect to step S203.3).

In a next exemplary step S204.4, correlation values between patient trajectories and atlas trajectories are computed (e.g. determined or calculated). For this purpose, only the trajectories are needed which means that step S204.4 can directly follow step S204.3. For example, a correlation between the trajectory of a corresponding patient segment and the trajectory of a corresponding atlas segment is determined. As noted earlier with respect to FIG. 22, to identify the corresponding patient and atlas segments, a patient image used to generate the trajectories can be matched with a static atlas image (e.g. via image fusion). Alternatively or additionally to step S204.5, step S204.5 may be performed.

In exemplary step S204.5, the movement correlation values of the patient and of the atlas are compared. For example, the movement correlation values of a corresponding patient segment are compared with the movement correlation value of the corresponding atlas segment. The comparison may include mathematical functions such as subtraction, division, addition, multiplication, differentiation, integration, a combination thereof or else. As a result of the comparison, a certain numerical value may be determined.

Following step S204.4 and/or step S204.5, the correlation values determined in step S204.4 and/or the comparison result determined in step S204.5 are input into an analyzer in exemplary step S204.6. The analyzer uses one or both of the aforementioned data to determine a degree of similarity between the patient and the atlas, for example between the dynamic property of the corresponding patient segment and the dynamic property of the corresponding atlas segment. This analysis may be used to classify the patient according to a certain patient type. Alternatively and/or additionally, this analysis may be used as an indicator for a certain disease (e.g. in case a certain patient segment moves different compared with a corresponding atlas segment, i.e. in case of a tumor which is attached to an anatomical structure which moves differently). Other ways of using the comparison between the dynamic property of one or more patient segments and the dynamic property of the one or more corresponding atlas segments are also possible, for example as laid out in the general description above.

Figure 24:
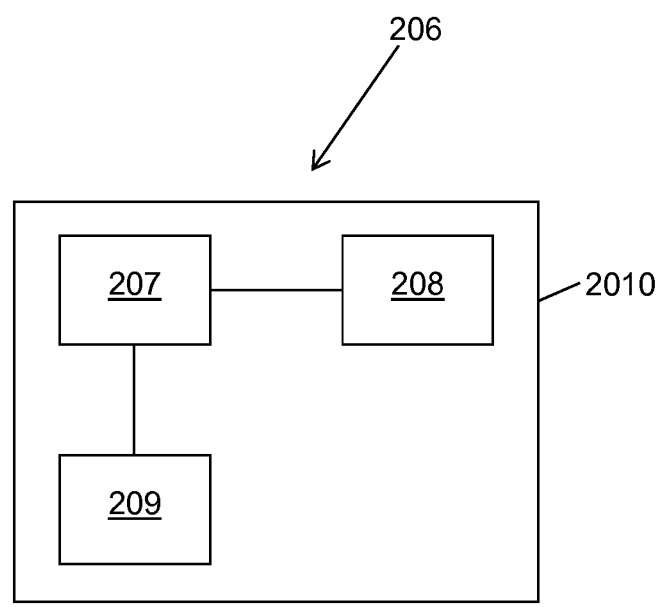
FIG. 24 shows a principle configuration of a system of a specific embodiment as described in Annex B.

FIG. 24 shows a principle configuration of a system of a specific embodiment of Annex B: the system 206 comprises a computing environment 2010 including at least one computer 207 having at least one digital electronic processor which is operably coupled to at least one electronic data storage device 208 and an output device 209 (e.g. a graphical output device such as a display). The electronic data storage device 208 stores at least medical image data, the dynamic anatomic atlas 201 or a program. The computer 207 is configured to output, to the output device 9, electronic signals representing a (graphical) representation of a result of the data processing conducted by the computer 207. Furthermore, the computing environment 2010 can be coupled to other devices such as a patient positioning device, a patient treatment device (for example a radiotherapy and/or radiosurgery device), one or more medical imaging devices (imagers), other computing systems such as a cloud based computing system or else.

According to an exemplary embodiment, based on elastically fused 4D CTs specific points of a base CT can be transferred into CTs of different breathing phases, i.e. CTs of the patient describing the patient at different points in time. The transferring results in different positions of the specific points in each of the images, which can be represented by a (closed) trajectory in space. The target is now to find out, which trajectories are correlated in a specific patient, i.e. which points behave similar under breathing. And for comparison it might be interesting to know which points in a human body do normally correlate. A general correlation map is preferably generated in atlas space, stored as meta information of the Universal Atlas. But the averaging of meta information is challenging since the information, which is used for averaging, must be comparable between different patients independent of their breathing behavior. The information should therefore be normalized. The first step for an averaged correlation representation is to choose a set of points between which the correlation should be calculated. It can be done for every voxel or just for every organ or part(s) of an organ. For this purpose, the human body, i.e. of the universal atlas, could be divided into a plurality of cells. A point (e.g. at the center) of each cell might thereafter be identified as a reference for the individual cell. A number of 4D CTs of different individuals, which must be registered to the atlas (and or elastically fused to each other inside a 4D CT series) are required to create the dynamic atlas data. Then, the center points can be transformed (e.g. projected and/or matched) to the different data sets of the 4D CT series. For each 4D CT series and each center point a trajectory can be obtained with points pi (i=1 to n). An appropriate normalized correlation measure is e.g. the cross correlation between two trajectories p and q (or component-wise or weighted). All correlations between all center point trajectories corr(cellk,celll) can be calculated as a huge matrix. This matrix can be averaged between different individuals and stored per cell pair as meta information in the atlas. The direction of each trajectory can also be calculated. This direction can also be averaged and stored per cell. The direction is not a scalar. It must be back-transformed into the atlas before averaging.

In the following, several aspects of Annex B are provided.

Aspect 1. A dynamic anatomic atlas is comprising:
static atlas data describing atlas segments; and
dynamic atlas data comprising information on a dynamic property which information is respectively linked to the atlas segments.

Aspect 2. The dynamic anatomic atlas of aspect 1., wherein the information on the dynamic property describes correlations between the dynamic properties of different ones of the atlas segments.

Aspect 3. The dynamic anatomic atlas of one of the aspects 1. or 2., wherein the information on the dynamic property describes at least one normalized dynamic property of at least one atlas segment.

Aspect 4. The dynamic anatomic atlas of one of the aspects 1. to 3., wherein at least one dynamic property linked to an atlas segment is classified according to patient types.

Aspect 5. The dynamic anatomic atlas of one of the aspects 1. to 4. comprising information on a distribution of at least one dynamic property.

Aspect 6. The dynamic anatomic atlas of one of the aspects 1. to 5. comprising an atlas segment subdivided into atlas subsegments respectively linked with different dynamic properties while exhibiting the same segment representation information.

Aspect 7. A computer implemented data processing method comprising the step of acquiring a dynamic anatomic atlas of one of the aspects 1. to 6.

Aspect 8. A computer implemented data processing method for generating the dynamic anatomic atlas of one of the preceding aspects, the method comprising the following steps:
based on the static atlas data a static atlas image of the atlas segments is acquired;
static patient data describing a static patient image of a patient segment is acquired;
dynamic patient data comprising information on a dynamic property is acquired, the information being respectively linked to the patient segment;
the static patient image is matched with the static atlas image;
a corresponding atlas segment corresponding to the patient segment is determined based on the matching;
for generating the dynamic anatomic atlas, the information on the dynamic property linked to the corresponding atlas segment is determined based on the information on the dynamic property linked to the patient segment.

Aspect 9. The computer implemented data processing method of aspect 8., the method comprising at least one of the following steps:
based on the information on the dynamic properties linked to different patient segments correlations between the dynamic properties of the different patient segments are calculated for determining the correlations of aspect 2.; and
based on at least the information on the dynamic property linked to a patient segment at least one normalized dynamic property for the patient segment is calculated for determining the at least one normalized dynamic property of aspect 3.

Aspect 10. The computer implemented data processing method of aspect 8. or 9., wherein, based on subregions exhibiting different dynamic properties within the corresponding patient segment, atlas subsegments corresponding to the dynamic subregions are determined.

Aspect 11. A computer implemented data processing method for enabling an analysis of an anatomic dynamic of a patient, the method comprising the following steps:
the static atlas data and the dynamic atlas data of the dynamic atlas of one of the aspects 1. to 7. are acquired, the static atlas data describing a static atlas image;
static patient data describing a static patient image of a patient segment is acquired;
dynamic patient data comprising information on a dynamic property is acquired, the information being respectively linked to the patient segment;
the static patient image is matched with the static atlas image;
a corresponding atlas segment corresponding to the patient segment is determined based on the matching;
for enabling the analysis, the information on the dynamic property linked to the corresponding atlas segment and the information on the dynamic property linked to the patient segment are compared.

Aspect 12. The computer implemented data processing method of aspect 11., further comprising the following steps:
the static atlas data and the dynamic atlas data of the dynamic atlas of the aspect 4. are acquired;
at least one classified dynamic property of the corresponding atlas segment is compared with the dynamic property of the patient segment; and
based on the comparison, the type of the patient is determined.

Aspect 13. The computer implemented data processing method of aspect 12., further comprising the following steps:
the static atlas data and the dynamic atlas data of the dynamic atlas of aspect 5. are acquired;
based on the comparison and based on the information on the distribution of the at least one dynamic property, it is determined whether the determined dynamic property of the corresponding patient segment is within a predefined range or not.

Aspect 14. Use of the dynamic anatomic atlas of any one of aspects 1. to 6. for matching a patient image and an atlas image or for matching two patient images, comprising the following step:
the information on the dynamic property of at least one atlas segment is used as a constraint for the matching.

Aspect 15. Use of the dynamic anatomic atlas of the aspect 6. and comprising the following steps:
the static atlas data and the dynamic atlas data of the dynamic atlas of aspect 6. are acquired, the static atlas data describing a static atlas image of the atlas segments;
static patient data describing a static patient image of a patient segment is acquired;
the static patient image is matched with the static atlas image;
a corresponding atlas segment corresponding to the patient segment is determined based on the matching;
subsegments within the patient segment are determined based on the atlas subsegments of the corresponding atlas segment.

Aspect 16. The dynamic anatomic atlas of one of aspects 1. to 6., the computer implemented data processing method of one of aspects 7. to 13. or the use of the dynamic atlas of one of aspects 14. or 15., wherein the dynamic property is at least one of the following:
dynamic spatial information, comprising at least one of
i. information on a change of position of an object or
ii. information on a change of geometry of an object;
dynamic thermodynamic information, comprising at least one of
i. information on a change of temperature of an object or
ii. information on a change of pressure of an object or
iii. information on a change of volume of an object;
fluid-dynamic information, comprising at least one of
i. information on a change of flux or
ii. information on a change of velocity of a substance within an object or
iii. information of a change of density of a substance within an object, wherein the object is at least one of the patient segment or a subsegment thereof or one of the atlas segments or a subsegment thereof.

Aspect 17. A computer program which, when running on at least one processor of at least one computer or when loaded into the memory of at least one computer, causes the at least one computer to perform the method according to one of aspects 7. to 13., or a signal wave, for example a digital signal wave, carrying information which represents the program.

Aspect 18. A non-transitory computer-readable program storage medium on which the program according to the aspect 17. is stored.

Aspect 19. At least one computer, comprising at least one processor and a memory, wherein the program according to aspect 17. is running on the at least one processor or is loaded into the memory, or wherein the at least one computer comprises the program storage medium according to aspect 18.

The invention claimed is:
1. A computer implemented method comprising:
acquiring a two-dimensional (2D) patient image describing anatomical patient structures of a patient;
acquiring an identified three-dimensional ("3D") tracking structure of the patient,
wherein the identified 3D tracking structure corresponds to an anatomical structure of the patient identified based on processing the 2D patient image,
wherein the identified 3D tracking structure is defined in a three-dimensional coordinate system, and
wherein the identified 3D tracking structure is a structure to be tracked using 3D tracking images from additional medical image data;
tessellating the identified 3D tracking structure into a plurality of 3D sub-tracking structures that are formed having a same range of similarity of movement, for tracking the plurality of 3D sub-tracking structures individually in the three-dimensional coordinate system,
wherein the plurality of 3D sub-tracking structures includes a first sub-tracking structure having a target structure for treatment and one or more second sub-tracking structures different from the first sub-tracking structure, and
wherein subsequent to the tessellating: relative positions of voxels in an individual 3D sub-tracking structure, of the plurality of 3D sub-tracking structures, do not change relative to each other, voxels in different 3D sub-tracking structures are allowed to change their relative positions; and
determining, for at least one of the second sub-tracking structures, a measure of similarity of movement with respect to the first sub-tracking structure.

2. The method of claim 1, further comprising:
matching at least some of the plurality of 3D sub-tracking structures with the anatomical patient structures described by the 2D patient image.

3. The method of claim 2, further comprising:
individually tracking the matched 3D sub-tracking structures.

4. The method of claim 2, wherein a dynamic DRR is determined based on the 2D patient image, and wherein the identified 3D tracking structure is identified further using dynamic atlas.

5. The method of claim 1, further comprising:
selecting one or more 3D sub-tracking structures, from the plurality of 3D sub-tracking structures, for tracking based on predetermined criteria.

6. The method of claim 5, further comprising:
individually tracking the selected one or more 3D sub-tracking structures.

7. The method of claim 6, further comprising:
determining an overall tracking position of the identified 3D tracking structure based on the tracking of the selected one or more 3D sub-tracking structures.

8. The method of claim 6, further comprising:
determining at least one of a position and geometry of the target structure for treatment based on the tracking of the selected one or more 3D sub-tracking structures.

9. The method of claim 6, further comprising:
determining a deformation of the target structure for treatment, based on the tracking of the selected one or more 3D sub-tracking structures.

10. The method of claim 5, further comprising:
determining whether the selected one or more 3D sub-tracking structures fulfill the predetermined criteria, wherein the predetermined criteria define one or more threshold values associated with a positional change of the selected one or more 3D sub-tracking structures;
if it is determined that the selected one or more 3D sub-tracking structures fulfill the predetermined criteria,
determining an overall tracking position of the identified 3D tracking structure based on the tracking of the selected one or more 3D sub-tracking structures; and
if it is determined that the selected one or more 3D sub-tracking structures do not fulfill the predetermined criteria,
identifying a new 3D tracking structure,
acquiring the identified new 3D tracking structure, and
tessellating the new 3D tracking structure into a plurality of new 3D sub-tracking structures; and
acquiring a patient image describing anatomical patient structures and matching at least some of the plurality of new 3D sub-tracking structures with the anatomical patient structures described by the patient image.

11. The computer-implemented method of claim 1, wherein the measure of similarity of movement for a second sub-tracking structure with respect the first sub-tracking structure comprises a square of magnitude of difference between:
a first value corresponding to the difference between a first position of the second sub-tracking structure at a first time and a second position of the second sub-tracking structure at a second time, and
a second value corresponding to the difference between a first position of the first sub-tracking structure at the first time and a second position of the first sub-tracking structure at the second time.

12. The method of claim 1, further comprising:
individually tracking the plurality of 3D sub-tracking structures.

13. The method of claim 1, further comprising:
displaying a slider that enables a user to set a threshold value for the measure of similarity of movement, and
modifying the 3D tracking images to render: the first sub-tracking structure having the target structure, and one or more of the second sub-tracking structures that satisfy the threshold value for the measure of similarity of movement.

14. A non-transitory computer-readable storage medium including instructions which, when executed by at least one processor of at least one computer cause the at least one computer to perform operations comprising:
acquiring a two-dimensional (2D) patient image describing anatomical patient structures of a patient;
acquiring an identified three-dimensional ("3D") tracking structure of the patient,
wherein the identified 3D tracking structure corresponds to an anatomical structure of the patient identified based on processing the 2D patient image,
wherein the identified 3D tracking structure is defined in a three-dimensional coordinate system, and
wherein the identified 3D tracking structure is a structure to be tracked using 3D tracking images from additional medical image data; and
tessellating the identified 3D tracking structure into a plurality of 3D sub-tracking structures that are formed having a same range of similarity of movement, for tracking the plurality of 3D sub-tracking structures individually in the three-dimensional coordinate system,
wherein the plurality of 3D sub-tracking structures includes a first sub-tracking structure having a target structure for treatment and one or more second sub-tracking structures different from the first sub-tracking structure, and
wherein subsequent to the tessellating: relative positions of voxels in an individual 3D sub-tracking structure, of the plurality of 3D sub-tracking structures, do not change relative to each other, voxels in different 3D sub-tracking structures are allowed to change their relative positions; for at least one of the second sub-tracking structures, measure of similarity of movement is determined with respect to the first sub-tracking structure; and
modifying, based on the measure of similarity of movement for the at least one of the second sub-tracking structures, the 2D patient image.

15. A system, comprising:
one or more processors; and
a storage medium storing instructions that, when executed by the one or more processors, cause the one or more processors to perform operations including:
acquiring a two-dimensional (2D) patient image describing anatomical patient structures of a patient;
acquiring an identified three-dimensional ("3D") tracking structure of the patient,
wherein the identified 3D tracking structure corresponds to an anatomical structure of the patient identified based on processing the 2D patient image,
wherein the identified 3D tracking structure is defined in a three-dimensional coordinate system, and wherein the identified 3D tracking structure is a structure to be tracked using 3D tracking images from additional medical image data; tessellating the identified 3D tracking structure into a plurality of 3D sub-tracking structures that are formed having a same range of similarity of movement, for tracking the plurality of 3D sub-tracking structures individually in the three-dimensional coordinate system, wherein the plurality of 3D sub-tracking structures includes a first sub-tracking structure having a target structure for treatment and one or more second sub-tracking structures different from the first sub-tracking structure, and wherein subsequent to the tessellating: relative positions of voxels in an individual 3D sub-tracking structure, of the plurality of 3D sub-tracking structures, do not change relative to each other, voxels in different 3D sub-tracking structures are allowed to change their relative positions; and determining, for at least one of the second sub-tracking structures, measure of similarity of movement with respect to the first sub-tracking structure.

* * * * *